United States Patent [19] [11] Patent Number: 4,999,363
Oshima et al. [45] Date of Patent: Mar. 12, 1991

[54] TRICYCLIC COMPOUNDS

[75] Inventors: Etsuo Oshima, Shizuoka; Hiroyuki Obase, Mishima; Akira Karasawa, Shizuoka; Kazuhiro Kubo, Shizuoka; Ichiro Miki, Shizuoka; Akio Ishii, Shizuoka, all of Japan

[73] Assignee: Kyowa Hakko Kogyo Co., Ltd., Tokyo, Japan

[21] Appl. No.: 368,242

[22] Filed: Jun. 6, 1989

[30] Foreign Application Priority Data

Jun. 9, 1988 [JP] Japan ............................ 63-142374

[51] Int. Cl.$^5$ .................... A61K 31/44; C07D 405/12
[52] U.S. Cl. ................................ 514/332; 546/269;
546/285; 549/354; 514/332; 514/345; 514/349;
514/356; 514/351; 514/352; 514/354; 514/355;
514/356; 514/357; 514/824; 514/821
[58] Field of Search ............... 546/269, 285; 549/354;
514/337, 826, 824, 344, 395, 310, 349, 351, 352, 354, 355, 356, 357, 332

[56] References Cited

U.S. PATENT DOCUMENTS

| 3,354,155 | 11/1967 | Tretter | 260/240 |
| 3,420,851 | 1/1969 | Bloom et al. | 260/333 |
| 4,282,365 | 8/1981 | Rokach et al. | 548/252 |
| 4,396,550 | 8/1983 | Takizawa et al. | 549/354 |
| 4,465,835 | 8/1984 | Takizawa et al. | 546/133 |
| 4,585,788 | 4/1986 | Helsley et al. | 514/450 |
| 4,596,804 | 6/1986 | Takizawa et al. | 514/25 |
| 4,749,703 | 6/1988 | Uso et al. | 514/253 |

FOREIGN PATENT DOCUMENTS

| 0085870 | 8/1983 | European Pat. Off. |
| 188802 | 7/1986 | European Pat. Off. |
| 214779 | 3/1987 | European Pat. Off. |
| 0235796 | 9/1987 | European Pat. Off. |
| 139073 | 8/1982 | Japan |
| 227879 | 12/1984 | Japan |
| 25798 | 11/1986 | Japan |
| 152673 | 11/1986 | Japan |
| 152674 | 11/1986 | Japan |
| 152675 | 11/1986 | Japan |
| 152676 | 11/1986 | Japan |
| 153280 | 8/1987 | Japan |

OTHER PUBLICATIONS

J. Metusova, et al., Arz. Forcsch, "Pharmakologische Eigenschaften der 6, 11-Dihydrodibenz (b,e)-Thiepene-Derivate," 13, pp. 1039-1045, (1963).
O. Benesova, et al., Arz. Forcsch., "Uber Ligre Zentrale Wilkungen von Prothiaden," 14, pp. 100-105 (1964).
R. Pinder, Drugs, "Dixepin Up-to-Date," 13, 161-167, (1977).
J. Med. Chem. 19, 941 (1976).
J. Med. Chem. 20, 1499 (1977).
J. Med. Chem. 21, 633 (1978).

Primary Examiner—Richard C. Raymond
Assistant Examiner—M. W. Russell
Attorney, Agent, or Firm—Fitzpatrick, Cella, Harper & Scinto

[57] ABSTRACT

Novel tricyclic compound represented by formula

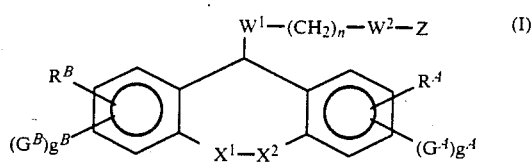

possess a TXA$_2$ biosynthesis inhibiting activity and/or a TXA$_2$ receptor antagonizing activity, and are expected to have preventive and therapeutic effects on ischemic diseases, cerebro-vascular diseases, etc.

8 Claims, No Drawings

TRICYCLIC COMPOUNDS

BACKGROUND OF THE INVENTION

The present invention relates to novel tricyclic compounds which strongly antagonize a biological action of chromboxane A2 (hereafter referred to as "TXA2") by an inhibitory activity of TXA2 biosynthesis and/or a TXA2 receptor antagonizing activity.

It is hitherto known that TXA2 strongly aggregates platelets and is a potent vasoconstrictor [cf. Arachidoic Acid Cascade and Drugs, edited by Shozo Yamamoto, Gendai Iryo Publishing Co., Ltd. (1985)]. Further TXA2 is a powerful vasoconstrictor against bronchus and bronchial smooth muscle. Therefore, TXA2 is considered to take part in pathological conditions over a wide range. As examples, the following diseases can be exemplified.

(1) Ischemic disease

For example, myocardial infarction, angina pectoris, and thrombosis (2) Cerebro-vascular disease For example, transient ischemic attack, migraine, cerebral hemorrhage, and cerebral infarction (3) Peripheral vascular diseases and disease caused by unbalanced lipid For example, atherosclerosis, capillary convulsion, peripheral circulation disorders, hypertension, pulmonary embolism (4) Inflammatory and allergic diseases For example, bronchial asthma, bronchitis, pneumonia, nephritis, and hepatitis (5) Shock (6) Cancer metastasis.

Accordingly, compounds that antagonize the action of TXA2 (compounds having an inhibitory action of TXA2 biosynthesis and/or a TXA2 receptor antagonizing action) are expected to have therapeutic effects in preventing or treating optional one or more of the diseases described above or other diseases in which the action of TXA2 is desirably prevented. Further where, in drugs used for medical purposes heretofore, application thereof is limited due to side effects mediated by TXA2 or considered to be mediated by TXA2, it is expected to alleviate the side effects by the use of compounds which antagonize the action of TXA2.

As inhibitors against biosynthesis of TXA2, representative compounds are exemplified in Journal of Organic Synthesis Chemistry, 45, 2 (1987). In addition, compounds having the following structures can be illustrated.

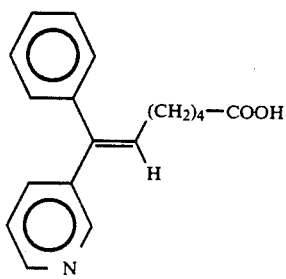

[J. Med. Chem., 28, 287 (1985)]

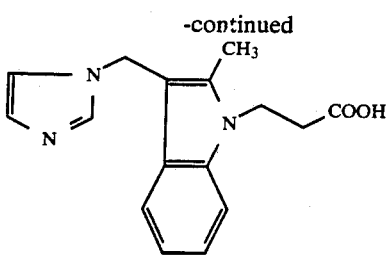

[Br.J. Pharmacol., 77, 547P (1982)]

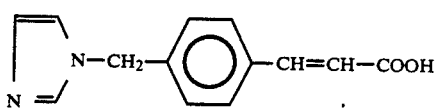

[J. Med. Chem., 24, 1139 (1981)]

The compounds contain a pyridine or imidazole partial structure and carboxyl therein and it is known that these functional groups are important for developing the action.

On the other hand, as an antagonist of TXA2, representative compounds are exemplified in Thrombosis Research, 44, 377 (1986).

Furthermore, an indole compound having the following structure:

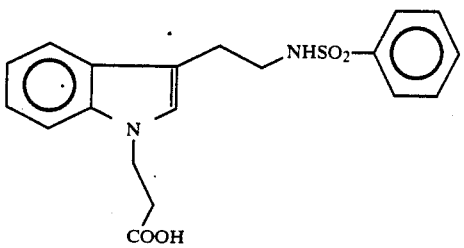

and the like are disclosed in Japanese Published Unexamined Patent Application No. 249960/1986 [West German Patent Application (DE) No. 3,514,696] and a compound having the following structure:

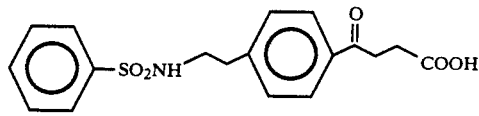

and the like are disclosed in Japanese Published Unexamined Patent Application No. 212552/1986 [DE 3,508,692]. These compounds are all derivatives having a phenylsulfonamide group and exhibit an activity of antagonizing TXA2.

Furthermore, there is reported a finding on the enhanced or complementary effect of the two activities by the use of TXA2 biosynthesis inhibitors and TXA2 receptor antagonists in combination [Eur. J. Pharmacol., 85, 331 (1982)].

There is also a report on compounds having both TXA2 biosynthesis inhibitory action and TXA2 receptor antagonizing action [Thromb. Haemostasis, 58, 664 (1987), etc.].

In tricyclic compounds in association with the present invention which are represented by the following formula (II):

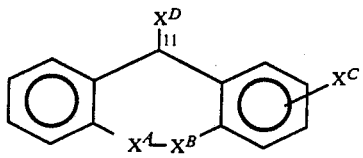
(II)

oxepine derivatives (wherein $X^A$—$X^B$ is —CH$_2$O—) having carboxyl or a derivative thereof (for example, an ester, an amide, etc.; hereafter collectively referred to as a carboxylic acid group) as a substituent ($X^C$) on the benzene ring wherein the 11-position ($X^D$) is unsubstituted or has various substituents such as oxo (=O), methylene (=CH$_2$), alkoxy, etc. are known as showing antiinflammatory and antiallergic activities, and the like [J. Med. Chem., 19, 941 (1976); ibid., 20, 1499 (1977); ibid, 21, 633 (1978); U.S. Pat. No. 4,282,365 (Japanese Published Unexamined Patent Application No. 21679/1983); U.S. Pat. No. 4,585,788, Japanese Published Unexamined Patent Application Nos. 152673/1986, 152674/1986 and 152675/1986].

There are also known oxepine derivatives showing antiasthmic and antiallergic activities, etc. wherein $X^C$ is unsubstituted or has a substituent other than the carboxylic acid group, for example, alkyl, alkoxy, halogen, etc. and $X^D$ has an alkylene chain substituted at the terminal thereof with alkylamino via hetero atom (—NH—, —O—, —S—, etc.), methine (=CH—), imino (=N—), etc. [Japanese Published Unexamined Patent Application Nos. 126883/1983 (EP 0085870A), 227879/1984 and 152669/1986; U.S. Pat. Nos. 3,354,155 and 3,420,851]. Furthermore, oxepine derivatives wherein $X^D$ contains phenyl or, an alicyclic or aromatic heterocyclic group at the terminal thereof via —NH— are known to show anticholinergic and antihistaminic activities, etc. [Japanese Published Unexamined Patent Application Nos. 150083/1981 (U.S. Pat. Nos. 4,396,550 and 4,465,835), and 139073/1982]. As the heterocyclic rings, piperazine, piperidine, morpholine, pyrrolidine, quinuclidine, pyridine, benzodioxane, indole and quinone are illustrated. Furthermore, cycloheptene derivatives ($X^A$—$X^B$ is —CH=CH—) or thiepine derivatives ($X^A$—$X^B$ is —CH$_2$S—) wherein $X^D$ contains at the terminal thereof an alicyclic saturated nitrogen-containing heterocyclic group, for example, piperazine, via —CONH— are known to show a calcium antagonizing activity [Japanese Published Unexamined Patent Application Nos. 47466/1986 (U.S. Pat. No. 4,749,703) and 153280/1987]. Furthermore, doxepin derivatives [$X^A$—$X^B$ is —CH$_2$O—; Drugs, 13, 161 (1977)] or dothiepin derivatives $X^A$—$X^B$ is —CH$_2$S—; Arz.-Forsch., 13, 1039 (1963), ibid., 14, 100 (1964)] wherein $X^C$ is hydrogen and $X^D$ has dimethylaminoisopropylidene as its substituent are known to show an antidepressive action.

Furthermore, oxepine derivatives having an antiallergic activity wherein $X^C$ has the carboxylic acid group and $X^D$ has an alkylene-chain substituted at the terminal thereof with alkylamino via a hetero atom, or its 11-position is directly bound to an alicyclic saturated heterocyclic ring such as piperazine or homopiperazine, etc. are known [Japanese Published Unexamined Patent Application Nos. 28972/1985 (U.S. Pat. No 4,596,804), 152670/1986, 152671/1986, 152672/1986, 152676/1986, 257981/1986 and 17877/1988]. Likewise, there are known compounds having an imidazole ring directly bound to its 11-position [Japanese Published Unexamined Patent Application No. 21679/1983 (U.S. Pat. No. 4,282,365)]. There are also disclosed oxepine or cycloheptene [$X^A$—$X^B$ is —CH$_2$CH$_2$—] derivatives showing an antihistaminic activity wherein $X^D$ is alkylaminoalkylidene [Japanese Published Unexamined Patent Application No. 45557/1987 (British Patent No. 8,520,662)]. Furthermore, there are disclosed oxepine derivatives showing antiallergic and antiinflammatory activities, etc. wherein $X^D$ contains at the terminal thereof alkylamino or alicyclic saturated nitrogen-containing heterocyclic group via methine, methylene or imino (Japanese Published Unexamined Patent Application No. 10784/1988). As the heterocyclic groups, 4-methylpiperazine, 4-methylhomopiperazine, piperidine, pyrrolidine, thiomorpholine and morpholine are exemplified.

Novel and useful TXA$_2$ antagonists (drugs having the TXA$_2$ biosynthesis inhibitory activity and/or TXA$_2$ receptor antagonizing activity) are expected to have preventive and therapeutic effects on various diseases, and are in demand.

SUMMARY OF THE INVENTION

An object of the present invention is to provide novel tricyclic compounds having, as the substituents, both an aromatic cyclic group such as aromatic hydrocarbon or aromatic heterocyclic group, etc. and carboxyl or its esters on the side chain thereof, which can prevent the action of TXA$_2$ such as a TXA$_2$ biosynthesis inhibitory activity and/or TXA$_2$ receptor antagonizing activity, etc.

In accordance with the present invention, there is provided a tricyclic compound [hereafter referred to as Compound (I); compounds having other formula numbers are similarly referred to] represented by formula (I):

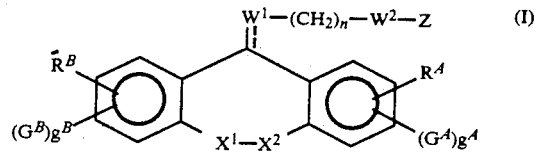
(I)

wherein:

represents
(a) single bond or
(b) double bond;

$X^1$-$X^2$ represents a group selected from:
(a) —CH$_2$—O—,
(b) —CH$_2$—S—,
(c) —CH$_2$—CH$_2$— and
(d) —CH=CH—;

each of $G^A$ and $G^B$ independently represents a group selected from:
(a) lower alkyl,
(b) halogen and
(c) —OR$^1$ wherein R$^1$ represents a group selected from:
(a)' hydrogen and
(b)' lower alkyl;

each of $g^A$ and $g^B$ independently represents 0, 1, 2 or 3;

one of R$^A$ and R$^B$ represents
(a) hydrogen and
the other represents
(b) —Y—COOR$^{1a}$ wherein
R$^{1a}$ has the same significance for R$^1$ as described above, Y represents:
(a)' single bond
(b)' —CR$^{1b}$R$^{1c}$—(CH$_2$)$_m$— and
(c)' —CR$^{1b}$=CR$^{1c}$—(CH$_2$)$_m$— wherein each of R$^{1b}$ and R$^{1c}$ independently has the same significance, for R$^1$ as described above and, m represents 0, 1, 2, 3 or 4, wherein the left side of the formula in (b)' and (c)' is bound to the mother nucleus;

W$^1$ represents a group selected from:
(a) —S—,
(b) —SO$_2$—,
(c) —O—,
(d) —NR$^{1d}$ wherein R$^{1d}$ has the same significance for R$^1$ as described above,
(e) —NHCO—,
(f) =N—,
(g) =CH— and
(h) —CH$_2$—;
  wherein the left side of the formula in (e) through (g) is bound to the mother nucleus;
n represents 0, 1, 2, 3 or 4;
W$^2$ represents a group selected from:
(a) single bond,
(b) —S— and
(c) —NR$^{1e}$— wherein R$^{1e}$ has the same significance for R$^1$ as described above;
Z represents an aromatic cyclic group selected from:

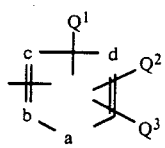 (a)

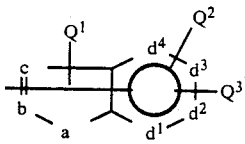 (b)

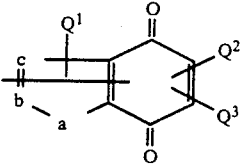 (c)

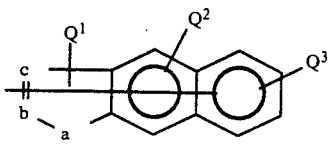 (d)

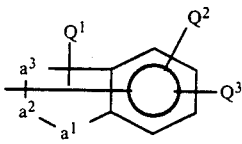 (e)

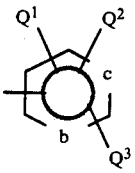 (f)

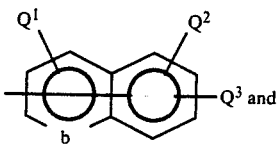 (g)

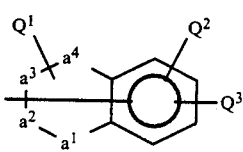 (h)

wherein each of a, a$^1$, a$^2$, a$^3$ and a$^4$ independently represents a group selected from:
(a)' —CH$_2$—
(b)' —NH—,
(c)' —O—,
(d)' —S— and
(e)' —SO$_2$—;
 each of b, c, d, d$^1$, d$^2$, d$^3$ and d$^4$ independently represents a group selected from:
(a)' =CH— and
(b)' =N—;
 each of Q$^1$, Q$^2$ and Q$^3$ independently represents a group selected from:
(a)' hydrogen,
(b)' lower alkyl,
(c)' benzyl,
(d)' substituted benzyl wherein each substituent on the phenyl in the substituted benzyl independently represents 1 to 3 groups selected from:
  (a)" halogen and
  (b)" —OR$^{1f}$ wherein R$^{1f}$ has the same significance for R$^1$ as described above;
 and, a substituent on the methylene represents one group selected from:
  (c)" —OR$^{1g}$ wherein R$^{1g}$ has the same significance for R$^1$ as described above;
(e)' phenyl,
(f)' halogen,
(g)' —CF$_3$,
(h)' nitro,
(i)' —CN,
(j)' —N$_3$,
(k)' —COOR$^2$,
(l)' —OR$^2$,
(m)' —OCOR$^2$,
(n)' —SR$^2$
(o)' —COR$^2$
(p)' —CONR$^{2a}$R$^{2b}$, wherein each of R$^{2a}$ and R$^{2b}$ independently represents R$^2$, wherein R$^2$ represents a group selected from:
  (a)" hydrogen,
  (b)" straight or branched alkyl having 1 to 18 carbon atoms,
  (c)" benzyl and
  (d)" phenyl;
(q)' methylenedioxy formed together with the ortho-position;

on the saturated carbon atom (methylene) of (e) and (h) in the definition for Z;
(r)' =O and,
(s)' =S
and pharmaceutically acceptable salts thereof.

DETAILED DESCRIPTION OF THE INVENTION

Examples of the ring constituting the aromatic cyclic group in the definition for Z in formula (I) include: (a) pyrrole, pyrazole, imidazole, triazole, thiadiazole, etc.; (b) indole, azaindole, isoindole, indazole, benzimidazole, azabenzimidazole, benzothiazole, benzotriazole, purine, etc.; (c) imidazobenzoquinone, etc.; (d) naphthoimidazole, etc.; (e) indoline, isoindoline, dihydroindazole, dihydrobenzimidazole, etc.; (f) benzene, pyridine, pyrimidine, etc.; (g) naphthalene, quinoline, isoquinoline, etc.; (h) tetrahydroquinoline, tetrahydroisoquinoline, benzothiazine, etc.

In the definition for $R^2$ in formula (I), the straight or branched alkyl having 1 to 18 carbon atoms includes methyl, ethyl, propyl, isopropyl, butyl, isobutyl, tert-butyl, pentyl, neopentyl, hexyl, heptyl, octyl, nonyl, decyl, undecyl, dodecyl, tridecyl, tetradecyl, pentadecyl, hexadecyl, heptadecyl, octadecyl, and the like.

In the definition for the respective groups in formula (I), the lower alkyl includes straight or branched alkyl having 1 to 6 carbon atoms, for example, methyl, ethyl, propyl, isopropyl, butyl, isobutyl, sec-butyl, tert-butyl, pentyl, hexyl, and the like; the halogen includes each atom of fluorine, chlorine, bromine and iodine.

The pharmaceutically acceptable salt of Compound (I) includes an acid addition salt, a metal salt, an ammonium salt, an organic amine addition salt, an amino acid addition salt, etc. which are pharmaceutically acceptable.

As the pharmaceutically acceptable acid addition salt of Compound (I), mention may be made of the inorganic acid salt such as hydrochloride, sulfate, phosphate, etc. and the organic acid salt such as acetate, maleate, fumarate, tartarate, citrate, etc. As the pharmaceutically acceptable metal salt, the alkali metal salt such as sodium salt, potassium salt, etc.; alkaline earth metal salt such as magnesium salt, calcium salt, etc. and further the aluminium salt and the zinc salt are appropriate. As the ammonium salt, mention may be made of the salt of ammonium, tetramethylammonium, etc. As the pharmaceutically acceptable organic amine addition salt, mention may be made of an addition salt of morpholine, piperidine, etc. As the pharmaceutically acceptable amino acid addition salt, an addition salt of lysine, glycine, phenylalanine or the like are mentioned.

Hereafter processes for producing Compound (I) are described below but the production of Compound (I) is not deemed to be limited thereto. In various processes, reaction conditions may be appropriately chosen from the following conditions.

A reaction solvent may be chosen from water or an organic solvent which does not participate in the reaction and can be used singly or as admixture. Examples of the organic solvent include an alcohol such as methanol, ethanol, propanol, isopropanol, etc.; and ether such as diethyl ether, dioxane, tetrahydrofuran, ethylene glycol monomethyl ether or ethylene glycol dimethyl ether, etc.; a hydrocarbon such as benzene, toluene, xylene, hexane, cyclohexane, petroleum ether, ligroin or decaline, etc.; a ketone such as acetone, methyl ethyl ketone, etc. an amide such as formamide, dimethylformamide, hexamethylphosphoric triamide, etc.; acetonitrile, ethyl acetate, dimethylsulfoxide, sulfolane or a halogenated hydrocarbon such as methylene chloride, dichloroethane, tetrachloroethane, chloroform or carbon tetrachloride, etc. Further in the case that bases or acids later described are liquid, they may also be used as a solvent.

As the appropriate base, an inorganic or organic base can be used. These bases include an alkali metal hydroxide, for example, lithium hydroxide, sodium hydroxide or potassium hydroxide; an alkali metal carbonate, for example, sodium carbonate, sodium hydrogencarbonate or potassium carbonate; an alkali metal acetate, for example, sodium acetate or potassium acetate; an alkali metal alkoxide, for example, sodium methoxide, sodium ethoxide or potassium tert-butoxide; or an organic metal compound, for example, sodium hydride, potassium hydride, lithium aluminum hydride, lithium borohydride, sodium triethylborohydride, methyl magnesium bromide, ethyl magnesium bromide, vinyl magnesium bromide, n-butyl lithium, sec-butyl lithium; or an organic amine, for example, triethylamine, tri-n-butylamine, pyridine, N,N-dimethylaminopyridine, picoline, lutidine, N,N-dimethylaniline, dicyclohexylmethylamine, N-methylpiperidine, morpholine, N-methylmorpholine, diazabicyclooctane, diazabicycloundecene or N-benzyltrimethylammonium hydroxide (Triton B), etc.

As the appropriate acid, an inorganic or organic acid or Lewis acid can be used. Examples of the inorganic acid include hydrochloric acid, hydrobromic acid, hydroiodic acid, sulfuric acid, nitric acid, hypochloric acid, sulfurous acid or nitrous acid, etc. Examples of the organic acid are formic acid, acetic acid, trifluoroacetic acid, benzoic acid, p-toluenesulfonic acid, camphorsulfonic acid or methanesulfonic acid, etc. Examples of the Lewis acid include aluminum chloride, zinc chloride, tin chloride, boron trifluoride, boron trifluoride diethyl ether complex, titanium tetrachloride, etc.

A reaction temperature is generally from −80° C. to a boiling point of a solvent. It is also possible to heat in the absence of any solvent used. In general, the reaction may be carried out under normal pressure but it is also possible to carry out the reaction under pressure. In this case, the reaction temperature may also be raised to a temperature higher than the boiling point of a solvent.

A reaction time is generally in a range of 1 minute to a week.

In the following description, preferred reaction conditions are given.

Further in the following description, for purposes of simplifying the reaction equations, the tricyclic moiety that does not directly participate in the reaction:

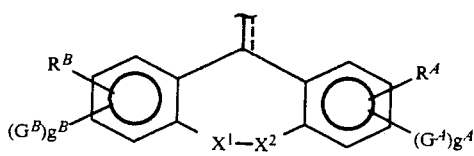

wherein , $X^1$-$X^2$, $G^A$, $G^B$, $R^A$, $R^B$, $g^A$ and $g^B$ have the same significances as described above; is sometimes referred to as:

Compound (I) can be prepared from Compound (III) or from Compounds (IVa-e) obtained from Compound (III) according to the following reaction steps:

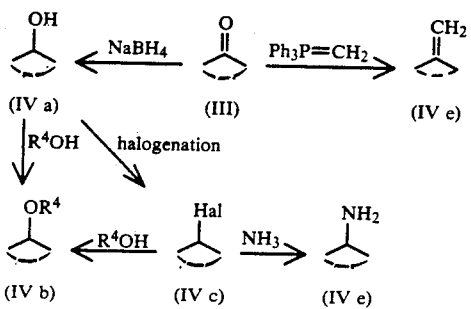

wherein

has the same significance as described above; $R^4$ represents lower alkyl, Hal represents halogen and Ph represents phenyl.

Herein the halogen shown by Hal represents chlorine, bromine and iodine and the lower alkyl is the same as defined for the lower alkyl for each group in formula (I).

Compounds (III) are either described in J. Med. Chem., 19, 941 (1976); ibid., 21, 1035 (1978); ibid., 20, 1557 (1977); ibid., 20, 1499 (1977); ibid., 29, 2347 (1986); ibid., 21, 633 (1978); ibid., 20, 456 (1977); U.S. Pat. Nos. 4,172,949 and 4,282,365; Japanese Published Unexamined Patent Application Nos. 21679/1983, 28972/1985, 152669/1986, 152672/1986, 152673/1986, 152675/1986 and 10784/1988, or can be synthesized according to the methods described in these publications or in a manner similar thereto.

Further the processes for producing Compounds (IVa-e) from Compound (III) can be carried out according to the methods described in Japanese Published Unexamined Patent Application Nos. 150083/1981, 28972/1985, 152670/1986, 152671/1986, 152672/1986, 152675/1986 and 10784/1988, etc. or in a manner similar thereto.

METHOD 1-1

[Synthesis of Compound (Ia) in Compound (I), wherein $W^1$ is $W^{1a}$ (part 1)]

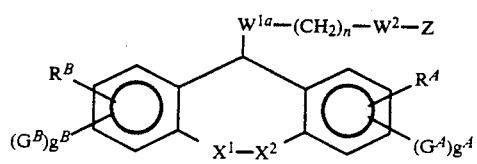

wherein $W^{1a}$ is —S—, —$SO_2$—, —O— or —$NR^{1d}$; $X^1$-$X^2$, $G^A$, $G^B$, $R^A$, $R^B$, $W^2$, Z, $R^{1d}$, $g^A$, $g^B$ and n have the same significances as described above.

Compound (Ia) can be produced from Compounds (IVa-c) and (Va) according to the following reaction steps.

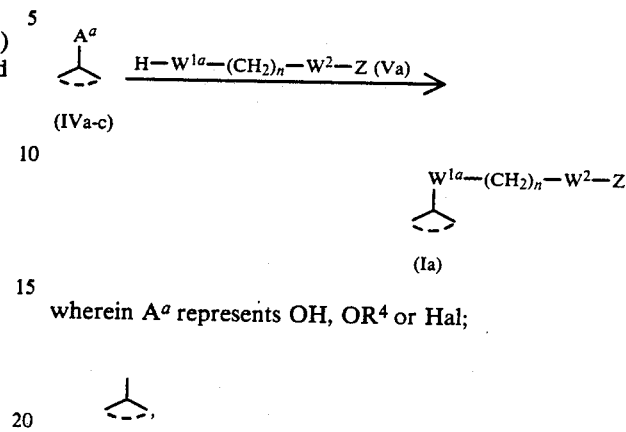

wherein $A^a$ represents OH, $OR^4$ or Hal;

$W^{1a}$, $W^2$, Z, $R^4$, Hal and n have the same significances as described above.

Compound (Ia) or acid addition salts thereof (which include, for example, a hydrochloride, a hydrobromide, an acetate, a trifluoroacetate and p-toluenesulfonate, etc.; in the following description, the acid addition salts also refer to these salts) can be obtained by reaction Compound (IVa) with 1 to 5 molar equivalents of an appropriate dehydrating and condensing agent, for example, trifluoroacetic anhydride, in an inert solvent such as methylene chloride, chloroform, etc., at a temperature of from 0° C. to room temperature for 1 to 24 hours, then adding 1 to 5 molar equivalents of Compound (Va) or acid addition salts thereof to the reaction solution and reacting the mixture between at 0° C. and a boiling point of the solvent, for 1 to 24 hours, if necessary and desired, in the presence of an appropriate acid catalyst, for example, boron trifluoride diethyl ether complex.

Compound (Ia) or acid addition salts thereof can also be obtained by reacting Compound (IVb) with 1 to 5 molar equivalents of Compound (Va) or acid addition salts thereof in an inert solvent such as methylene chloride, chloroform, etc., between at 0° C. and a boiling point of the solvent, if necessary and desired, in the presence of an appropriate acid catalyst, for example, boron trifluoride diethyl ether complex, for 1 to 24 hours.

Compound (Ia) or acid addition salts thereof can also be obtained by reacting Compound (IVc) with 1 to 10 molar equivalents of Compound (Va) or acid addition salts thereof either in an inert solvent such as toluene, methylene chloride, chloroform, N,N-dimethylformamide, etc., or using an organic base itself such as pyridine, etc. as a solvent, between at 0° C. and a boiling point of the solvent, if necessary and desired, in the presence of a base such as triethylamine, pyridine, sodium hydride, etc. for 1 to 48 hours.

METHOD 1-2

[Synthesis of Compound (Ia) (part 2)]

Compound (Ia) can also be obtained from Compounds (IVa-c) according to the following process.

Firstly, Compound (VIIb) or (VIIc) can be obtained from Compounds (IVa-c) according to the following reaction steps.

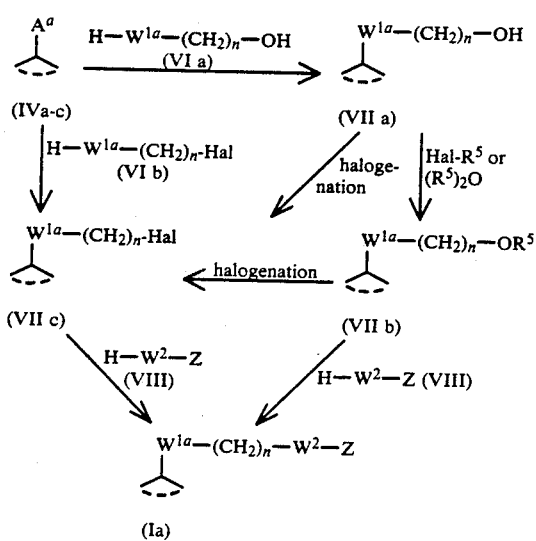

wherein

, $A^a$, $W^{1a}$, $W^2$, Z, Hal and n have the same significances as described above; and $R^5$ represents a group capable of being split as $OR^5$.

Herein, $R^5$ means an alkylsulfonyl group such as methanesulfonyl, trifluoromethanesulfonyl, etc. or an arylsulfonyl group such as phenylsulfonyl, p-toluenesulfonyl, etc.

The corresponding Compound (VIIa) or (VIIc) can be obtained by reacting Compound (IVa) with 1 to 5 molar equivalents of an appropriate dehydrating and condensing agent, for example, trifluoroacetic anhydride, in an inert solvent such as methylene chloride, chloroform, etc., at a temperature of from 0° C. to room temperature for 1 to 24 hours, then adding 1 to 10 molar equivalents of an alcohol (VIa) or its halide (VIb) to the reaction solution and reacting the mixture between at room temperature and a boiling point of the solvent, if necessary and desired, in the presence of an appropriate acid catalyst, for example, boron trifluoride diethyl ether complex, for 1 to 24 hours.

Compound (VIIa) or (VIIc) can be likewise obtained by reacting Compound (IVb) or (IVc) with 1 to 10 molar equivalents of an alcohol (VIa) or its halide (VIb) in an inert solvent such as methylene chloride, chloroform, etc., between at room temperature and a boiling point of the solvent, if necessary and desired, either in the presence of an appropriate acid catalyst, for example, boron trifluoride diethyl ether complex, or in the presence of an appropriate base, for example, triethylamine, for 1 to 24 hours.

The thus obtained Compound (VIIa) may be reacted with 1 to 5 molar equivalents of Hal-$R^5$ or $(R^5)_2O$ (wherein $R^5$ and Hal have the same significances as described above) at a temperature of from $-50°$ C. to room temperature for 1 to 24 hours in an inert solvent, for example, methylene chloride, chloroform, etc., if necessary and desired, in the presence of a base such as pyridine, etc. to give Compound (VIIb).

Furthermore, Compound (VIIc) may also be obtained by reacting Compound [VIIa] with 1 to 5 molar equivalents of a halogenating agent, for example, thionyl chloride, phosphorus pentachloride, phosphorus tribromide, etc., without a solvent or in an inert solvent such as methylene chloride, chloroform, etc., if necessary and desired, in the presence of a base such as pyridine, etc., at a temperature of from 0° C. to room temperature for 1 to 24 hours; or by reacting Compound (VIIa) with 1 to 10 molar equivalents of an alkyl halide such as methyl iodide at a temperature of from $-20°$ C. to the boiling point of the solvent, in an inert solvent such as benzene, if necessary and desired, in the presence of 1 to 10 molar equivalents of triphenylphosphine and 1 to 10 molar equivalents of diethyl azodicarboxylate, for 1 to 24 hours; or by reacting Compound (VIIa) with 1 to 10 molar equivalents of a halogenating agent such as methanesulfonyl chloride, etc., in the presence of 1 to 10 molar equivalents of a salt such as lithium chloride, in dimethylformamide at $-20°$ to 100° C. for 1 to 24 hours.

Where Compound (VIIc) is the chloride (Hal=Cl) or bromide (Hal=Br), the compound may be reacted further with an iodide, for example, sodium iodide, in a polar solvent such as acetonitrile to give the iodide (Hal=I). Compound (VIIb) can be converted into Compound (VIIc) under similar conditions.

Then, Compound (Ia) can be obtained by reacting Compound (VIIb) or Compound (VIIc) with 1 to 10 molar equivalents of Compound (VIII) or its acid addition salts in an inert solvent such as methylene chloride, chloroform, dichloroethane, N,N-dimethylformamide, dioxane, tetrahydrofuran, etc. or using as a solvent an organic base itself such as pyridine, etc., if necessary and desired, in the presence of a base such as sodium carbonate, triethylamine, pyridine, Triton B, sodium hydride, potassium hydride, lithium aluminum hydride, lithium borohydride, sodium triethylborohydride, methyl magnesium bromide, ethyl magnesium bromide, vinyl magnesium bromide, etc., at a temperature of from $-78°$ C. to a boiling point of the solvent for 1 to 48 hours.

The reaction between Compound (VIIc) and Compound (VIII) can also be carried out in the co-presence of iodide such as sodium iodide, potassium iodide, etc.

METHOD 2-1

[Synthesis of Compound (Ib) in Compound (I), wherein $W^1$ is —NHCO— (part 1)]

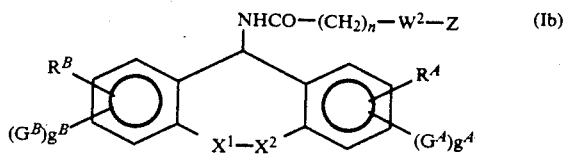

wherein $X^1$-$X^2$, $G^A$, $G^B$, $R^A$, $R^B$, $W^2$, Z, $g^A$, $g^B$ and n have the same significances as described above.

Compound (Ib) can be produced according to the following reaction steps.

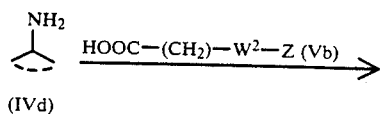

-continued $$\underset{(Ib)}{\triangle}\text{NHCO—(CH}_2)_n\text{—W}^2\text{—Z}$$

wherein $\triangle$, $W^2$, Z and n have the same significances as described above.

Compound (Ib) can be obtained by reacting Compound (IVd) or acid addition salts thereof with 1 to 5 molar equivalents of a carboxylic acid (Vb) or reactive derivatives thereof, either in an inert solvent such as methylene chloride, chloroform, etc., if necessary and desired, in the presence of a base such as pyridine, etc., or using an organic base itself such as pyridine as the solvent, between at 0° C. and a boiling point of the solvent for 1 to 48 hours.

Herein, the carboxylic acid reactive derivative include an acid halide (acid chloride, acid bromide, etc.), an acid anhydride (acid anhydride formed with a dehydrating and condensing agent such as N,N'-dicyclohexylcarbodiimide, etc., in the reaction system, commercially available acid anhydrides, etc.), an activated ester (p-nitrophenyl ester, N-oxysuccinimide ester), a mixed acid anhydride (monoethyl carbonate, monoisobutyl carbonate, etc.) and the like.

METHOD 2-2

[Synthesis of Compound (Ib) (part 2)]

Compound (Ib) can also be obtained from Compound (IVd) according to the following reaction steps.

$$\underset{(IVd)}{\triangle}\overset{NH_2}{\underset{}{|}}\xrightarrow{\text{Hal—CO—(CH}_2)_n\text{—Hal}}{(VIb)}$$

$$\underset{(VIId)}{\triangle}\overset{NHCO—(CH_2)_n—Hal}{\underset{}{|}}\xrightarrow{\text{H—W}^2\text{—Z}}{(VIII)}$$

$$\underset{(Ib)}{\triangle}\overset{NHCO—(CH_2)_n—W^2—Z}{\underset{}{|}}$$

wherein $\triangle$, $W^2$, Z, Hal and n have the same significances as described above.

Compound (VIId) can be obtained by reacting Compound (IVd) with 1 to 5 molar equivalents of an acid halide (VIb) in an inert solvent such as methylene chloride, chloroform, etc., if necessary and desired, in the presence of a base such as pyridine, etc., at a temperature of from 0° C. to room temperature for 1 to 24 hours.

The thus obtained Compound (VIId) can be led to Compound (Ib) in a manner similar to the conversion from Compound (VIIc) into Compound (Ia) in Method 1-2.

METHOD 3

[Synthesis of Compound (Ic) in Compound (I), wherein $W^1$ is =N—]

(structure Ic shown with $R^B$, $R^A$, $(G^B)_{g^B}$, $(G^A)_{g^A}$, $X^1$—$X^2$, and $(CH_2)_n$—$W^2$—Z substituent on =N—)

wherein $X^1$-$X^2$, $G^A$, $G^B$, $R^A$, $R^B$, $W^2$, Z, $g^A$, $g^B$ and n have the same significances as described above.

Compound (Ic) can be produced according to the following reaction steps.

$$\underset{(III)}{\triangle}\overset{O}{\underset{}{\|}}\xrightarrow{H_2N—(CH_2)_n—W^2—Z\ (Vc)}\underset{(Ic)}{\triangle}\overset{N—(CH_2)_n—W^2—Z}{\underset{}{\|}}$$

wherein $\triangle$, $W^2$, Z and n have the same significances as described above.

Compound (Ic) can be obtained by reacting Compound (III) with 1 to 10 molar equivalents of an amine (Vc) in an inert gas, for example, in the atmosphere of nitrogen, argon, etc., if necessary and desired, in the presence of a bulky organic base such as 2,6-lutidine, dicyclohexylmethylamine, etc. and 1 to 10 molar equivalents of Lewis acid such as titanium tetrachloride, in an inert solvent, for example, benzene, between at 0° C. and a boiling point of the solvent for 1 to 96 hours.

METHOD 4-1

[Synthesis of Compound (Id) in Compound (I), wherein $W^1$ is =CH— (part 1)]

(structure Id shown with $R^B$, $R^A$, $(G^B)_{g^B}$, $(G^A)_{g^A}$, $X^1$—$X^2$, and HC=C—$(CH_2)_n$—$W^2$—Z)

wherein $X^1$-$X^2$, $G^A$, $G^B$, $R^A$, $R^B$, $W^2$, Z, $g^A$, $g^B$ and n have the same significances as described above.

Compound (Id) can be produced according to the following reaction steps:

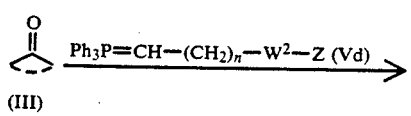

(III)

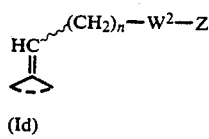

(Id)

wherein

, $W^2$, Z, Ph and n have the same significances as described above.

A phosphonium salt (Vf):

$$Ph_3P^{\ominus}CH_2-(CH_2)_n-W^2-Z \cdot Hal^{\oplus} \quad (Vf)$$

wherein $W^2$, Z, Hal, Ph and n have the same significances as described above, obtained by reacting triphenylphosphine ($Ph_3P$) with a halide [Hal—CH$_2$—(CH$_2$)$_n$—W$^2$—Z (Ve)] is firstly subjected to reaction in an inert solvent, for example, tetrahydrofuran, etc., in the presence of a molar equivalent of a base such as n-butyl lithium, etc., at a temperature of from 0° C. to room temperature to give an ylide (Vd).

Compound (Id) can be obtained by reacting 1 to 5 molar equivalents, based on Compound (III), of Compound (Vd), after or without isolation, with Compound (III) in an inert solvent, for example, tetrahydrofuran, etc., at a temperature of from 0° C. to a boiling point of the solvent.

METHOD 4-2

[Synthesis of Compound (Id) (part 2)]

Compound (Id) can also produced from Compound (III) according to the following reaction steps.

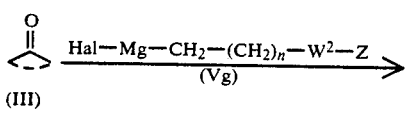

(III)

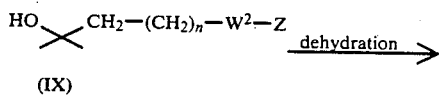

(IX)

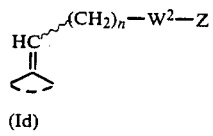

(Id)

wherein

, $W^2$, Z, Hal and n have the same significances as described above.

An alcohol (IX) can be obtained by reacting 1 to 5 molar equivalents of Grignard reagent (Vg) with Compound (III) in an inert solvent such as tetrahydrofuran, diethyl ether, etc., at a temperature of from 0° C. to room temperature for 1 to 48 hours.

Compound (Vg) is formed by reacting the corresponding Compound (Ve) with 0.5 to 2 molar equivalents of magnesium in an inert solvent such as tetrahydrofuran, diethyl ether, etc., if necessary, in the presence of a trace amount of iodine, at a temperature of from 0° C. to a boiling point of the solvent for 0.5 to 12 hours. The Grignard reagent formed is generally used for the next reaction as it is, without isolating the same.

The thus obtained Compound (IX) is subjected to dehydration to give Compound (Id). For the dehydration, there are used a method which comprises the reaction in an inert solvent such as dioxane, etc., in the presence of an acid, for example, p-toluenesulfonic acid, between at room temperature and a boiling point of the solvent for 1 to 12 hours; a method which comprises reaction with a halogenating agent such as thionyl chloride, etc. in an organic base such as pyridine at a temperature of from 0° C. to room temperature for 1 to 12 hours, and the like.

METHOD 4-3

[Synthesis of Compound (Id) (part 3)]

Firstly, the carbonyl group of Compound (III) is converted into Compound (VIIf) according to the following reaction steps.

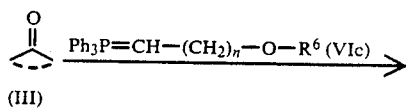

(III)

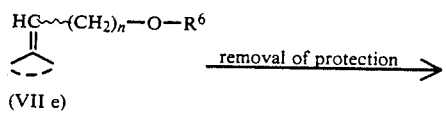

(VII e)

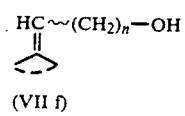

(VII f)

wherein

,

Ph and n have the same significances as described above; and $R^6$ represents a protective group of hydroxy.

Herein, as the protective group of hydroxy, groups generally used as protective groups for alcoholic hydroxy can be used and, specifically, tetrahydropyranyl or the like is preferably used.

An ylide (VIc) in which the hydroxy is firstly protected with a suitable protective group (for example, tetrahydropyranyl, etc.) is formed in an inert solvent, e.g., tetrahydrofuran [cf., J. Org. Chem., 44, 3760 (1979)].

Then, the formed ylide (VIc) is reacted with 0.2 to 1 molar equivalent of Compound (III) at a temperature of from −78° C. to a boiling point of the solvent for 1 to 48 hours to give Compound (VIIe).

Compound (VIIe) can be converted into Compound (VIIf) by removing the protective group. The removal of protective group can be conducted in a conventional manner; in the case of using, for example, tetrahydropyranyl as a protective group, Compound (VIIe) is treated with an acid catalyst such a p-toluenesulfonic acid, hydrochloric acid, etc. in a suitable hydrated solvent such as hydrated dioxane, hydrated tetrahydrofuran, etc., at a temperature of from 0° C. to a boiling point of the solvent for 1 to 24 hours to give Compound (VIIf).

Compound (VIIf) can be led to Compound (Id) via Compound (VIIg) or (VIIh) according to the following reaction steps.

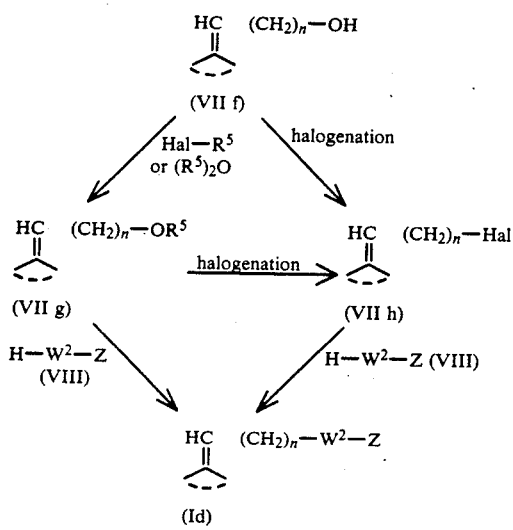

wherein

$W^2$, $Z$, $R^5$, Hal and n have the same significances as described above.

The reaction can be performed in a manner similar to the method for leading Compound (VIIa) to Compound (Ia) described in Method 1-2.

METHOD 4-4

[Synthesis of Compound (Id-1) in Compound (Id), wherein n is 1]

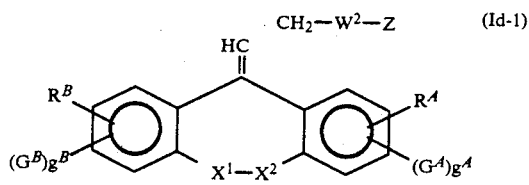

wherein $X^1$-$X^2$, $G^A$, $G^B$, $R^A$, $R^B$, $W^2$, $Z$, $g^A$ and $g^B$ have the same significances as described above.

Compound (Id-1) can be prepared according to the following reaction steps.

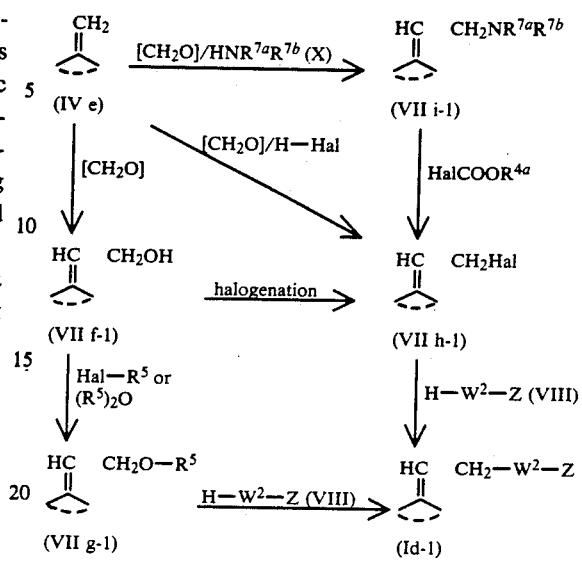

wherein

$W^2$, $Z$, $R^5$ and Hal have the same significances as described above, $R^{4a}$ has the same significance for $R^4$ as described above; [CH$_2$O] represents formaldehyde and/or a polymer thereof; and $R^{7a}$ and $R^{7b}$, which may be the same or different, each represents lower alkyl or may be combined to nitrogen adjacent thereto to form a heterocyclic ring.

Herein, the lower alkyl in the definitions of $R^{7a}$ and $R^{7b}$ has the same significances for the lower alkyl in formula (I). As the heterocyclic ring formed by $R^{7a}$ and $R^{7b}$, mention may be made of pyrrolidine, piperidine, N-methylpiperazine, morpholine, thiomorpholine, N-methylhomopiperazine and the like.

Compound (IVe) is reacted with 1 to 10 molar equivalents of formaldehyde and/or a formaldehyde polymer, for example, paraformaldehyde, in a hydrohalogenic acid, preferably hydrochloric acid or in an inert solvent, for example, dioxane, saturated with hydrogen chloride and, if necessary and desired, in the presence of a strong acid such as sulfuric acid or trifluoroacetic acid, at a temperature of from room temperature to a boiling point of the solvent, for 1 to 24 hours to give Compound (VIIh-1).

Compound (VIIf-1) can be obtained under almost the same conditions as described above except that no hydrohalogenic acid is added.

Furthermore, Compound (VIIh-1) can also be obtained as follows. That is, Compound (IVe) is reacted with 1 to 2 molar equivalents of formaldehyde and/or a polymer thereof, for example, paraformaldehyde, 1 to 3 molar equivalents of a secondary amine (X) and trifluoroacetic acid, in an inert solvent such as methylene chloride, chloroform, dichloroethane, tetrachloroethane, etc., if necessary and desired, in the presence of acetic acid, between at room temperature and a boiling point of the solvent, for 1 to 48 hours to give Compound (VIIi-1) or an acid addition salt thereof. Compound (VIIi-1) can be led to Compound (VIIh-1) by reacting Compound (VIIi-1) with 1 to 10 molar equivalents of a halocarbonate, preferably ethyl chloroformate if necessary and desired, in the presence of a base such as triethylamine, sodium acetate, etc. in an inert solvent such as methylene chloride, chloroform, dichloroethane, tetrachloroethane, etc., between at 0° C. and a boiling point of the solvent for 1 to 48 hours.

Furthermore, Compound (VIIh-1) can also be obtained according to the following reaction steps.

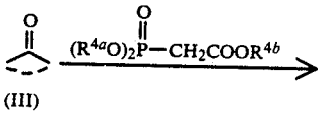
(III)

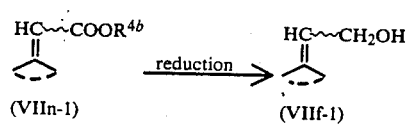
(VIIn-1)    (VIIf-1)

wherein

has the same significance as described above, and each of $R^{4a}$ and $R^{4b}$ independently has the same significances for $R^4$ as described above.

Compound (III) is reacted with 1 to 10 molar equivalents of Horner-Emmons reagent (VIf) in an inert solvent such as tetrahydrofuran, etc. at a temperature of from $-78°$ C. to a boiling point of the solvent for 1 to 24 hours, if necessary and desired, in the presence of 1 to 10 molar equivalents of a base, preferably sodium hydride, potassium tert-butoxide, etc. to give Compound (VIIn-1).

Then, the alkoxycarbonyl of the obtained Compound (VIIn-1) is selectively reduced by a suitable reduction method to give Compound (VIIf-1). Preferred reduction is performed either by treating Compound (VIIn-1) with 1 to 10 molar equivalents of lithium aluminum hydride as the reducing agent in an inert solvent such as diethyl ether, etc. at a temperature of from $-78°$ C. to room temperature for 10 minutes to 24 hours, or by treating Compound (VIIn-1) with 1 to 10 molar equivalents of diisobutyl hydrated aluminum as the reducing agent in an inert solvent such as tetrahydrofuran, etc. at a temperature of from $-100°$ C. to room temperature for 10 minutes to 24 hours.

The thus obtained Compounds (VIIf-1) and (VIIh-1) can be converted into Compound (Id-1) according to the method for synthesizing Compound (Id) from corresponding Compounds (VIIf) and (VIIh) described in Method 4-3.

METHOD 5-1

[Synthesis of Compound (Ie) in Compound (I), wherein $W^1$ is —CH$_2$— (part 1)]

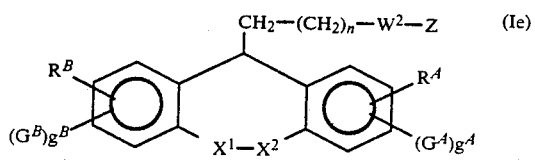

wherein $X^1$-$X^2$, $G^A$, $G^B$, $R^A$, $R^B$, $W^2$, $Z$, $g^A$, $g^B$ and n have the same significances as described above.

Compound (Ie) can be obtained according to the following reaction step.

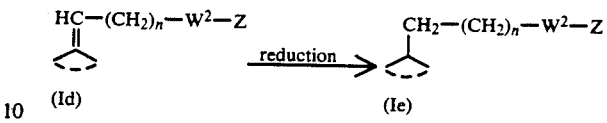
(Id)    (Ie)

wherein

$W^2$, $Z$ and n have the same significances as described above.

Compound (Ie) can be obtained by hydrogenating Compound (Id) wherein $W^1$ is =CH—, in the presence of an appropriate catalyst, for example, palladium-carbon, platinum oxide, Raney nickel, nickel boride or cobalt boride, etc., if necessary and desired, in the co-presence of an acid such as hydrochloric acid, in an inert solvent, for example, ethanol, acetic acid, etc. between at 0° C. and a boiling point of the solvent for 1 to 48 hours, under normal pressure to under pressure.

METHOD 5-2

[Synthesis of Compound (Ie) (part 2)]

Compound (Ie) can also be prepared from Compound (IVc) according to the following reaction steps.

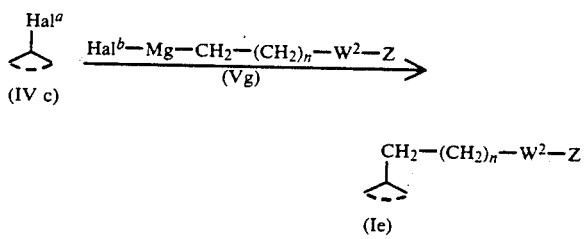
(IV c)

(Ie)

wherein

$W^2$, $Z$ and n have the same significances as described above; and each of $Hal^a$ and $Hal^b$ independently has the same significances for Hal as described above.

The reaction is carried out under almost the same conditions as in the Grignard reaction for leading Compound (III) to Compound (IX) described in Method 4-2.

METHOD 5-3

[Synthesis of Compound (Ie) (part 3)]

Firstly, Compound (IVc) is converted into Compound (VIIk) according to the following reaction steps.

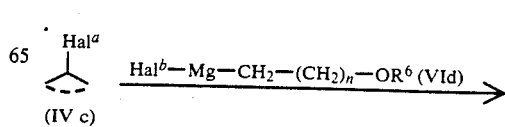
(IV c)

-continued

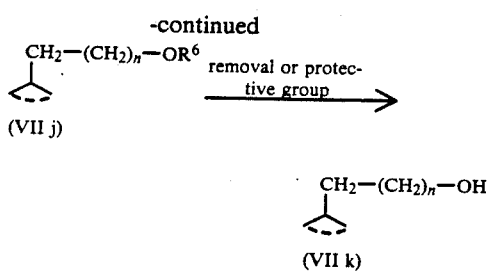

wherein

Hal$^a$, Hal$^b$, R$^6$ and n have the same significances as described above.

Compound (VIIj) is obtained by reacting Grignard reagent (VId) wherein the hydroxy is protected with an appropriate protective group (for example, tetrahydropyranyl, etc.) with 0.1 to 1 molar equivalent of Compound (IVc) at a temperature of −78° C. to a boiling point of the solvent for 1 to 24 hours in an inert solvent such as tetrahydrofuran, diethyl ether, etc.

Compound (VId) is produced from the corresponding Compound (VIe):

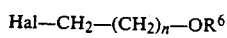 (VIe)

wherein R$^6$, Hal and n have the same significances as described above, in a manner similar to the preparation of Grignard reagent (Vg) described in Method 4-2.

Compound (VIIk) can be obtained by removing the protective group in Compound (VIIj) in a conventional manner, for example, Method 4-3.

Compound (VIIk) can be led to Compound (Ie) via Compound (VII l) or (VII m) according to the following reaction steps.

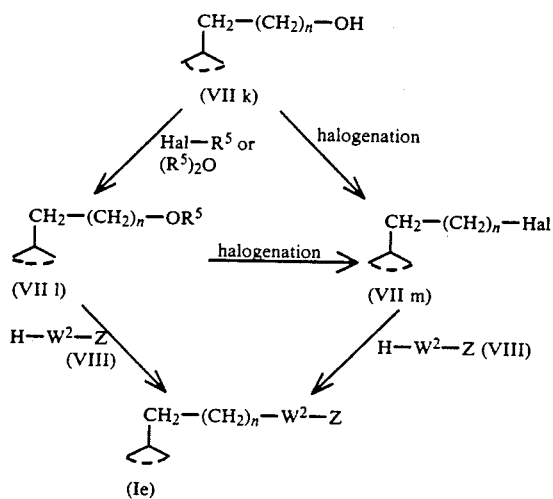

wherein

W$^2$, Z, R$^5$, Hal and n have the same significances as described above.

The reaction can be performed in a manner similar to the method for leading Compound (VIIa) to Compound (Ia) described in Method 1-2.

METHOD 5-4

[Synthesis of Compound (Ie-1) in Compound (Ie) wherein n is 1]

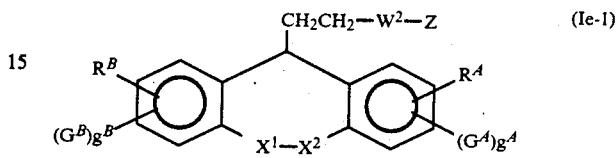

wherein X$^1$-X$^2$, G$^A$, G$^B$, R$^A$, R$^B$, W$^2$, Z, g$^A$ and g$^B$ have the same significances as described above.

Compound (Ie-1) can be obtained according to the following reaction steps.

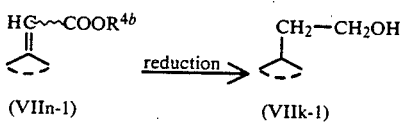

wherein

and R$^{4b}$ have the same significances as described above.

Compound (VIIn-1) obtained by Method 4-4 is reduced to give Compound (VIIk-1). For the reduction, the reaction is preferably carried out either in an inert solvent such as tetrahydrofuran, diethyl ether, etc. at a temperature of from 0° C. to a boiling point of the solvent for 1 to 24 hours, using, for example, 1 to 10 molar equivalents, based on Compound (VIIn-1), of a reducing agent such as lithium aluminum hydride, or by hydrogenating Compound (VIIn-1) in the presence of a catalyst, for example, nickel boride or cobalt boride, etc.

The thus obtained Compound (VIIk-1) can be led to Compound (Ie-1) in a manner similar to Method 5-3 for synthesizing Compound (Ie) from Compound (VIIk).

METHOD 6

[Synthesis of Compound (I-1) in Compound (I), wherein W$^2$ is single bond and Z is substituted or unsubstituted benzimidazolyl (compound having the formula (b) wherein a is

b is =CH—, C is =N—, each of d¹, d², d³ and d⁴ is =CH—)]

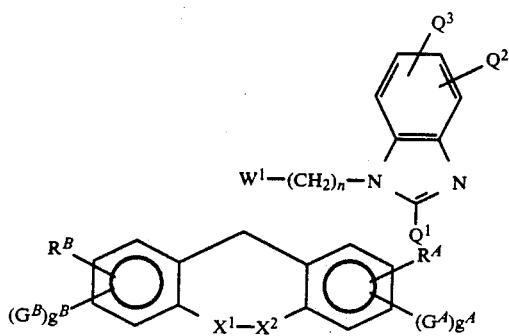
(I-1)

wherein X¹-X², $G^A$, $G^B$, $R^A$, $R^B$, $W^1$, $Q^1$, $Q^2$, $Q^3$, $g^A$, $g^B$ and n have the same significances as described above.

Compound (I-1a) [Compound (I-1) wherein $Q^1$ is hydrogen] can be obtained according to the following reaction steps.

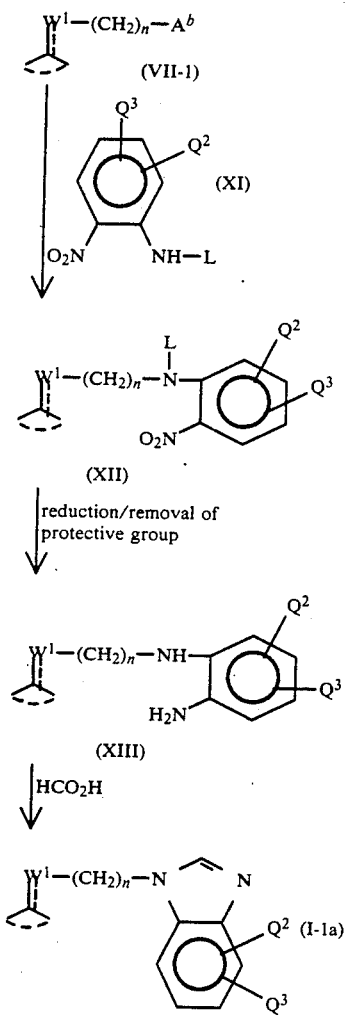

wherein $A^b$ represents $OR^5$ or Hal; L represents a protective group for amino; and,

, $W^1$, $Q^2$, $Q^3$, $R^5$, Hal and n have the same significances as described above.

Herein, the protective group denoted by L includes an acyl group such as acetyl, trifluoroacetyl, etc., a sulfonyl group such as methanesulfonyl, p-toluenesulfonyl, and the like.

Firstly, Compound (VII-1) [Compounds (VIIb), (VIIc)), (VIId), (VIIg), (VIIh), (VIII), (VIIm), etc.] is reacted with 1 to 10 molar equivalents of Compound (XI) in an inert solvent, for example, tetrahydrofuran, N,N-dimethylformamide or the like, in the presence of a base such as sodium hydride, triethylamine etc. between at −78° C. and a boiling point of the solvent for 1 to 48 hours to give Compound (XII).

The thus obtained Compound (XII) is led to Compound (I-1a) via an o-phenylenediamine derivative (XIII). Compound (XIII) can be provided for the following reaction without isolation. The reduction of nitro and hydrolysis (removal of the protective group) may be performed simultaneously or non-preferentially and sequentially; alternatively, Compound (I-1a) can also be obtained by performing reduction of nitro and cyclization simultaneously after hydrolysis.

The reduction of nitro into amino in Compound (XII) can be performed by hydrogenation in an inert solvent such as ethanol, etc. at a temperature of from room temperature to 200° C. under normal pressure to under pressure, in the presence of a catalyst such as palladium-carbon, etc. Alternatively, the reduction may be performed by treatment with a metal such as zinc, tin, iron, etc. or salts thereof and a largely excessive acid such as hydrochloric acid, sulfuric acid, etc. at a temperature of from room temperature to a boiling point of the acid used for 1 to 24 hours. The reduction using zinc, etc. may also be practiced under basic conditions using an aqueous sodium hydroxide solution instead of the acid.

Furthermore, Compound (I-1a) which is simultaneously cyclized may also be prepared by previously removing the protective group through hydrolysis and then performing the reduction in the co-presence of a molar equivalent of to a largely excessive of formic acid.

The protective group L in Compound (XII) can be removed either by reaction in the presence of an acid such as hydrochloric acid, sulfuric acid, p-toluenesulfonic acid, etc. in water or a hydrated solvent such as hydrated dioxane, etc., at a temperature of from room temperature to a boiling point of the solvent for 1 to 24 hours, or by reaction in the presence of a base such as sodium hydroxide, potassium hydroxide, etc. in an inert solvent such as methanol, hydrated dioxane, etc., at a temperature of from room temperature to a boiling point of the solvent for 1 to 24 hours.

Furthermore, the cyclization from the o-phenylenediamine derivative (XIII) to Compound (I-1a) can be effected by reaction in the presence of an equimolar amount of to a largely excessive formic acid in an inert solvent such as water, dioxane, etc. or in the absence of any solvent, preferably in a solvent mixture of formic acid and an aqueous hydrochloric acid solution, if necessary and desired, in the presence of an acid such as hydrochloric acid, sulfuric acid, etc., at a temperature of from room temperature to a boiling point of the solvent for 1 to 24 hours.

The above cyclization is described by referring to Compound (I-1a) in Compound (I-1) wherein $Q^1$ is hydrogen; compounds having substituents other than $Q^1$ being hydrogen can also be synthesized in a manner similar to the method of converting the o-phenylenediamine derivative into benzimidazole derivatives [cf., for example, Prest: Heterocyclic Compounds, 40, Inter Science (1981)]. For example, where methyl is desired for $Q^1$, acetic acid is used in place of formic acid and the procedure can be performed in a similar manner.

In case that an asymmetrically substituted benzimidazole (XIV) is used when applying Method 1-2, 2-2, 4-3, 4-4, 5-3 or the like for the production of Compound (I-1), a mixture of 2 positional isomers (I-1-1) and (I-1-2) is generally given, as shown in the following reaction steps.

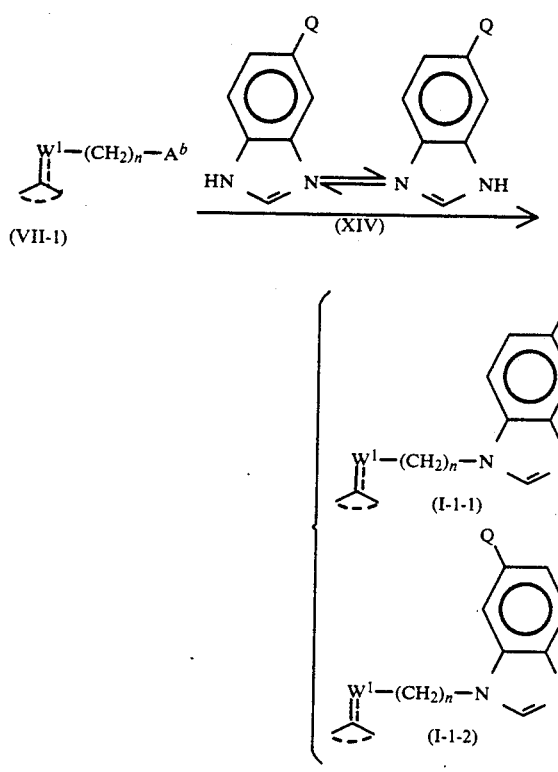

wherein Q represents the substituents other than hydrogen defined for $Q^2$ or $Q^3$; and

$W^1$, $A^b$ and n have the same significances as described above.

These isomers may be isolated in a conventional manner used in organic synthesis chemistry, for example, recrystallization, columm chromatography, etc. but may be sometimes isolated with difficulty. Accordingly, where the isolation is difficult or either isomer may be wished to obtain selectively, these methods are not always appropriate. Method 6 provides effective means in such a case.

METHOD 7

[Synthesis of Compound (I-2a) in Compound (I), wherein Z is $Z^a$]

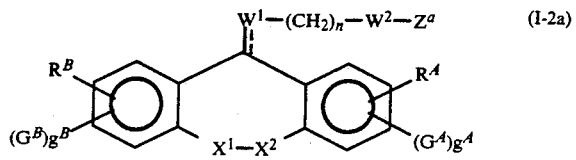

wherein $Z^a$ represents a group wherein substituent(s) $Q^1$, $Q^2$ and/or $Q^3$ are/is $-OR^{2a}$, $-SR^{2a}$, $-NHR^{2a}$ or $-N(R^{2a})_2$; $R^{2a}$ represents alkyl or benzyl in the definitions for $R^2$; and, , $X^1$-$X^2$, $G^A$, $G^B$, $R^A$, $R^B$, $W^1$, $W^2$, n, $g^A$ and $g^B$ have the same significances as described above.

Compound (I-2a) can be obtained according to the following reaction steps.

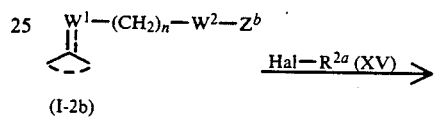

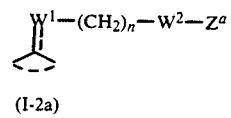

wherein $Z^b$ represents a group wherein substituent(s) $Q^1$, $Q^2$ and/or $Q^3$ are/is $-OH$, $-SH$, $-NH_2$; and, $W^1$, $W^2$, $Z^a$, $R^{2a}$, Hal and n have the same significances as described above.

Compound (I-2a) can be obtained by reacting Compound (I-2b) [compounds of Compound (I) wherein Z is $Z^b$] with 1 to 10 molar equivalents of Compound (XV) in an inert solvent, for example, N,N-dimethylformamide or the like, if necessary and desired, in the presence of a base such as pyridine, or using as the solvent an organic base itself such as pyridine, etc. at a temperature of from 0° C. to a boiling point of the solvent for 1 to 48 hours.

METHOD 8-1

[Synthesis of Compound (I-3) in Compound (I), wherein either $R^A$ or $R^B$ is $-Y-COOH$]

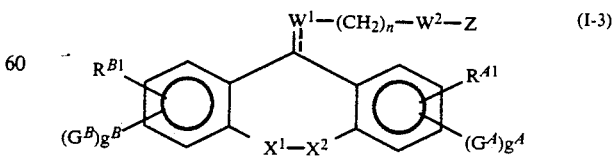

wherein one of $R^{A1}$ and $R^{B1}$ represents $-Y-COOH$ and the other represents a hydrogen atom; and $X^1$-$X^2$, $G^A$, $G^B$, $W^1$, $W^2$, Z, Y, $g^A$, $g^B$ and n have the same significances as described above.

Compound (I-3) can be obtained according to the following reaction steps.

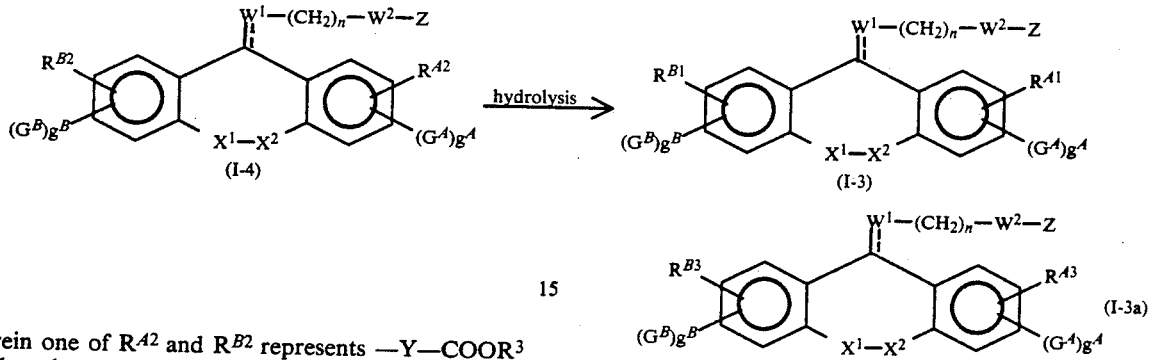

wherein one of $R^{A2}$ and $R^{B2}$ represents —Y—COOR$^3$ and the other represents a hydrogen atom; ____, $X^1$-$X^2$, $G^A$, $G^B$, $W^1$, $W^2$, Z, Y, $R^{A1}$, $R^{B1}$, $g^A$, $g^B$ and n have the same significances as described above and $R^3$ represents lower alkyl.

Herein, the lower alkyl denoted by $R^3$ has the same significance for $R^{1a}$ as described above.

Compound (I-3) can be obtained by subjecting Compound (I-4)[alkyl carboxylate in Compound (I) wherein either $R^A$ or $R^B$ is —Y—COOR$^3$] synthesized according to Methods 1 to 7 to an appropriate hydrolysis method, for example, by reaction with an equimolar amount of to a largely excessive sodium hydroxide or potassium hydroxide, etc. in a solvent mixture of a lower alcohol such as methanol, ethanol, etc. and water, between at room temperature and a boiling point of the solvent, for 1 to 48 hours.

METHOD 8-2

[Synthesis of Compound (I-3a) in Compound (I-3), wherein Y is single bond]

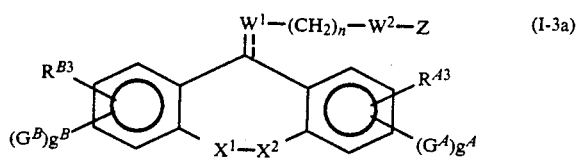

wherein one of $R^{A3}$ and $R^{B3}$ represents —COOH and the other represents a hydrogen atom; and____, $X^1$-$X^2$, $G^A$, $G^B$, $W^1$, $W^2$, Z, $g^A$, $g^B$ and n have the same significances as described above.

Compound (I-3a) can be obtained according to the following reaction steps.

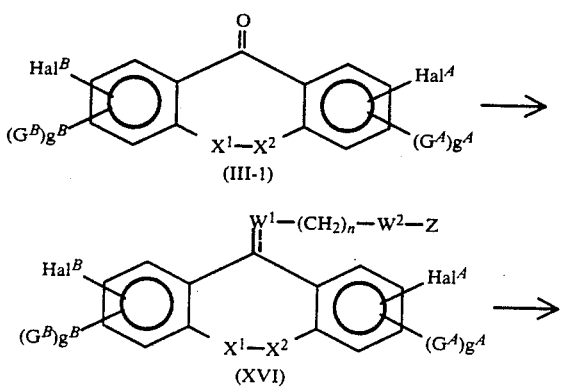

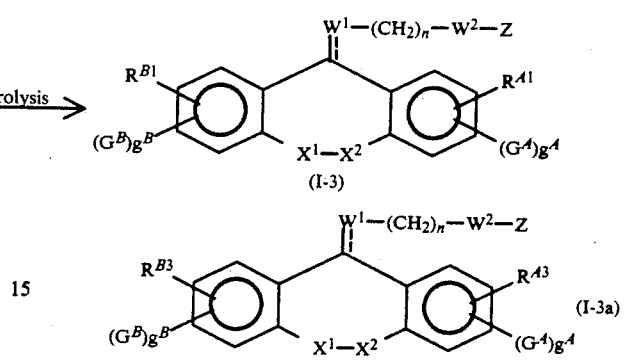

wherein one of Hal$^A$ and Hal$^B$ represents Hal and the other represents a hydrogen atom; and ____, $X^1$-$X^2$, $G^A$, $G^B$, $W^1$, $W^2$, Z, $R^{A3}$, $R^{B3}$, Hal, $g^A$, $g^B$ and n have the same significances as described above.

Compound (I-3a) can be obtained by carboxylating Compound (XVI) synthesized from Compound (III-1) [Compound having at least one halogen as the substituent on the benzene ring in Compound (III)] in a manner similar to Methods 1 to 7.

Carboxylation can be performed by reacting, for example, Compound (XVI) with a molar equivalent of a metallizing agent, e.g., n-butyl lithium, in an inert solvent such as tetrahydrofuran, etc., at a temperature of from $-78°$ C. to room temperature, for 10 minutes to 12 hours followed by reacting the resulting reaction mixture with an equimolar amount of to a largely excessive amount of carbon dioxide at a temperature of from $-78°$ C. to room temperature, for 10 minutes to 12 hours. Alternatively, Compound (I-3a) can also be obtained by preparing the corresponding Grignard reagent from Compound (XVI) and magnesium in an inert solvent such as diethyl ether, etc. in a manner similar to Method 4-2 and reacting the reagent with carbon dioxide, and the like method.

METHOD 9

In the methods for production shown by Methods 1 through 8, where groups defined in Compound (I) change under conditions of the Methods or are inappropriate for practicing the method, the groups may be subjected to conventional means used in organic synthesis chemistry, for example, means for protecting functional groups, removing protection, etc. [for example, cf., Green, Protective Groups in Organic Synthesis, John Wiley & Sons Incorporated (1981)], methods for oxidation, reduction, hydrolysis, etc. [for example, cf., SHIN-JIKKEN KAGAKU KOZA, vols. 14 & 15, Maruzen (1977)].

For example, in case that —COOH is desired as the functional group, 4,4-dimethyloxazoline, etc. are preferably used as a protective group for —COOH (for example, Japanese Published Unexamined Patent Application No. 10784/1988) in the method in which the corresponding ester is hydrolyzed (cf., Method 8-1 described above), in the reaction using a Grignard reagent (cf., for example, Methods 4-2, 5-2, 5-3 and the like), in the reaction using reduction (for example, Methods 4-4, 5-1, 5-4 and the like) and in the reaction using an organic metal reagent (for example, Method 1-2, etc.). Furthermore, a desired compound can be obtained by hydrolyzing, i.e. removing a protective group in a compound similarly obtained by Methods 1 through 7, etc. in which either $R^A$ or $R^B$ is —Y'—$CH_2OR^8$ [wherein Y' represents a group obtained by removing $CH_2$ from Y and $R^8$ represents a protecting group for hydroxy (e.g., acetyl group, tetrahydropyranyl, etc.)] to convert —Y'—$CH_2OR^8$ into —Y'—$CH_2OH$ and oxidizing the compound.

The intermediates and objective compounds in the respective methods described above can be isolated and purified by purification methods conventionally used in organic synthesis chemistry, for example, filtration, extraction, washing, drying, concentration, recrystallization, various column chromatographies, etc. Further the intermediates may also be provided in the subsequent reaction, without being particularly purified.

In Compound (I) obtained by the foregoing methods, compounds wherein $W^1$ is =CH— or =N— include geometrical isomers of E-form and Z-form with respect to stereochemistry. In general, the methods described above often give a mixture of these isomers. Isolation and purification of these isomers can be made in a conventional manner used in organic synthesis chemistry, for example, by column chromatography, recrystallization, etc.

It is also possible to isolate the isomers at stages of intermediates (VIIe to VIIi), by the various methods described above.

Further, if desired, E- and Z-forms may be isomerized from each other. This can be made by treating each isomer in a reflux of, e.g., acetic acid, for 1 to 24 hours, in the presence of an appropriate acid catalyst such as p-toluenesulfonic acid, etc.

In the present invention, Compound (I) includes not only the E/Z isomers described above but also all possible stereoisomers and a mixture thereof.

In case that salts of Compound (I) are desired to obtain, when Compound (I) is obtained in the form of a salt, Compound (I) may be purified as it is. Further in case that Compound (I) is obtained in a free form, salts may be formed in a conventional manner.

Furthermore, Compound (I) and pharmaceutically acceptable salts thereof may also be present in the form of addition products to water or various solvents; these adducts are also included in the present invention.

Specific examples of Compound (I) obtained by various methods are shown in Table 1.

Numbering of substitution positions in Table 1 and Table 6 later described does not necessarily harmonize with the correct nomenclature [cf. (NOTE) below]; but for purpose of simplicity, numbering of the substitution positions is systematically made as illustrated below.

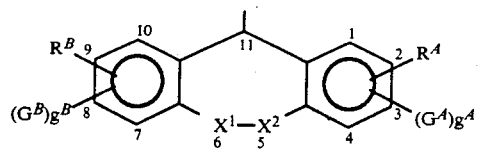

(NOTE)

In cycloheptene derivatives (wherein $X-X^2$ is —$CH_2$—$CH_2$— or —CH=CH—), despite the positional number in the general formula above, for example, a substituent on the carbon at the 2-position in the formula above is correctly given as a substituent at the 3-position. However, in the tables, following the positional numbering in the formula described above, —COOH on the carbon at the 2-position is indicated to be 2-COOH (correctly 3-COOH).

TABLE 1

| $X^1$—$X^2$ | $(G^A)g^A/(G^B)g^B$ | —$W^1$—$(CH_2)_n$—$W^2$—Z | $R^A/R^B$ | Compound No. |
|---|---|---|---|---|
| —$CH_2O$— | H | —NH—⟨pyridine⟩ | 2-$COOC_2H_5$ | 1 a |
|  |  |  | 2-COOH | 1 b |
| " | " | " | 2-$CH_2COOCH_3$ | 2 a |
|  |  |  | 2-$CH_2COOH$ | 2 b |
| " | " | " | 2-$CH(CH_3)COOCH_3$ | 3 a |
| " | " | " | 2-$CH(CH_3)COOH$ | 3 b |
| " | " | " | 2-$C(CH_3)_2COOCH_3$ | 4 a |
| " | " | " | 2-$C(CH_3)_2COOCH_3$ | 4 b |
| " | " | " | 2-$CH_2CH_2COOCH_3$ | 5 a |
| " | " | " | 2-$CH_2CH_2COOH$ | 5 b |
| " | " | " | 2-CH=$CHCOOCH_3$ | 6 a |
|  |  |  | 2-CH=CHCOOH | 6 b |
| " | " | —NH—⟨pyridine-N⟩ | 2-$COOC_2H_5$ | 7 a |
|  |  |  | 2-COOH | 7 b |
| " | " | —S—⟨pyridine⟩ | 2-$COOCH_3$ | 8 a |
|  |  |  | 2-COOH | 8 b |
| " | " | —NH—$CH_2$—⟨pyridine⟩ | 2-$COOC_2H_5$ | 9 a |
|  |  |  | 2-$COO(CH_2)_3CH_3$ | 9 b |
|  |  |  | 2-COOH | 9 c |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | " | 2-CH$_2$COOCH$_3$ | 10 a |
|   |   |   | 2-CH$_2$COOH | 10 b |
| —CH$_2$O— | H | 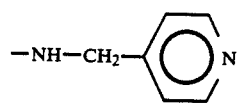 —NH—CH$_2$— | 2-COOC$_2$H$_5$ | 11 a |
|   |   |   | 2-COOH | 11 b |
| " | " | 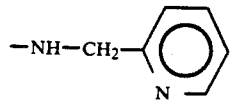 —NH—CH$_2$— | 2-COOC$_2$H$_5$ | 12 a |
|   |   |   | 2-COOH | 12 b |
| " | " | 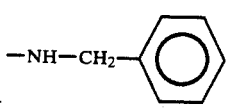 —NH—CH$_2$— | 2-COOC$_2$H$_5$ | 13 a |
|   |   |   | 2-COOH | 13 b |
| " | " | 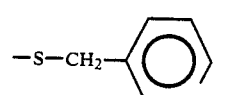 —S—CH$_2$— | 2-COOCH$_3$ | 14 a |
|   |   |   | 2-COOH | 14 b |
| " | " | " | 3-COOCH$_3$ | 15 a |
| " | " | " | 3-COOH | 15 b |
| " | " | " | 4-COOCH$_3$ | 16 a |
| " | " | " | 4-COOH | 16 b |
| " | " | " | 9-COOCH$_3$ | 17 a |
| " | 9-Br | " | 9-COOH | 17 b |
|   |   |   | 2-COOCH$_3$ | 18 a |
|   |   |   | 2-COOH | 18 b |
| " | H | 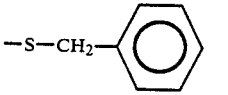 —S—CH$_2$— | 2-COOCH$_3$ | 19 a |
|   |   |   | 2-COOH | 19 b |
| " | " | " | 2-CH$_2$COOCH$_3$ | 20 a |
|   |   |   | 2-CH$_2$COOH | 20 b |
| " | " | 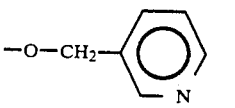 —O—CH$_2$— | 2-COOCH$_3$ | 21 a |
|   |   |   | 2-COOH | 21 b |
| —CH$_2$O— | H | 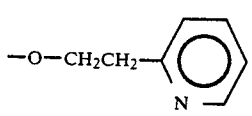 —O—CH$_2$CH$_2$— | 2-COOCH$_3$ | 22 a |
|   |   |   | 2-COOH | 22 b |
| " | " | 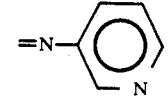 =N— | 2-COOCH$_3$ | 23 a |
|   |   |   | 2-COOH | 23 b |
| " | " | " | 2-CH$_2$COOCH$_3$ | 24 a |
|   |   |   | 2-CH$_2$COOH | 24 b |
| " | " | 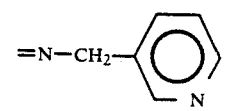 =N—CH$_2$— | 2-COOCH$_3$ | 25 a |
|   |   |   | 2-COOH | 25 b |
| " | " | 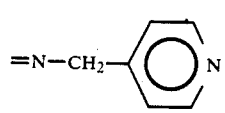 =N—CH$_2$— | 2-COOCH$_3$ | 26 a |
|   |   |   | 2-COOH | 26 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | 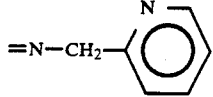 | 2-COOCH$_3$<br>2-COOH | 27 a<br>27 b |
| " | " | 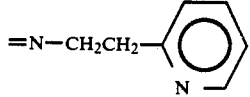 | 2-COOCH$_3$<br>2-COOH | 28 a<br>28 b |
| " | " | 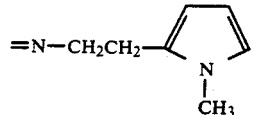 | 2-COOCH$_3$<br>2-COOH | 29 a<br>29 b |
| " | " | 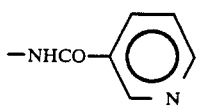 | 2-COOCH$_3$<br>2-COOH | 30 a<br>30 b |
| " | " | 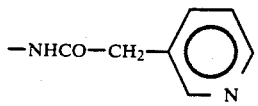 | 2-COOCH$_3$<br>2-COOH | 31 a<br>31 b |
| —CH$_2$O— | H | 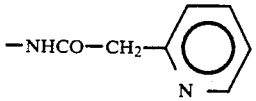 | 2-COOCH$_3$<br>2-COOH | 32 a<br>32 b |
| " | " | 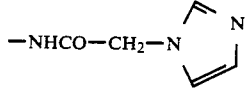 | 2-COOCH$_3$<br>2-COOH | 33 a<br>33 b |
| " | " | 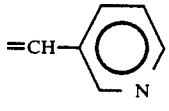 | 2-COOCH$_3$<br>2-COOH | 34 a<br>34 b |
| " | " | " | 2-CH$_2$COOCH$_3$<br>2-CH$_2$COOH | 35 a<br>35 b |
| " | " | 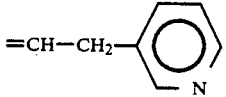 | 2-COOCH$_3$<br>2-COOH | 36 a<br>36 b |
| " | " | 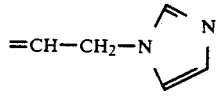 | 2-COOCH$_3$<br>2-COOH | 37 a<br>37 b |
| " | " | 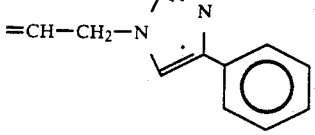 | 2-COOCH$_3$<br>2-COOH | 38 a<br>38 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | =CH—CH$_2$—N(imidazole with phenyl) | 2-COOCH$_3$<br>2-COOH | 39 a<br>39 b |
| " | " | —CH$_2$—CH$_2$—(3-pyridyl) | 2-COOCH$_3$<br>2-COOH | 40 a<br>40 b |
| —CH$_2$O— | H | =CH—CH$_2$—N(benzimidazol-1-yl) | 2-COOCH$_3$<br>2-COOH | 41 a<br>41 b |
| " | " | " | 9-COOCH$_3$<br>9-COOH | 42 a<br>42 b |
| " | 9-Br | " | 2-COOCH$_3$<br>2-COOH | 43 a<br>43 b |
| " | 9-OCH$_3$ | " | 2-COOCH$_3$<br>2-COOH | 44 a<br>44 b |
| " | H | —S—CH$_2$CH$_2$—N(benzimidazol-1-yl) | 2-COOCH$_3$<br>2-COOH | 45 a<br>45 b |
| " | " | =CHCH$_2$CH$_2$—N(benzimidazol-1-yl) | 2-COOCH$_3$<br>2-COOH | 46 a<br>46 b |
| " | " | =CH—CH$_2$—N(5-methylbenzimidazol-1-yl) | 2-COOCH$_3$<br>2-COOH | 47 a<br>47 b |
| " | " | =CH—CH$_2$—N(4-methylbenzimidazol-1-yl) | 2-COOCH$_3$<br>2-COOH | 48 a<br>48 b |

TABLE 1-continued
| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| $-CH_2O-$ | H | 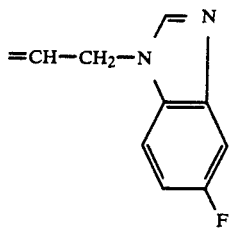 | 2-COOCH$_3$<br>2-COOH | 49 a<br>49 b |
| " | " | 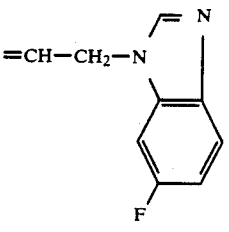 | 2-COOCH$_3$<br>2-COOH | 50 a<br>50 b |
| " | " | 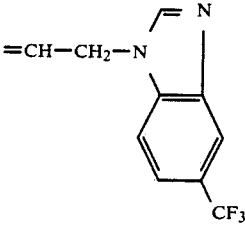 | 2-COOCH$_3$<br>2-COOH | 51 a<br>51 b |
| " | ". | 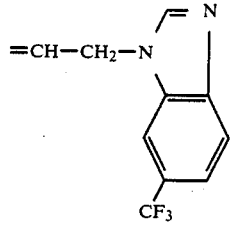 | 2-COOCH$_3$<br>2-COOH | 52 a<br>52 b |
| " | " | 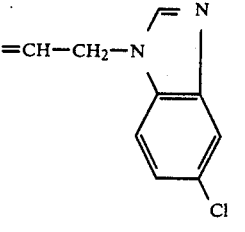 | 2-COOCH$_3$<br>2-COOH | 53 a<br>53 b |
| " | " | 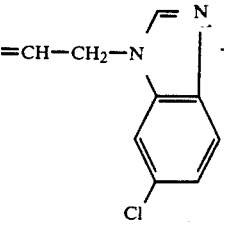 | 2-COOCH$_3$<br>2-COOH | 54 a<br>54 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | =CH—CH₂—N(CH=N)—C₆H₃(NO₂) (2-NO₂ para to N) | 2-COOCH₃<br>2-COOH | 55 a<br>55 b |
| —CH₂O— | H | =CH—CH₂—N(CH=N)—C₆H₃(NO₂) | 2-COOCH₃<br>2-COOH | 56 a<br>56 b |
| " | " | =CH—CH₂—N(CH=N)—C₆H₃(CN) | 2-COOCH₃<br>2-COOH | 57 a<br>57 b |
| " | " | =CH—CH₂—N(CH=N)—C₆H₃(CN) | 2-COOCH₃<br>2-COOH | 58 a<br>58 b |
| " | " | =CH—CH₂—N(CH=N)—C₆H₃(N₃) | 2-COOCH₃<br>2-COOH | 59 a<br>59 b |
| " | " | =CH—CH₂—N(CH=N)—C₆H₃(N₃) | 2-COOCH₃<br>2-COOH | 60 a<br>60 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | =CH-CH₂-N attached to benzene ring with N=CH-N, 4-OCH₃ substituent | 2-COOCH₃ / 2-COOH | 61 a / 61 b |
| -CH₂O- | H | =CH-CH₂-N attached to benzene ring with N=CH-N, 3-OCH₃ substituent | 2-COOCH₃ / 2-COOH | 62 a / 62 b |
| " | " | =CH-CH₂-N attached to benzene ring with N=CH-N, 4-OC₂H₅ substituent | 2-COOCH₃ / 2-COOH | 63 a / 63 b |
| " | " | =CH-CH₂-N attached to benzene ring with N=CH-N, 3-OC₂H₅ substituent | 2-COOCH₃ / 2-COOH | 64 a / 64 b |
| " | " | =CH-CH₂-N attached to benzene ring with N=CH-N, 4-OCH(CH₃)₂ substituent | 2-COOCH₃ / 2-COOH | 65 a / 65 b |
| " | " | =CH-CH₂-N attached to benzene ring with N=CH-N, 3-OCH(CH₃)₂ substituent | 2-COOCH₃ / 2-COOH | 66 a / 66 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| | | (=CH-CH₂-N=CH-N< ; phenyl with 4-OCH₂Ph) | 2-COOCH₃<br>2-COOH | 67 a<br>67 b |
| —CH₂O— | H | (=CH-CH₂-N=CH-N< ; phenyl with OCH₂Ph) | 2-COOCH₃<br>2-COOH | 68 a<br>68 b |
| " | " | (=CH-CH₂-N=CH-N< ; phenyl with 4-SCH₃) | 2-COOCH₃<br>2-COOH | 69 a<br>69 b |
| " | " | (=CH-CH₂-N=CH-N< ; phenyl with SCH₃) | 2-COOCH₃<br>2-COOH | 70 a<br>70 b |
| " | " | (=CH-CH₂-N=CH-N< ; phenyl with OH) | 2-COOCH₃<br>2-COOH | 71 a<br>71 b |
| " | " | (=CH-CH₂-N=CH-N< ; phenyl with OH) | 2-COOCH₃<br>2-COOH | 72 a<br>72 b |
| " | " | (=CH-CH₂-N=CH-N< ; phenyl with HO) | 2-COOCH₃<br>2-COOH | 73 a<br>73 b |

TABLE 1-continued
| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| $-CH_2O-$ | H | 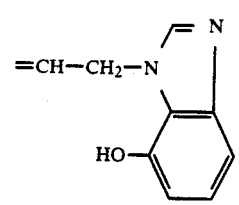 | 2-COOCH$_3$<br>2-COOH | 74 a<br>74 b |
| " | " | 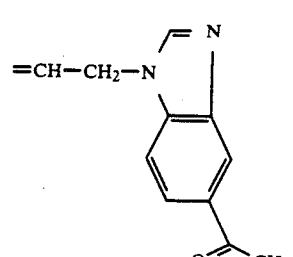 | 2-COOCH$_3$<br>2-COOH | 75 a<br>75 b |
| " | " | 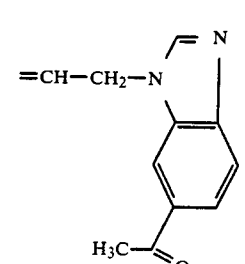 | 2-COOCH$_3$<br>2-COOH | 76 a<br>76 b |
| " | " | 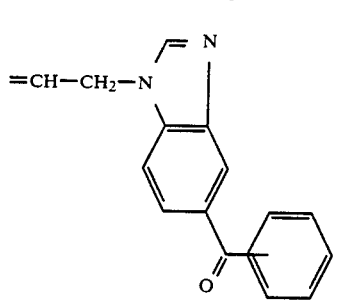 | 2-COOCH$_3$<br>2-COOH | 77 a<br>77 b |
| " | " | 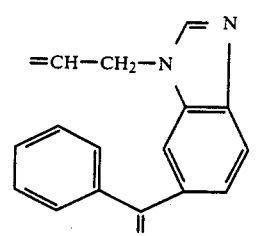 | 2-COOCH$_3$<br>2-COOH | 78 a<br>78 b |
| $-CH_2O-$ | H | 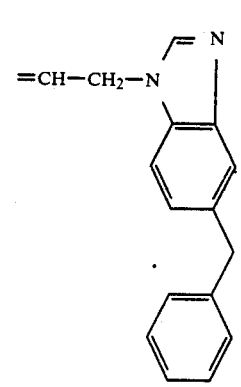 | 2-COOCH$_3$<br>2-COOH | 79 a<br>79 b |

TABLE 1-continued
| $X^1-X^2$ | $(G^A)g^A/(G^B)g^B$ | $-W^1-(CH_2)_n-W^2-Z$ | $R^A/R^B$ | Compound No. |
|---|---|---|---|---|
| " | " | 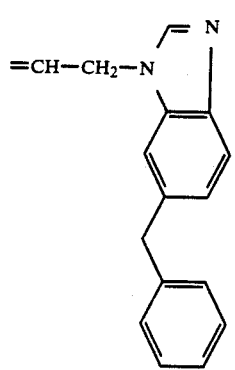 | 2-COOCH$_3$<br>2-COOH | 80 a<br>80 b |
| " | " | 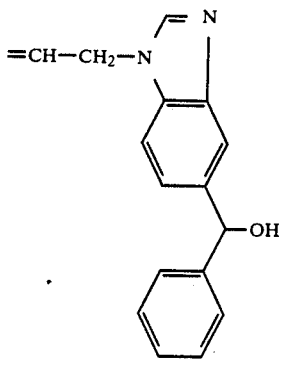 | 2-COOCH$_3$<br>2-COOH | 81 a<br>81 b |
| " | " | 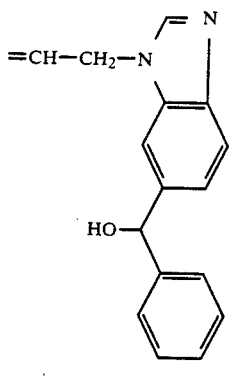 | 2-COOCH$_3$<br>2-COOH | 82 a<br>82 b |
| " | " | 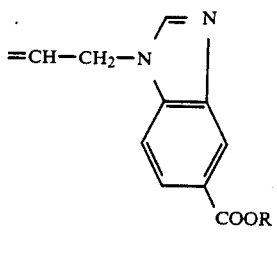 | 2-COOCH$_3$<br>(R = CH$_3$)<br>2-COOH<br>(R = H) | 83 a<br>83 b |
| —CH$_2$O— | H | 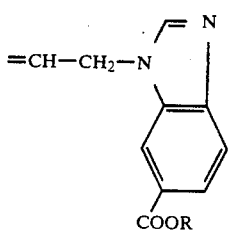 | 2-COOCH$_3$<br>(R = CH$_3$)<br>2-COOH<br>(R = H) | 84 a<br>84 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | =CH–CH$_2$–N, imidazole fused to benzene with CONH(CH$_2$)$_5$CH$_3$ | 2-COOCH$_3$<br>2-COOH | 85 a<br>85 b |
| " | " | =CH–CH$_2$–N, imidazole fused to benzene with CONH(CH$_2$)$_5$CH$_3$ | 2-COOCH$_3$<br>2-COOH | 86 a<br>86 b |
| " | " | =CH–CH$_2$–N, imidazole fused to benzene with CONHCH$_2$–phenyl | 2-COOCH$_3$<br>2-COOH | 87 a<br>87 b |
| " | " | =CH–CH$_2$–N, imidazole fused to benzene with CONHCH$_2$–phenyl | 2-COOCH$_3$<br>2-COOH | 88 a<br>88 b |
| " | " | =CH–CH$_2$–N, imidazole fused to dimethylbenzene (H$_3$C, CH$_3$) | 2-COOCH$_3$<br>2-COOH | 89 a<br>89 b |
| —CH$_2$O— | H | =CH–CH$_2$–N, imidazole fused to dimethylbenzene (H$_3$C, CH$_3$) | 2-CH$_2$COOCH$_3$<br>2-CH$_2$COOH | 90 a<br>90 b |
| " | " | " | 2-CH(CH$_3$)COOCH$_3$<br>2-CH(CH$_3$)COOH<br>2-C(CH$_3$)$_2$COOCH$_3$<br>2-C(CH$_3$)$_2$COOH<br>3-COOCH$_3$<br>3-COOH | 91 a<br>91 b<br>92 a<br>92 b<br>93 a<br>93 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | " | 9-COOCH$_3$ | 94 a |
|   |   |   | 9-COOH | 94 b |
| " | " | ![structure] -CH$_2$-CH$_2$-N attached to benzimidazole with 4,5-dimethyl | 2-COOCH$_3$ | 95 a |
|   |   |   | 2-COOH | 95 b |
| " | " | =CH-CH$_2$-N attached to benzimidazole with 3,4-dimethyl | 2-COOCH$_3$ | 96 a |
|   |   |   | 2-COOH | 96 b |
| —CH$_2$O— | H | =CH-CH$_2$-N attached to benzimidazole with 3,4-dimethyl (other isomer) | 2-COOCH$_3$ | 97 a |
|   |   |   | 2-COOH | 97 b |
| " | " | =CH-CH$_2$-N attached to benzimidazole with 3,6-dimethyl | 2-COOCH$_3$ | 98 a |
|   |   |   | 2-COOH | 98 b |
| " | " | =CH-CH$_2$-N attached to benzimidazole with 3,5-dimethyl | 2-COOCH$_3$ | 99 a |
|   |   |   | 2-COOH | 99 b |
| " | " | =CH-CH$_2$-N attached to methylenedioxybenzimidazole | 2-COOCH$_3$ | 100 a |
|   |   |   | 2-COOH | 100 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | =CH-CH$_2$-N(imidazole-Ar, Ar = 4,5-di-OCH$_3$ phenyl) | 2-COOCH$_3$<br>2-COOH | 101 a<br>101 b |
| " | " | =CH-CH$_2$-N(imidazole-Ar, Ar = 4,5-di-OH phenyl) | 2-COOCH$_3$<br>2-COOH | 102 a<br>102 b |
| —CH$_2$O— | H | =CH-CH$_2$-N(imidazole-Ar, Ar = 3,6-di-OCH$_3$ phenyl) | 2-COOCH$_3$<br>2-COOH | 103 a<br>103 b |
| " | " | =CH-CH$_2$-N(imidazole-Ar, Ar = 3,6-di-OH phenyl) | 2-COOCH$_3$<br>2-COOH | 104 a<br>104 b |
| " | " | =CH-CH$_2$-N(imidazole-Ar, Ar = 3,6-dioxo cyclohexadiene) | 2-COOCH$_3$<br>2-COOH | 105 a<br>105 b |
| " | " | =CH-CH$_2$-N(imidazole-Ar, Ar = 3,4-di-OCH$_3$, phenyl w/ OCH$_3$) | 2-COOCH$_3$<br>2-COOH | 106 a<br>106 b |
| " | " | =CH-CH$_2$-N(imidazole-Ar, Ar = 3,5-di-OCH$_3$ phenyl) | 2-COOCH$_3$<br>2-COOH | 107 a<br>107 b |

TABLE 1-continued
| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| " | " | 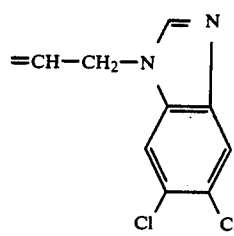 | 2-COOCH$_3$<br>2-COOH | 108 a<br>108 b |
| —CH$_2$O— | H | 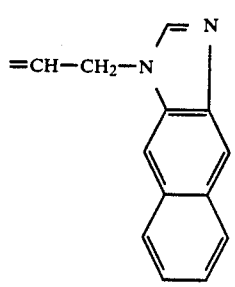 | 2-COOCH$_3$<br>2-COOH | 109 a<br>109 b |
| " | " | 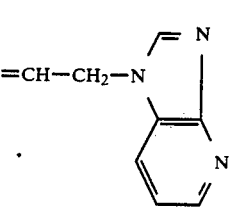 | 2-COOCH$_3$<br>2-COOH | 110 a<br>110 b |
| " | " | 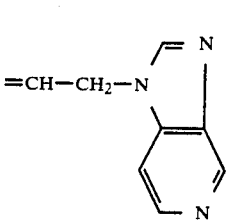 | 2-COOCH$_3$<br>2-COOH | 111 a<br>111 b |
| " | " | 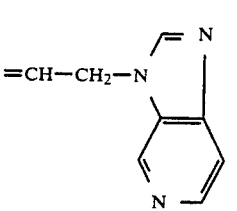 | 2-COOCH$_3$<br>2-COOH | 112 a<br>112 b |
| " | " | 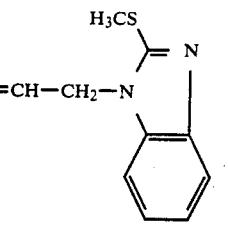 | 2-COOCH$_3$<br>2-COOH | 113 a<br>113 b |
| " | " | 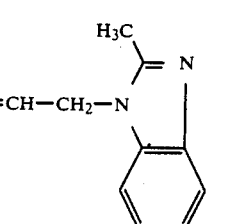 | 2-COOCH$_3$<br>2-COOH | 114 a<br>114 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| $-CH_2O-$ | H | =CH—CH$_2$—N(benzimidazol-1-yl with 2-OH) | 2-COOCH$_3$<br>2-COOH | 115 a<br>115 b |
| " | " | =CH—CH$_2$—N(2-mercaptobenzimidazol-1-yl) | 2-COOCH$_3$<br>2-COOH | 116 a<br>116 b |
| " | " | =CH—CH$_2$—N(purin-9-yl) | 2-COOCH$_3$<br>2-COOH | 117 a<br>117 b |
| " | " | =CH—CH$_2$—N(benzotriazol-1-yl) | 2-COOCH$_3$<br>2-COOH | 118 a<br>118 b |
| " | " | =CH—CH$_2$—N(4,6-dimethylbenzotriazol-1-yl) | 2-COOCH$_3$<br>2-COOH | 119 a<br>119 b |
| " | " | =CH—CH$_2$—N(indol-1-yl) | 2-COOCH$_3$<br>2-COOH | 120 a<br>120 b |
| " | " | =CH—CH$_2$—N(7-azaindol-1-yl) | 2-COOCH$_3$<br>2-COOH | 121 a<br>121 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| —CH₂O— | H | =CH—CH₂—C(=CH—NH—)—(2-methylphenyl) | 2-COOCH₃<br>2-COOH | 122 a<br>122 b |
| " | " | =CH—CH₂—C(=CH—NCH₃—)—(2-methylphenyl) | 2-COOCH₃<br>2-COOH | 123 a<br>123 b |
| " | " | =CH—CH₂—C(=CH—NH—)—(2-methyl-5-CH₃-phenyl) | 2-COOCH₃<br>2-COOH | 124 a<br>124 b |
| " | " | =CH—CH₂—N-(1H-indazol-3(2H)-one) | 2-COOCH₃<br>2-COOH | 125 a<br>125 b |
| " | " | —S—(benzothiazol-2-yl) | 2-CH₂COOCH₃<br>2-CH₂COOH | 126 a<br>126 b |
| " | " | —NH—(benzothiazol-2-yl) | 2-CH₂COOCH₃<br>2-CH₂COOH | 127 a<br>127 b |
| " | " | —NH—CH₂—(1H-benzimidazol-2-yl) | 2-COOCH₃<br>2-COOH | 128 a<br>128 b |
| —CH₂O— | H | —S—CH₂CH₂—(1H-benzimidazol-2-yl) | 2-COOCH₃<br>2-COOH | 129 a<br>129 b |
| " | " | —S—CH₂CH₂—(1-methylbenzimidazol-2-yl) | 2-COOCH₃<br>2-COOH | 130 a<br>130 b |

TABLE 1-continued

| $X^1-X^2$ | $(G^A)g^A/(G^B)g^B$ | $-W^1-(CH_2)_n-W^2-Z$ | $R^A/R^B$ | Compound No. |
|---|---|---|---|---|
| " | " | —S—CH₂CH₂—[benzimidazole, N-benzyl] | 2-COOCH₃<br>2-COOH | 131 a<br>131 b |
| " | " | —S—CH₂CH₂—[benzimidazole, N-(4-methoxybenzyl)] | 2-COOCH₃<br>2-COOH | 132 a<br>132 b |
| " | " | —S—CH₂CH₂—[benzimidazole, N-acetyl] | 2-COOCH₃<br>2-COOH | 133 a<br>133 b |
| " | " | —S—CH₂CH₂—[5-methoxy-1H-benzimidazole] | 2-COOCH₃<br>2-COOH | 134 a<br>134 b |
| " | " | —S—CH₂CH₂—[5-methoxy-N-benzyl-benzimidazole] | 2-COOCH₃<br>2-COOH | 135 a<br>135 b |
| —CH₂O— | H | —S—CH₂CH₂—[5-methoxy-N-(4-methoxybenzyl)-benzimidazole] | 2-COOCH₃<br>2-COOH | 136 a<br>136 b |
| " | " | —S—CH₂CH₂—[5-methoxy-N-benzoyl-benzimidazole] | 2-COOCH₃<br>2-COOH | 137 a<br>137 b |
| " | " | =CH—CH₂—S—[2-pyridyl] | 2-COOCH₃<br>2-COOH | 138 a<br>138 b |

TABLE 1-continued

| $X^1-X^2$ | $(G^A)g^A/(G^B)g^B$ | $-W^1-(CH_2)_n-W^2-Z$ | $R^A/R^B$ | Compound No. |
|---|---|---|---|---|
| " | " | =CH—CH$_2$—S—(pyrimidin-2-yl) | 2-COOCH$_3$<br>2-COOH | 139 a<br>139 b |
| " | " | =CH—CH$_2$—S—(quinolin-2-yl) | 2-COOCH$_3$<br>2-COOH | 140 a<br>140 b |
| " | " | =CH—CH$_2$—S—(3-hydroxypyridin-2-yl) | 2-COOCH$_3$<br>2-COOH | 141·a<br>141 b |
| " | " | =CH—CH$_2$—S—(benzothiazol-2-yl) | 2-COOCH$_3$<br>2-COOH | 142 a<br>142 b |
| " | " | =CH—CH$_2$—NH—(benzothiazol-2-yl) | 2-COOCH$_3$<br>2-COOH | 143 a<br>143 b |
| —CH$_2$O— | H | =CH—CH$_2$—S—(1H-benzimidazol-2-yl) | 2-COOCH$_3$<br>2-COOH | 144 a<br>144 b |
| " | " | =CH—CH$_2$—S—(1-methylbenzimidazol-2-yl) | 2-COOCH$_3$<br>2-COOH | 145 a<br>145 b |
| " | " | =CH—CH$_2$—S—(1-benzylbenzimidazol-2-yl) | 2-COOCH$_3$<br>2-COOH | 146 a<br>146 b |
| " | " | =CH—CH$_2$—NH—(1H-benzimidazol-2-yl) | 2-COOCH$_3$<br>2-COOH | 147 a<br>147 b |
| " | " | =CH—CH$_2$—NH—(1-methylbenzimidazol-2-yl) | 2-COOCH$_3$<br>2-COOH | 148 a<br>148 b |

TABLE 1-continued

| $X^1-X^2$ | $(G^A)g^A/(G^B)g^B$ | $-W^1-(CH_2)_n-W^2-Z$ | $R^A/R^B$ | Compound No. |
|---|---|---|---|---|
| " | " | =CH−CH$_2$−NH−(benzimidazol-2-yl, N-benzyl) | 2-COOCH$_3$<br>2-COOH | 149 a<br>149 b |
| " | " | =CH−CH$_2$−S−(5-methoxy-benzimidazol-2-yl) | 2-COOCH$_3$<br>2-COOH | 150 a<br>150 b |
| " | " | =CH−CH$_2$−NH−(quinolin-2-yl) | 2-COOCH$_3$<br>2-COOH | 151 a<br>151 b |
| −CH$_2$O− | H | =CH−CH$_2$−NH−(pyridin-2-yl) | 2-COOCH$_3$<br>2-COOH | 152 a<br>152 b |
| " | " | −S−(1,3,4-thiadiazol-2-yl)−SH | 2-COOCH$_3$<br>2-COOH | 153 a<br>153 b |
| " | " | −S−(1,3,4-thiadiazol-2,5-diyl)−S−(CH$_2$)$_{17}$−CH$_3$ | 2-COOCH$_3$<br>2-COOH | 154 a<br>154 b |
| " | " | =CH−CH$_2$−NH−(3-phenyl-1,2,4-thiadiazol-5-yl) | 2-COOCH$_3$<br>2-COOH | 155 a<br>155 b |
| " | " | =CH−CH$_2$−S−(4-methyl-1,2,4-triazol-3-yl) | 2-COOCH$_3$<br>2-COOH | 156 a<br>156 b |
| " | " | −SO$_2$−phenyl | 2-COOCH$_3$<br>2-COOH | 157 a<br>157 b |
| " | " | −S−CH$_2$CH$_2$−N(tetrahydroisoquinolin-2-yl) | 2-COOCH$_3$<br>2-COOH | 158 a<br>158 b |
| " | " | −S−CH$_2$CH$_2$−N(1-methyl-tetrahydroisoquinolin-2-yl) | 2-COOCH$_3$<br>2-COOH | 159 a<br>159 b |

TABLE 1-continued

| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| $-CH_2O-$ | H | $-S-CH_2CH_2-N$⟨1-(3,4,5-trimethoxybenzyl)-1,2,3,4-tetrahydroisoquinolin-2-yl⟩ | 2-COOCH$_3$ / 2-COOH | 160 a / 160 b |
| " | " | $-S-CH_2CH_2-N$⟨6,7-dimethoxy-1,2,3,4-tetrahydroisoquinolin-2-yl⟩ | 2-COOCH$_3$ / 2-COOH | 161 a / 161 b |
| " | " | $=CH-CH_2CH_2-N$⟨1,2,3,4-tetrahydroisoquinolin-2-yl⟩ | 2-COOCH$_3$ / 2-COOH | 162 a / 162 b |
| " | " | $=CH-CH_2-N$⟨3-oxo-2,3-dihydro-1,5-benzothiazepin-5-yl⟩ | 2-COOCH$_3$ / 2-COOH | 163 a / 163 b |
| " | " | $=CH-CH_2-N$⟨3-oxo-1,2-benzisothiazol-2(3H)-yl 1,1-dioxide⟩ | 2-COOCH$_3$ / 2-COOH | 164 a / 164 b |
| " | " | $-O-CH_2CH_2-$(2-hydroxyphenyl) | 2-COOCH$_3$ / 2-COOH | 165 a / 165 b |
| $-CH_2S-$ | " | $-S-CH_2-$(pyridin-3-yl) | 2-COOCH$_3$ / 2-COOH | 166 a / 166 b |
| " | " | $-NH-CH_2-$(pyridin-3-yl) | 2-COOCH$_3$ / 2-COOH | 167 a / 167 b |
| $-CH_2S-$ | H | $=CH-CH_2-N$⟨benzimidazol-1-yl⟩ | 2-COOCH$_3$ / 2-COOH | 168 a / 168 b |

TABLE 1-continued
| $X^1-X^2$ | $(G^A)_{g^A}/(G^B)_{g^B}$ | $-W^1-(CH_2)_n-W^2-Z$ | $R^A/R^B$ | Compound No. |
|---|---|---|---|---|
| | " | 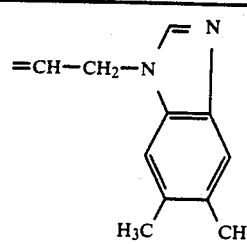 | 2-COOCH₃<br>2-COOH | 169 a<br>169 b |
| " | " | 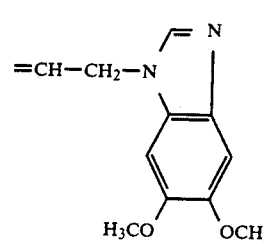 | 2-COOCH₃<br>2-COOH | 170 a<br>170 b |
| —CH₂CH₂— | " | 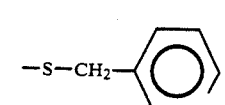 | 2-COOCH₃<br>2-COOH | 171 a<br>171 b |
| " | " | 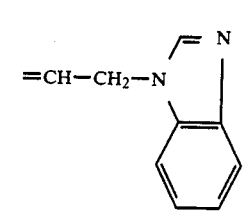 | 2-COOCH₃<br>2-COOH | 172 a<br>172 b |
| " | " | 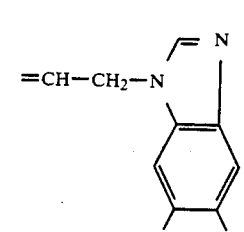 | 2-COOCH₃<br>2-COOH | 173 a<br>173 b |
| " | " | 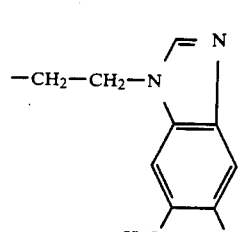 | 2-COOCH₃<br>2-COOH | 174 a<br>174 b |
| —CH₂CH₂— | H | 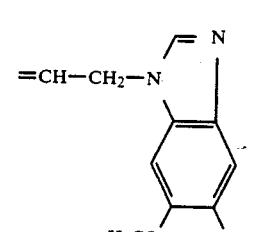 | 2-COOCH₃<br>2-COOH | 175 a<br>175 b |
| —CH=CH— | " | 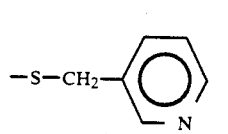 | 2-COOCH₃<br>2-COOH | 176 a<br>176 b |

TABLE 1-continued

| $X^1-X^2$ | $(G^A)_g{}^A/(G^B)_g{}^B$ | $-W^1-(CH_2)_n-W^2-Z$ | $R^A/R^B$ | Compound No. |
|---|---|---|---|---|
| " | " | =CH—CH₂—N(CH₂-phenyl-N) | 2-COOCH₃<br>2-COOH | 177 a<br>177 b |
| " | " | =CH—CH₂—N(CH₂-(4,5-dimethylphenyl)-N) | 2-COOCH₃<br>2-COOH | 178 a<br>178 b |
| " | " | " | 2-CH₂COOCH₃<br>2-CH₂COOH | 179 a<br>179 b |
| " | " | —CH₂—CH₂—N(CH₂-(4,5-dimethylphenyl)-N) | 2-COOCH₃<br>2-COOH | 180 a<br>180 b |
| " | " | =CH—CH₂—N(CH₂-(4-methyl-5,6-dimethoxyphenyl)-N) | 2-COOCH₃<br>2-COOH | 181 a<br>181 b |

The thus prepared Compound (I) possesses a potent TXA₂ biosynthesis inhibitory activity and/or TXA₂ receptor antagonizing activity, and particularly preferred compounds are shown in Table 2.

The compound shown in Table 2, examples, reference examples are shown by correct nomenclature.

TABLE 2

| Compound | Compound No. |
|---|---|
| 11-[(3-Pyridyl)methyl]amino-6,11-dihydrodibenz[b,e]oxepin-2-carboxylic acid | 9c |
| 11-[(3-Pyridyl)methyl]thio-6,11-dihydrodibenz[b,e]oxepin-2-carboxylic acid | 14b |
| 11-[(3-Pyridyl)methyl]oxy-6,11-dihydrodibenz[b,e]oxepin-2-carboxylic acid | 21b |
| 11-[(3-Pyridyl)methyl]imino-6,11-dihydrodibenz[b,e]oxepin-2-carboxylic acid | 25b |
| 11-(3-Pyridine)carboxamido-6,11-dihydrodibenz[b,e]oxepin-2-carboxylic acid | 30b |
| 11-[2-(3-Pyridyl)ethylidene]-6,11-dihydrodibenz[b,e]oxepin-2-carboxylic acid | 36b |
| 11-[2-(3-Pyridyl)ethyl]-6,11-dihydrodibenz[b,e]oxepin-2-carboxylic acid | 40b |
| 11-[2-(1-Benzimidazolyl)ethylidene]-6,11-dihydrodibenz[b,e]oxepin-2-carboxylic acid | 41b |
| 9-Bromo-11-[2-(1-benzimidazolyl)ethylidene]-6,11-dihydrodibenz[b,e]oxepin-2-carboxylic acid | 43b |

TABLE 2 -continued

| Compound | Compound No. |
|---|---|
| 11-[2-(5-Methyl-1-benzimidazolyl)ethylidene]-6,11-dihydrodibenz[b,e]oxepin-2-carboxylic acid | 47b |
| 11-[2-(6-Methyl-1-benzimidazolyl)ethylidene]-6,11-dihydrodibenz[b,e]oxepin-2-carboxylic acid | 48b |
| 11-[2-(5-Chloro-1-benzimidazolyl)ethylidene]-6-11-dihydrodibenz[b,e]oxepin-2-carboxylic acid | 53b |
| 11-[2-(6-Chloro-1-benzimidazolyl)ethylidene]-6,11-dihydrodibenz[b,e]oxepin-2-carboxylic acid | 54b |
| 11-[2-(5-Nitro-1-benzimidazolyl)ethylidene]-6,11-dihydrodibenz[b,e]oxepin-2-carboxylic acid | 55b |
| 11-[2-(6-Nitro-1-benzimidazolyl)ethylidene]-6,11-dihydrodibenz[b,e]oxepin-2-carboxylic acid | 56b |
| 11-[2-(5-Methoxy-1-benzimidazolyl)ethylidene]-6,11-dihydrodibenz[b,e]oxepin-2-carboxylic acid | 61b |
| 11-[2-(6-Methoxy-1-benzimidazolyl)ethylidene]-6,11-dihydrodibenz[b,e]oxepin-2-carboxylic acid | 62b |
| 11-[2-(5-Benzyloxy-1-benzimidazolyl)ethylidene]-6,11-dihydrodibenz[b,e]oxepin-2-carboxylic acid | 67b |
| 11-[2-(6-Benzyloxy-1-benzimidazolyl)ethylidene]-6,11-dihydrodibenz[b,e]oxepin-2-carboxylic acid | 68b |
| 11-[2-(5-Methylthio-1-benzimidazolyl)ethylidene]-6,11-dihydrodibenz[b,e]oxepin-2-carboxylic acid | 69b |
| 11-[2-(6-Methylthio-1-benzimidazolyl)ethylidene]-6,11-dihydrodibenz[b,e]oxepin-2-carboxylic acid | 70b |
| 11-[2-(5-Acetyl-1-benzimidazolyl)ethylidene]-6,11-dihydrodibenz[b,e]oxepin-2-carboxylic acid | 75b |

TABLE 2 -continued

| Compound | Compound No. |
|---|---|
| 11-[2-(6-Acetyl-1-benzimidazolyl)ethylidene]-6,11-dihydrodibenz[b,e]oxepin-2-carboxylic acid | 76b |
| 11-[2-(5-Benzoyl-1-benzimidazolyl)ethylidene]-6,11-dihydrodibenz[b,e]oxepin-2-carboxylic acid | 77b |
| 11-[2-(6-Benzoyl-1-benzimidazolyl)ethylidene]-6,11-dihydrodibenz[b,e]oxepin-2-carboxylic acid | 78b |
| 11-[2-(5-Benzyl-1-benzimidazolyl)ethylidene]-6,11-dihydrodibenz[b,e]oxepin-2-carboxylic acid | 79b |
| 11-[2-(6-Benzyl-1-benzimidazolyl)ethylidene]-6,11-dihydrodibenz[b,e]oxepin-2-carboxylic acid | 80b |
| 11-[2-[5-Hydroxy(phenyl)methyl-1-benzimidazolyl]ethylidene]-6,11-dihydrodibenz[b,e]oxepin-2-carboxylic acid | 81b |
| 11-[2-[6-Hydroxy(phenyl)methyl-1-benzimidazolyl]ethylidene]-6,11-dihydrodibenz[b,e]oxepin-2-carboxylic acid | 82b |
| 11-[2-(5,6-Dimethyl-1-benzimidazolyl)ethylidene]-6,11-dihydrodibenz[b,e]oxepin-2-carboxylic acid | 89b |
| 11-[2-(4,5-Dimethyl-1-benzimidazolyl)ethylidene]-6,11-dihydrodibenz[b,e]oxepin-2-carboxylic acid | 96b |
| 11-[2-(6,7-Dimethyl-1-benzimidazolyl)ethylidene]-6,11-dihydrodibenz[b,e]oxepin-2-carboxylic acid | 97b |
| 11-[2-(4,7-Dimethyl-1-benzimidazolyl)ethylidene]-6,11-dihydrodibenz[b,e]oxepin-2-carboxylic acid | 98b |
| 11-[2-(5,6-Methylenedioxy-1-benzimidazolyl)ethylidene]-6,11-dihydrodibenz[b,e]oxepin-2-carboxylic acid | 100b |
| 11-[2-(5,6-Dimethoxy-1-benzimidazolyl)ethylidene]-6,11-dihydrodibenz[b,e]oxepin-2-carboxylic acid | 101b |
| 11-[2-(4,7-Dimethoxy-1-benzimidazolyl)ethylidene]-6,11-dihydrodibenz[b,e]oxepin-2-carboxylic acid | 103b |
| 11-[2-(Imidazo-p-benzoquinon-1-yl)ethylidene]-6,11-dihydrodibenz[b,e]oxepin-2-carboxylic acid | 105b |
| 11-[2-(2-Methylthio-1-benzimidazolyl)ethylidene]-6,11-dihydrodibenz[b,e]oxepin-2-carboxylic acid | 113b |
| 11-[2-(3-Indolyl)ethylidene]-6,11-dihydrodibenz[b,e]oxepin-2-carboxylic acid | 122b |
| 11-[2-(1-Methyl-3-indolyl)ethylidene]-6,11-dihydrodibenz[b,e]oxepin-2-carboxylic acid | 123b |
| 11-[2-(5-Methoxy-3-indolyl)ethylidene]-6,11-dihydrodibenz[b,e]oxepin-2-carboxylic acid | 124b |
| 11-[2-(2-Benzimidazolyl)ethyl]thio-6,11-dihydrodibenz[b,e]oxepin-2-carboxylic acid | 129b |
| 11-[2-(1-Methyl-2-benzimidazolyl)ethyl]thio-6,11-dihydrodibenz[b,e]oxepin-2-carboxylic acid | 130b |
| 11-[2-(1-Benzyl-2-benzimidazolyl)ethyl]thio-6,11-dihydrodibenz[b,e]oxepin-2-carboxylic acid | 131b |
| 11-[2-(1-Acetyl-2-benzimidazolyl)ethyl]thio-6,11-dihydrodibenz[b,e]oxepin-2-carboxylic acid | 133b |
| 11-[2-(5-Methoxy-2-benzimidazolyl)ethyl]thio-6,11-dihydrodibenz[b,e]oxepin-2-carboxylic acid | 134b |
| 11-[2-(1-Benzyl-5-methoxy-2-benzimidazolyl)ethyl]thio-6,11-dihydrodibenz[b,e]oxepin-2-carboxylic acid | 135b |
| 11-[2-[1-(4-Methoxybenzyl)-5-methoxy-2-benzimidazolyl]ethyl]thio-6,11-dihydrodibenz[b,e]oxepin-2-carboxylic acid | 136b |
| 11-[2-(1-Benzoyl-5-methoxy-2-benzimidazolyl)ethyl]thio-6,11-dihydrodibenz[b,e]oxepin-2-carboxylic acid | 137b |
| 11-[2-(2-Quinolyl)thio]ethylidene]-6,11-dihydrodibenz[b,e]oxepin-2-carboxylic acid | 140b |
| 11-[2-[(3-Hydroxy-2-pyridyl)thio]ethylidene]-6,11-dihydrodibenz[b,e]oxepin-2-carboxylic acid | 141b |
| 11-[2-[(1,2,3,4-Tetrahydroisoquinolin)-2-yl]ethyl]thio-6,11-dihydrodibenz[b,e]oxepin-2-carboxylic acid | 158b |
| 11-[2-[(6,7-Dimethoxy-1,2,3,4-tetrahydroisoquinolin)-2-yl]ethyl]thio-6,11-dihydrodibenz[b,e]oxepin-2-carboxylic acid | 161b |
| 11-[3-[(1,2,3,4-Tetrahydroisoquinolin-2-yl)]propylidene]-6,11-dihydrodibenz[b,e]oxepin-2-carboxylic acid | 162b |
| 11-[2-[(2-Hydroxy)phenyl]ethyl]oxy-6,11-dihydrodibenz[b,e]oxepin-2-carboxylic acid | 165b |
| 11-(3-Pyridyl)methylthio-6,11-dihydrodibenzo[b,e]thiepin-2-carboxylic acid | 166b |
| 11-[2-(1-Benzimidazolyl)ethylidene]-6,11-dihydrodibenzo[b,e]thiepin-2-carboxylic acid | 168b |
| 11-[2-(5,6-Dimethyl-1-benzimidazolyl)ethylidene]-6,11-dihydrodibenzo[b,e]thiepin-2-carboxylic acid | 169b |
| 11-[2-(5,6-Dimethoxy-1-benzimidazolyl)ethylidene]-6,11-dihydrodibenzo[b,e]thiepin-2-carboxylic acid | 170b |
| 5-(3-Pyridyl)methylthio-10,11-dihydro-5H-dibenzo[a,d]cyclohepten-3-carboxylic acid | 171b |
| 5-[2-(1-Benzimidazolyl)ethylidene]-10,11-dihydro-5H-dibenzo[a,d]cyclohepten-3-carboxylic acid | 172b |
| 5-[2-(5,6-Dimethyl-1-benzimidazolyl)ethylidene]-10,11-dihydro-5H-dibenzo[a,d]cyclohepten-3-carboxylic acid | 173b |
| 5-[2-(5,6-Dimethoxy-1-benzimidazolyl)ethylidene]-10,11-dihydro-5H-dibenzo[a,d]cyclohepten-3-carboxylic acid | 175b |
| 5-(3-Pyridyl)methylthio-5H-dibenzo[a,d]cyclohepten-3-carboxylic acid | 176b |
| 5-[2-(1-Benzimidazolyl)ethylidene]-5H-dibenzo[a,d]cyclohepten-3-carboxylic acid | 177b |
| 5-[2-(5,6-Dimethyl-1-benzimidazolyl)ethylidene]-5H-dibenzo[a,d]cyclohepten-3-carboxylic acid | 178b |
| 5-[2-(5,6-Dimethoxy-1-benzimidazolyl)ethylidene]-5H-dibenzo[a,d]cyclohepten-3-carboxylic acid | 181b |

TEST EXAMPLES

Next, pharmacological activities of Compound (I) are described below.

ACUTE TOXICITY TEST

Using three dd strain male mice weighing $20\pm1$ g, a test compound was orally (po; 300 mg/kg) or intraperitoneally (ip; 100 mg/kg) administered. MLD (the minimum lethal dose) was determined by observing the mortality for seven days after administration.

The results are shown in Table 3.

TEST ON ANTI AGGREGATORY EFFECTS (TXA$_2$-ANTAGONIZING ACTION)

Using guinea pig platelet, influence of the compounds on platelet aggregation induced by U-46619 (9,11-dideoxy-9α,11α-methanoepoxyprostaglandin F$_{2\alpha}$; manufactured by Cayman Chemical Co., Ltd.) which was a TXA$_2$/prostaglandin H$_2$ receptor stimulant was examined.

Male guinea pig (Hartley strain; body weight, 300 to 600 g) was anesthesized by intraperitoneal administration of sodium pentobarbital (30 mg/kg) and blood was collected from the descending aorta of the abdomen with a 1/10 volume of 3.8% trisodium citrate. By centrifugation (KC-70: manufactured by Kubota Co., Ltd.) at 800 rpm for 15 minutes, platelet rich plasma (PRP) was obtained. Platelet aggregation induced by U-46619 (0.5–1 μM) was determined by photometry [Born, G.V.R. et al., Nature (London), 194, 927–929 (1962)]. A test compound was pretreated for 3 minutes and the ability to inhibit aggregation was determined. The minimum concentration which inhibits platelet aggregation by 30% or more was defined as the minimum effective concentration (MEC) of the test compound.

The results are shown in Table 3.

TXA$_2$ BIOSYNTHESIS INHIBITORY TEST

After a mixture of 70 μl (40 μg of protein, 100 mM Tris-hydrochloride buffer, pH 7.4) of bovine platelet microsome and 10 μl (10% methanol-containing 100 mM Tris-hydrochloride buffer) of a test compound solution was settled at 0° C. for 5 minutes, 20 μl of prostaglandin H$_2$ solution (0.1 nmol, in Tris-hydrochloride buffer described above containing 20% acetone) as substrate was added to the mixture. Five minutes after, 2.9 ml of stopping solution [100 mM, Trishydrochloride buffer containing 0.1 μM of OKY-1581; Tromb. Res. 23, 145 (1981)] was added to stop the reaction.

TXA$_2$ was unstable in the buffer solution, and nonenzymatically converted to TXB$_2$. An amount of thromboxane B$_2$ (TXB$_2$) formed in the reaction solution was determined by radioimmunoassay [F. A. Fitzpatrick et al., Methods in Enzymology, 86, 286 (1982)]. An inhibition rate of the test compound was calculated according to the following equation.

Inhibition rate (%) =

$$\left\{ 1 - \frac{\begin{array}{c}\text{Amount of } TXB_2 \\ \text{formed when adding} \\ \text{test compound}\end{array} - \begin{array}{c}\text{Amount of } TXB_2 \\ \text{formed in blank}\end{array}}{\begin{array}{c}\text{Amount of } TXB_2 \\ \text{formed in control}\end{array} - \begin{array}{c}\text{Amount of } \overline{TXB_2} \\ \text{formed in blank}\end{array}} \right\} \times 100$$

The amount of TXB$_2$ formed in control refers to a value obtained when the same reaction was carried out, using a solvent containing no test compound.

The amount of TXB$_2$ formed in blank refers to a value obtained when the reaction was carried out in the system in which the stopping solution was added prior to adding substrate.

The results are shown in Table 3.

TABLE 3

| Test Compound Compound No. *4 | Acute Toxicity (MLD) mg/kg po | ip | TXA$_2$ Antagonizing Activity (MEC) μg/ml | TXA$_2$ Biosynthesis Inhibitory Activity Inhibition Rate in 10 μM (%) |
|---|---|---|---|---|
| 9c | >300 | >100 | 30 | 100 |
| 14b | >300 | >100 | 3 | 100 |
| 25b | >300 | >100 | 1 | 100 |
| E-37b' | >300 | >100 | 3 | 94 |
| E-41b' | >300 | >100 | 0.1 | 61 |
| E-61b | — | — | 0.1 | 1 |
| E-62b | — | — | 1 | 11 |
| E-89b' | >300 | >100 | 0.1 | 28 |
| E-101b | >300 | >100 | 0.3 | 17 |
| 129b' | >300 | >100 | 0.3 | 66 |
| E-156b | >300 | >100 | 1.0 | −10 |
| 158b' | >300 | >100 | 1.0 | 56 |
| 165b' | >300 | >100 | 3.0 | 34 |
| BM13505*1 (reference compound) | >300 | >100 | 0.1 | 8 |
| OKY 1581*2 (reference compound) | >300 | >100 | 30 | 100 |
| KW 4679*3 (reference compound) | >300 | >100 | 30 | 1 |

TABLE 3-continued

| Test Compound Compound No. *4 | Acute Toxicity (MLD) mg/kg po | ip | TXA$_2$ Antagonizing Activity (MEC) μg/ml | TXA$_2$ Biosynthesis Inhibitory Activity Inhibition Rate in 10 μM (%) |
|---|---|---|---|---|
| compound) | | | | |

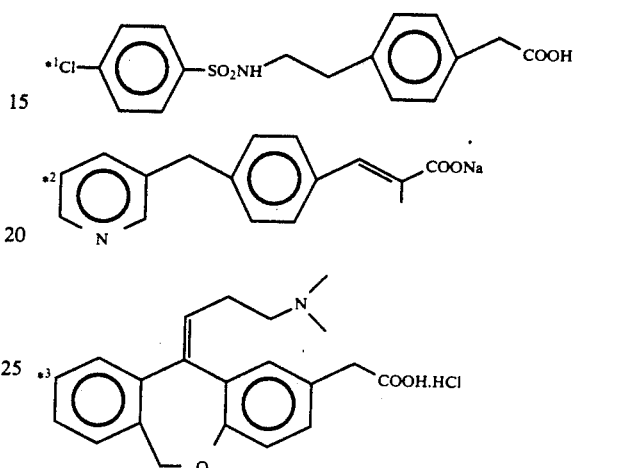

(Japanese Published Unexamined Patent Application No. 10784/88)

*4In Compound No., symbol ' indicates an addition product of the corresponding compound in Tables 1 and 2 to a salt or solvent and symbols E and Z represent E-form and Z-form, respectively (the same shall apply hereinafter)

As demonstrated in Table 3, Compound (I) and pharmaceutically acceptable salts thereof possess a TXA$_2$ receptor antagonizing activity or a TXA$_2$ biosynthesis inhibitory activity and some compounds possess both activities.

ANTITHROMBOTIC ACTIVITY

Effect of a test compound on thrombus formation on cotton thread which was kept in an extracorporeal circulation path for the artery and vein in anesthesized rats was examined in a manner similar to the method of Smith et al. [Br. J. Pharmacol., 77, 29 (1982)].

Wistar male rats weighing 250 to 400 g were anesthesized by intraperitoneal administration of sodium pentobarbital at a dose of 30 mg/kg and an extracorporeal circulation path made of a polyethylene tube having a length of 30 cm extending from the right carotid artery to the left jugular vein was installed. Cotton thread (No. 30) having a length of 5.5 cm was inserted into the circulation path and a weight of thrombus formed on the cotton thread during blood perfusion for 15 minutes was measured. Similar operations were performed twice and the total weight of thrombus formed by the two blood perfusions was shown as the weight of thrombus.

A suspension of the test compound in 0.3% carboxymethyl cellulose was forcedly administered to rats orally in a dose of 1 mg/100 g of rat body weight, 2 hours, prior to the initiation of the test, using a gastic tube for oral administration to small animals.

The results are shown in Table 4.

TABLE 4

| Compound No. | Antithrombotic Activity in Rat | | |
|---|---|---|---|
| | Dose (mg/kg) | Number of animals | Weight of[a] Thrombus (mg) |
| Control group | — | 12 | 22.4 ± 1.2 |
| E-41b' | 0.3 | 6 | 20.2 ± 1.8 |
| | 1 | 6 | 16.9 ± 2.5* |
| | 3 | 6 | 14.2 ± 1.4** |
| | 10 | 5 | 13.5 ± 1.5** |
| Control group | — | 11 | 25.9 ± 1.2 |
| BM13177[b] | 30 | 5 | 24.8 ± 1.8 |
| (reference compound) | 100 | 5 | 18.9 ± 1.8** |

[a] mean value ± standard error
*P < 0.05,
**P < 0.01 (indicates a significant difference against the weight of thrombus in the control group)

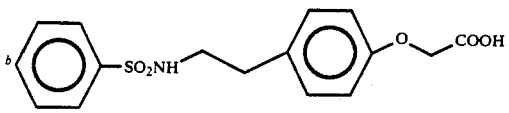

This experimental system is considered to be a simple animal model for extracorporeal blood circulation. Therefore, the effectiveness of the compound in accordance with this invention shown in Table 4 demonstrates that the compound could be a useful inhibitor (antithrombotic agent) against the formation of thrombus which is a problem in e.g., blood dialysis (in renal insufficiency), etc.

However, the effectiveness of the compounds in accordance with this invention is not limited to the disease and condition described above.

Compound (I) or pharmaceutically acceptable salts thereof may be administered singly as they are but in general, it is preferably administered as various medical preparations. These medical preparations are used for animal and human beings.

The medical preparation in accordance with the present invention may contain, as an active ingredient, Compound (I) or pharmaceutically acceptable salts thereof singly or as admixture with other optional effective components for different treatment. Further these medical preparations can be produced by optional procedures well known in the pharmaceutical field, by mixing the active ingredient together with one or more pharmaceutically acceptable carriers.

Herein, as the other effective components for treatment contained together with Compound (I) or pharmaceutically acceptable salts thereof, mention may be made of, for example, a steroid, a non-steroid, a peripheral anti-inflammatory agent, a leucotriene antagonist, a leucotriene biosynthesis inhibitor, an $H_2$ receptor antagonist, an antihistaminic agent, a histamine release inhibitor, a bronchodilator, an angiotensin converting enzyme inhibitor, a thromboxane $A_2$ biosynthesis inhibitor, an $H^+$-$K^+$ ATPase inhibitor, a coronary dilator, a calcium antagonist, a calcium channel operator, a diuretic, a xanthine oxidase inhibitor, a cerebral circulation improving agent, a celebral metabolism activator, a cerebral protecting agent, a liver protecting agent, an antiplatelet agent, a thrombolytic agent, an adrenaline α receptor antagonist, an adrenergic β receptor agent, an adrenaline β receptor antagonist, a serotonine antagonist, a platelet activation factor (PAF) antagonist, a phospholipase $A_2$ inhibitor, an adenosine receptor operator, an adenosine receptor antagonist, an antihyperlipidemic agent, a cholesterol biosynthesis inhibitor, an immunostimulating agent, an immunosuppressive agent, an anticancer agent, etc.

It is preferred that the most effective route for treatment be selected as a route for administration. Oral or parenteral administration such as intrarectal, topical, intranasal, intraocular, intrabuccal, subcutaneous, intramuscular and intravenous routes, etc. are mentioned.

As the form of administration, there are a capsule, a tablet, a granule, a powder, a syrup, an emulsion, a suppository, an ointment, an eyedrop, a nosedrop, a troche, an aerosol, an injection, etc.

A liquid preparation suited for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as a p-hydroxybenzoic acid ester, etc.; flavors such as strawberry flavor, pepper mint, etc. Further a capsule, a tablet, a powder and a granule, etc. can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as an aliphatic ester, etc.; a plasticizer such as glycerine, etc.

A preparation suited for parenteral administration is composed of a sterile aqueous preparation containing active compounds which are preferably isotonic to blood of recipient. For example, with an injection, a solution for injection is prepared using carriers composed of a saline solution, a glucose solution or a mixture of saline water and glucose solution.

A nasal spray preparation is composed of a purified aqueous solution of the active compounds which contains an antiseptic and an isotonic agent. Such a preparation is adjusted to pH compatible with nasal membrane and to an isotonic state.

An ocular preparation is prepared in a manner similar to the nasal spray, except that pH and isotonic factors are controlled so as to fit those of eyes.

A topical preparation is prepared by dissolving or suspending the active compound in one or more media, for example, a mineral oil, petroleum, a polyvalent alcohol or other bases used for topical medical preparations.

A preparation for rectal administration is provided as a suppository using conventional carriers, for example, cacao fat, hydrogenated fat or hydrogenated fat carboxylic acid, etc.

Further these parenteral preparations may also be added with one or more auxiliary components such as a diluent, a fragrance, an antiseptic (including an antioxidant), an excipient, a disintegrator, a lubricant, a binder, a surfactant, a plasticizer and the like as indicated in case of oral administration.

Effective dose and number of administration of Compound (I) or pharmaceutically acceptable salts thereof vary depending upon mode of administration, age and body weight of the patient and properties or severity of conditions to be treated. In general, daily dose is 0.01 to 1000 mg/person and number of administration is once a day, or the dosage may be divided into several ones.

Hereafter, the present invention is described by referring to Examples and Reference Examples below.

In the descriptions in Tables 5-1 through 5-18 in the following examples, symbols " and '" in the compound numbering represent an addition product of the corresponding compound to a salt or solvent as in the symbol

EXAMPLE 1

Ethyl 11-[(3-pyridyl)methyl]amino-6,11-dihydrodibenz[b,e]oxepin-2-carboxylate (Compound 9a)

Ethyl 11-hydroxy-6,11-dihydrodibenz[b,e]oxepin-2-carboxylate (Compound c), 6.0 g, obtained in Reference Example 3 was suspended in 100 ml of methylene chloride and 3 ml of thionyl chloride was dropwise added to the suspension under ice cooling. The mixture was stirred at room temperature for an hour. The solvent was distilled off under reduced pressure to give oily ethyl 11-chloro-6,11-dihydrodibenz[b,e]oxepin-2-carboxylate.

The ester was dissolved in 20 ml of methylene chloride without isolation and purification. Under ice cooling, the solution was dropwise added to 100 ml of methylene chloride solution of 8 ml of 3-aminomethylpyridine and 6 ml of N,N-dicyclohexylmethylamine. After the dropwise addition, the mixture was stirred at room temperature for further 12 hours. The solvent was distilled off under reduced pressure. The resulting residue was subjected to silica gel column chromatography (eluting solvent, hexane:ethyl acetate:triethylamine=10:10:2) to give 3.9 g of the crude product. The obtained crude product was recrystallized from hexane to give 2.3 g of the desired product.

EXAMPLE 2

Butyl 11-[(3-pyridyl)methyl]amino-6,11-dihydrodibenz[b,e]oxepin-2-carboxylate (Compound 9b)

This compound was prepared in a manner similar to Example 1, using butyl 11-hydroxy-6,11-dihydrodibenz[b,e]oxepin-2-carboxylate (Compound d) obtained in Reference Example 4 and 3-aminomethylpyridine.

EXAMPLE 3

Butyl 11-[(3-pyridyl)methyl]amino-6,11-dihydrodibenz[b,e]oxepin-2-carboxylate dihydrochloride monohydrate (Compound 9b')

Compound 9b, 1.7 g, obtained in Example 2 was dissolved in 100 ml of isopropanol and 2 ml of 7N hydrochloric acid/isopropanol solution was added to the solution and the mixture was stirred. After stirring, the mixture was ice cooled. The precipitated solid was taken by filtration and further washed with ether to give 1.0 g of the desired product.

EXAMPLE 4

Ethyl 11-(3-pyridyl)amino-6,11-dihydrodibenz[b,e]oxepin-2-carboxylate (Compound 1a)

EXAMPLE 5

Methyl 11-(3-pyridyl)amino-6,11-dihydrodibenz[b,e]oxepin-2-acetate (Compound 2a)

EXAMPLE 6

Ethyl 11-(4-pyridyl)amino-6,11-dihydrodibenz[b,e]oxepin-2-carboxylate (Compound 7a)

EXAMPLE 7

Methyl 11-[(3-pyridyl)methyl]amino-6,11-dihydrodibenz[b,e]oxepin-2-acetate (Compound 10a)

EXAMPLE 8

Ethyl 11-[(4-pyridyl)methyl]amino-6,11-dihydrodibenz[b,e]oxepin-2-carboxylate (Compound 11a)

EXAMPLE 9

Methyl 2-methyl-2-[11-(3-pyridyl)amino-6,11-dihydrodibenz[b,e]oxepin-2-yl]propionate (Compound 4a)

In Examples 4 through 9, the products were prepared in a manner similar to Example 1, using the corresponding 11-hydroxy-6,11-dihydrodibenz[b,e]oxepin derivative (Compound c, f or g) and 3- or 4-aminomethylpyridine.

EXAMPLE 10

Ethyl 11-[(4-pyridyl)methyl]amino-6,11-dihydrodibenz[b,e]oxepin-2-carboxylate 0.5 fumarate 0.2 hydrate (Compound 11a')

Compound 11a, 2.5 g, obtained in Example 8 was dissolved in 100 ml of isopropanol and 0.8 g of fumaric acid was added to the solution. After stirring at room temperature for an hour, the solvent was distilled off under reduced pressure. The obtained crude product was recrystallized from acetonitrile-ethanol to give 0.9 g of the desired product.

EXAMPLE 11

Ethyl 11-[(2-pyridyl)methyl]amino-6,11-dihydrodibenz[b,e]oxepin-2-carboxylate (Compound 12a)

EXAMPLE 12

Ethyl 11-benzylamino-6,11-dihydrodibenz[b,e]oxepin-2-carboxylate (Compound 13a)

EXAMPLE 13

Methyl 11-(2-benzimidazolyl)methyl-amino-6,11-dihydrodibenz[b,e]oxepin-2-carboxylate (Compound 128a)

In Examples 11 through 13, the products were prepared using the corresponding 11-hydroxy-6,11-dihydrodibenz[b,e]oxepine derivative(Compound b or c) and an amino compound in a manner similar to Example 1.

Physicochemical properties of the compounds obtained in Examples 1 to 13 are shown in Table 5-1.

TABLE 5-1

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 1 (9a) | white crystal | 79–81.5 (hexane) | (CDCl$_3$) 1.36(t, J=7.3Hz, 3H), 2.15 (bs, 1H), 3.70(s, 2H), 4.30(q, J=7.3Hz, 2H), 4.67 (s, 1H), 4.81 & 6.65(ABq, J= 11.9Hz, 2H), 6.83–7.97(m, 9H), 8.28–8.59(m, 2H) | (CHCl$_3$) 2950, 1705, 1610, 1285, 1240 | C$_{23}$H$_{22}$N$_2$O$_3$<br>　　　C　　H　　N<br>Found　73.98　6.01　7.42<br>Calcd.　73.78　5.92　7.48 |

TABLE 5-1-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 2 (9b) | pale yellow oil | — | (CDCl$_3$) 0.80–1.81(m, 7H), 2.08(bs, 1H), 3.71(s, 2H), 4.24(t, J=6.1Hz, 2H), 4.67 (s, 1H), 4.82 & 6.65(ABq, J=11.9Hz, 2H), 6.58–7.95(m, 9H), 8.24–8.56(m, 2H) | (CHCl$_3$) 3040, 2874, 1699, 1612, 1286, 1120 | — |
| 3 (9b') | white solid | 188–191 (ether)* | — | — | C$_{25}$H$_{26}$N$_2$O$_3$.2HCl.H$_2$O<br>　　　C　　H　　N<br>Found　61.02　6.03　5.61<br>Calcd.　60.85　6.13　5.68 |
| 4 (1a) | colorless amorphous | 143–145 | (CDCl$_3$) 1.34(t, J=7.4Hz, 3H), 4.29(q, J=7.4Hz, 2H), 4.82 (bs, 1H), 5.39(s, 1H), 5.05 & 6.07(ABq, J=13.1Hz, 2H), 6.74–8.81(m, 11H) | (CHCl$_3$) 2960, 1705, 1595, 1240 | C$_{22}$H$_{20}$N$_2$O$_3$<br>　　　C　　H　　N<br>Found　73.43　5.50　7.72<br>Calcd.　73.32　5.59　7.77 |
| 5 (2a) | pale yellow amorphous | — | (CDCl$_3$) 3.45(s, 2H), 3.53 (s, 3H), 4.95 & 5.80(ABq, J=14Hz, 2H), 5.30(s, 1H), 6.70–7.50(m, 9H), 7.82(m, 1H), 7.95(bs, 1H) | — | — |
| 6 (7a) | white solid | 202–203 (ethyl acetate) | (CDCl$_3$+DMSO-d$_6$) 1.30(t, J=7.1Hz, 3H), 3.35(s, 1H), 4.24(q, J=7.1Hz, 2H), 5.14 & 5.89(ABq, J=13.3Hz, 2H), 5.73 (d, J=6.4Hz, 1H), 6.51–8.08 (m, 11H), 9.72(s, 1H) | — | C$_{22}$H$_{20}$N$_2$O$_3$<br>　　　C　　H　　N<br>Found　73.02　5.61　7.70<br>Calcd.　73.11　5.86　7.75 |
| 7 (10a) | pale yellow oil | — | (CDCl$_3$) 3.48(s, 2H), 3.60 (s, 3H), 3.67(s, 2H), 4.53 (s, 1H), 4.80 & 6.32(ABq, J=13Hz, 2H), 6.70–7.68(m, 9H), 8.30–8.60(m, 2H) | — | — |
| 8 (11a) | colorless oil | — | (CDCl$_3$) 1.36(t, J=7.2Hz, 3H), 3.71(bs, 2H), 4.30(q, J=7.2Hz, 2H), 4.65(s, 1H), 4.81 & 6.64(ABq, J=12.6Hz, 2H), 6.76–7.91(m, 9H), 8.32–8.61 (m, 2H) | — | — |
| 9 (4a) | colorless oil | — | (CDCl$_3$) 1.53(s, 6H), 3.61(s, 3H), 5.04 & 5.81(ABq, J=14.2 Hz, 2H), 5.36(d, J=6.2Hz, 1H), 6.80–7.55(m, 9H), 7.94(bs, 1H), 8.13(bs, 1H) | (CHCl$_3$) 1726, 1586, 1496, 1149, 1126 | [MS (m/z): 388(M$^+$)] |
| 10 (11a') | white crystal | 133–134 (acetonitrile-ethanol) | — | — | C$_{25}$H$_{24}$N$_2$O$_5$.0.2H$_2$O<br>　　　C　　H　　N<br>Found　68.89　5.62　6.38<br>Calcd.　68.86　5.64　6.42 |
| 11 (12a) | pale yellow solid | 99–100 (hexane) | (CDCl$_3$+D$_2$O) 1.36(t, J=7.5 Hz, 3H), 2.57(bs, 1H), 3.80 (s, 2H), 4.28(q, J=6.9Hz, 2H), 4.65(s, 1H), 4.77 & 6.68(ABq J=11.9Hz, 2H), 6.70–8.67(m, 11H) | (CHCl$_3$) 2984, 1707, 1613, 1287, 1121 | C$_{23}$H$_{22}$N$_2$O$_3$<br>　　　C　　H　　N<br>Found　73.54　5.82　7.39<br>Calcd.　73.78　5.92　7.48 |
| 12 (13a) | colorless crystal | 82–83 (hexane) | (CDCl$_3$) 1.35(t, J=7.2Hz, 3H), 1.94(bs, 1H), 3.67(s, 2H), 4.28(q, J=7.2Hz, 4H), 4.64(s, 1H), 4.79 & 6.71(ABq, J=11.3 Hz, 2H), 6.66–7.99(m, 12H) | (neat) 2980, 1710, 1610, 1500, 1245, 1120 | C$_{24}$N$_{23}$HO$_3$<br>　　　C　　H　　N<br>Found　77.22　6.21　3.63<br>Calcd.　77.19　6.21　3.75 |
| 13 (128a) | pale yellow amorphous | — | (CDCl$_3$) 3.73(s, 3H), 3.83 (bs, 2H), 4.57 & 6.27(ABq, J=12.5Hz, 2H), 4.52(s, 1H), 6.63–8.10(m, 11H) | (CHCl$_3$) 3450, 2950, 2394, 1714, 1613, 1289, 1169 | — |

EXAMPLE 14

11-[(3-Pyridyl)methyl]amino-6,11-dihydrodibenz[b,e]oxepin-2-carboxylic acid (Compound 9c)

Compound 9a, 3.9 g, obtained in Example 1 was heated to reflux for an hour in a solvent mixture of 200 ml of methanol, 50 ml of water and 10 ml of 10N sodium hydroxide aqueous solution. The solvent was distilled off under reduced pressure and 4N hydrochloric acid aqueous solution was added to the residue to adjust pH to 7. After concentrating under reduced pressure, the residue was subjected to high porous polymer (HP-10; manufactured by Mitsubishi Chemical Industry Co., Ltd.) column chromatography (eluting solvent; methanol) to give 2.5 g of the crude product. The crude product was recrystallized from water to give 2.0 g of the desired product.

EXAMPLE 15

11-(3-Pyridyl)amino-6,11-dihydrodibenz[b,e]oxepin-2-carboxylic acid (Compound 1b)

Compound 1a, 2.0 g, obtained in Example 4 was hydrolyzed in a manner similar to Example 14. After completion of the reaction, the solvent was distilled off under reduced pressure and the residue was diluted with water. To the dilution was added 4N hydrochloric acid aqueous solution to adjust pH to 7. The precipitated solid was taken out by filtration and washed with ether to give 1.7 g of the desired product.

EXAMPLE 16

11-(3-Pyridyl)amino-6,11-dihydrodibenz[b,e]oxepin-2-acetic acid (Compound 2b)

EXAMPLE 17

0.1 Isoproplyl 2-methyl-2-[11-(3-pyridyl)amino-6,11-dihydrodibenz[b,e]oxepin-2-yl]propionate (Compound 4b′)

EXAMPLE 18

11-(4-Pyridyl)amino-6,11-dihydrodibenz[b,e]oxepin-2-carboxylic acid 0.5 hydrate (Compound 7b′)

EXAMPLE 19

11-[(3-Pyridyl)methyl]amino-6,11-dihydrodibenz[b,e]oxepin-2-acetic acid (Compound 10b)

EXAMPLE 20

11-[(2-Pyridyl)methyl]amino]-6,11-dihydrodibenz[b,e]oxepin-2-carboxylic acid 0.5 hydrate (Compound 12b′)

EXAMPLE 21

11-Benzylamino-6,11-dihydrodibenz[b,e]oxepin-2-carboxylic acid (Compound 13b)

EXAMPLE 22

11-(2-Benzimidazolyl)methylamino-6,11-dihydrodibenz[b,e]oxepin-2-carboxylic acid monohydrate (Compound 128b′)

In Examples 16 through 22, the products were prepared by hydrolyzing esters of the corresponding oxepine derivatives in a manner similar to Example 14 or 15.

Physicochemical properties of the compounds obtained in Examples 14 to 22 are shown in Table 5-2.

TABLE 5-2

| Example No. (Compound No.) | Appearance | M P °C. (Solvent for recrystallization) | N M R (Solvent) δ, ppm | IR (Method) cm$^{-1}$ | Elemental analysis % |
|---|---|---|---|---|---|
| 14 (9c) | white crystal | 190–191 (water) | (DMSO-d$_6$) 3.63 & 3.70(ABq, J=14.0Hz, 2H), 4.80(s, 1H), 5.01 & 6.61(ABq, J=12.0Hz, 2H), 6.83(d, J=8.5Hz, 1H), 7.28–7.88(m, 8H), 8.40–8.45 (m, 2H) | (KBr tablet) 3600–2700, 1690, 1610, 1235, 1110 | C$_{21}$H$_{18}$N$_2$O$_3$<br>　　　C　　H　　N<br>Found　72.75　5.22　8.05<br>Calcd.　72.82　5.24　8.09 |
| 15 (1b) | white solid | 258 (dec.) (water) | — | — | C$_{20}$H$_{16}$N$_2$O$_3$<br>　　　C　　H　　N<br>Found　72.00　4.81　8.04<br>Calcd.　72.28　4.85　8.43 |
| 16 (2b) | pale yellow amorphous | — | (DMSO-d$_6$) 3.21(s, 2H), 5.14 (d, J=13.4Hz, 1H), 5.68(m, 1H), 5.80(d, J=13.4Hz, 1H), 6.73(d, J=8.3Hz, 1H), 7.00–7.16(m, 3H), 7.24–7.33(m, 4H), 7.60(m, 1H), 7.72(m, 1H), 8.16(s, 1H) | — | — |
| 17 (4b′) | white crystal | 181–182.5 (isopropylether) | (DMSO-d$_6$) 5.15 & 5.86(Abq, J=13.2Hz, 2H), 5.76(d, J=6.8 Hz, 1H), 6.82(d, J=8.5Hz, 1H), 6.9–7.45(m, 7H), 7.66(d, J=7.3Hz, 1H), 7.74(d, J=4.6Hz, 1H), 8.18(d, J=2.7Hz, 1H) | (KBr tablet) 1695, 1580, 1497, 1318, 1225, 1131, 1008 | C$_{23}$H$_{22}$N$_2$O$_3$·0.1C$_6$H$_{14}$O<br>　　　C　　H　　N<br>Found　73.78　6.05　7.09<br>Calcd.　73.69　6.13　7.28 |
| 18 (7b′) | white solid | 258–259 (isopropanol) | — | — | C$_{20}$H$_{16}$N$_2$O$_3$·0.5H$_2$O<br>　　　C　　H　　N<br>Found　70.46　4.85　8.11<br>Calcd.　70.40　5.02　8.21 |
| 19 (10b) | pale yellow amorphous | — | (DMSO-d$_6$) 3.35(s, 2H), 4.61 (s, 1H), 4.87(d, J=12.4Hz, 1H), 6.36(d, J=12.2Hz, 1H), 6.70(d, J=8.1Hz, 1H), 7.03(m, 2H), 7.24–7.34(m, 5H), 7.68 (d, J=7.8Hz, 1H), 8.41(m, 2H) | — | — |
| 20 (12b′) | pale yellow solid | unclear | (DMSO-d$_6$) 3.71 & 3.80(ABq, J=14.7Hz, 2H), 4.82(s, 1H), 4.97 & 6.58(ABq, J=11.8Hz, 2H), 6.82(d, J=8.4Hz, 1H), 7.21–7.75(m, 8H), 7.88(d, J=2.2Hz, 1H), 8.49(d, J=4.0Hz, 1H) | (KBr tablet) 1683, 1609, 1384, 1233, 1114, 1006 | C$_{21}$H$_{18}$N$_2$O$_3$·0.5H$_2$O<br>　　　C　　H　　N<br>Found　70.76　5.09　7.97<br>Calcd.　70.97　5.39　7.88 |
| 21 (13b) | white solid | 145–147 (water) | (DMSO-d$_6$) 3.60 & 3.64(ABq, J=13.8Hz, 2H), 4.77(s, 1H), 5.01 & 6.64(ABq, J=11.8Hz, 2H), 6.83(d, J=8.5Hz, 1H), 7.20–7.44(m, 9H), 7.71(dd, J=2.2 & 8.5Hz, 1H), 7.85(d, J=2.2Hz, 1H) | (KBr tablet) 3180, 1609, 1562, 1364, 1237, 1016 | C$_{22}$H$_{19}$NO$_3$<br>　　　C　　H　　N<br>Found　76.61　5.54　3.90<br>Calcd.　76.50　5.54　4.06 |

TABLE 5-2-continued

| Example No. (Compound No.) | Appearance | M P °C. (Solvent for recrystallization) | N M R (Solvent) δ, ppm | I R (Method) cm$^{-1}$ | Elemental analysis % |
|---|---|---|---|---|---|
| 22 (128b') | yellow solid | — | (DMSO-d$_6$) 3.83 & 3.92(ABq, J=14.9Hz, 2H), 4.95(s, 1H), 5.00 & 6.59(ABq, J=12.1Hz, 2H), 6.87(d, J=8.5Hz, 1H), 7.13–7.53(m, 8H), 7.74(dd, J=2.2 & 8.5Hz, 1H), 7.96(d, J=2.2Hz, 1H) | — | C$_{23}$H$_{19}$N$_3$O$_3$.H$_2$O<br>    C    H    C<br>Found 68.20 4.89 10.59<br>Calcd. 68.47 5.25 10.42 |

EXAMPLE 23

Methyl (Z,E)-11-[2-(1-imidazolyl)ethylidene]-6,11-dihydrodibenz[b,e]oxepin-2-carboxylate (Compound 37a)

In a solvent mixture of 230 ml of toluene and 30 ml of N,N-dimethylformamide, 5.0 g of methyl (Z,E)-11-(2-chloroethylidene)-6,11-dihydrodibenz[b,e]oxepin-2-carboxylate (Compound h; Z/E=1/9) obtained in a manner similar to Reference Example 8 and 4.8 g of imidazole were heated to reflux for 6 hours. After allowing to cool, the solvent was distilled off under reduced pressure. The obtained residue was extracted with 500 ml of methylene chloride and washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting liquid; methanol:ethyl acetate:triethylamine=1:10:1) to give 5.8 g of the product (Z/E=1/9).

EXAMPLE 24

Methyl (E)-11-[2-(1-benzimidazolyl)ethylidene]-6,11-dihydrodibenz[b,e]oxepin-2-carboxylate (Compound E-41b)

Methyl (E)-11-(2-chloroethylidene)-6,11-dihydrodibenz[b,e]oxepin-2-carboxylate (Compound h), 4.0 g, obtained in Reference Example 8 and 6.0 g of benzimidazole were treated in a manner similar to Example 23 to give 4.1 g of the desired product.

EXAMPLE 25

Methyl (E)-11-[2-(5-nitro-1-benzimidazolyl)ethylidene]-6,11-dihydrodibenz[b,e]oxepin-2-carboxylate (Compound E-55a) and methyl (E)-11-[2-(6-nitro-1-benzimidazolyl)ethylidene]-6,11-dihydrodibenz[b,e]oxepin-2-carboxylate (Compound E-56a)

Compound h, 2.0 g, and 5.2 g of 5-nitrobenzimidazole were treated in a manner similar to Example 23 to give a 1:1 mixture of Compounds E-55a and E-56a. The mixture was separated and purified by silica gel column chromatography (eluting solvent, hexane:ethyl acetate:triethylamine=10:10:1) to give 1.1 g of methyl (E)-11-[2-(5-nitro-1-benzimidazolyl)ethylidene]-6,11-dihydrodibenz[b,e]oxepin-2-carboxylate (Compound E-55a) and 0.7 g of methyl (E)-11-[2-(6-nitro-1-benzimidazolyl)ethylidene]-6,11-dihydrodibenz[b,e]oxepin-2-carboxylate (Compound E-56a).

EXAMPLE 26

Methyl (E)-11-[2-(5-methoxy-1-benzimidazolyl)ethylidene]-6,11-dihydrodibenz[b,e]oxepin-2-carboxylate (Compound E-61a) and methyl (E)-11-[2-(6-methoxy-1-benzimidazolyl)ethylidene]-6,11-dihydrodibenz[b,e]oxepin-2-carboxylate (Compound E-62a)

Compound h, 2.9 g, and 4.2 g of 5-methoxybenzimidazole were treated in a manner similar to Example 23 to give a 1:1 mixture of Compounds E-61a and E-62a. The mixture was separated and purified by silica gel column chromatography (eluting solvent, hexane:ethyl acetate:triethylamine=10:10:1) to give 0.8 g of methyl (E)-11-[2-(5-methoxy-1-benzimidazolyl)ethylidene]-6,11-dihydrodibenz[b,e]oxepin-2-carboxylate (Compound E-61a), 0.5 g of methyl (E)-11-[2-(6-methoxy-1-benzimidazolyl)ethylidene]-6,11-dihydrodibenz[b,e]oxepin-2-carboxylate (Compound E-62a) and 2.3 g of the mixture of Compounds E-61a and E-62a.

EXAMPLE 27

Methyl (E)-11-[2-(4-phenylimidazolyl)ethylidene]-6,11-dihydrodibenz[b,e]oxepin-2-carboxylate (Compound E-38a).

EXAMPLE 28

Methyl (E)-11-[2-(5-fluoro-1-benzimidazolyl)ethylidene]-6,11-dihydrodibenz[b,e]oxepin-2-carboxylate (Compound E-49a) and
methyl (E)-11-[2-(6-fluoro-1-benzimidazolyl)ethylidene]-6,11-dihydrodibenz[b,e]oxepin-2-carboxylate (Compound E-50a)

EXAMPLE 29

Methyl (E)-11-[2-(5-trifluoromethyl-1-benzimidazolyl)ethylidene]-6,11-dihydrodibenz[b,e]oxepin-2-carboxylate (Compound E-51a) and
methyl (E)-11-[2-(6-trifluoromethyl-1-benzimidazolyl)ethylidene]-6,11-dihydrodibenz[b,e]oxepin-2-carboxylate (Compound E-52a)

EXAMPLE 30

Methyl (E)-11-[2-(5-chloro-1-benzimidazolyl)ethylidene]-6,11-dihydrodibenz[b,e]oxepin-2-carboxylate (Compound E-53a) and
methyl (E)-11-[2-(6-chloro-1-benzimidazolyl)ethylidene]-6,11-dihydrodibenz[b,e]oxepin-2-carboxylate (Compound E-54a)

EXAMPLE 31

Methyl (E)-11-[2-[5-(1-phenyl-1-hydroxy)methyl-1-benzimidazolyl]ethylidene]-6,11-dihydrodibenz[b,e]oxepin-2-carboxylate (Compound E-81a) and
methyl (E)-11-[2-[6-(1-phenyl-1-hydroxy)methyl-1-benzimidazolyl]ethylidene]-6,11-dihydrodibenz[b,e]oxepin-2-carboxylate (Compound E-82a)

EXAMPLE 32

Methyl (E)-11-[2-(5-methoxycarbonyl-1-benzimidazolyl)ethylidene]-6,11-dihydrodibenz[b,e]oxepin-2-carboxylate (Compound E-83a) and
methyl (E)-11-[2-(6-methoxycarbonyl-1-benzimidazolyl)ethylidene]-6,11-dihydrodibenz[b,e]oxepin-2-carboxylate (Compound E-84a)

In Examples 27 through 32, the products were prepared using Compound h and corresponding benzimidazole derivatives in a manner similar to Example 26.

EXAMPLE 33

A 1:1 mixture of methyl (E)-11-[2-(5-methyl-1-benzimidazolyl)ethylidene]-6,11-dihydrodibenz[b,e]oxepin-2-carboxylate (Compound E-47a) and methyl (E)-11-[2-(6-methyl-1-benzimidazolyl)ethylidene]-6,11-dihydrodibenz[b,e]oxepin-2-carboxylate (Compound E-48a)

EXAMPLE 34

A 1:1 mixture of methyl (E)-11-[2-[5-[N-(1-hexyl)carbamoyl]1-benzimidazolyl]ethylidene]-6,11-dihydrodibenz[b,e]oxepin-2-carboxylate (Compound E-85a) and
methyl (E)-11-[2-[6-[N-(1-hexyl)carbamoyl]-1-benzimidazolyl]ethylidene]-6,11-dihydrodibenz[b,e]oxepin-2-carboxylate (Compound E-86a)

EXAMPLE 35

A 1:1 mixture of methyl (E)-11-[2-[5-(N-benzylcarbamoyl)-1-benzimidazolyl]ethylidene]-6,11-dihydrodibenz[b,e]oxepin-2-carboxylate (Compound E-87a) and
methyl (E)-11-[2-[6-(N-benzylcarbamoyl)-1-benzimidazolyl]ethylidene]-6,11-dihydrodibenz[b,e]oxepin-2-carboxylate (Compound E-88a)

In Examples 33 through 35, the products were prepared using Compound h and corresponding benzimidazole derivatives in a manner similar to Example 26. Isolation of position isomers was not carried out.

EXAMPLE 36

Methyl (E)-11-[2-(4,5-dimethyl-1-benzimidazolyl)ethylidene]-6,11-dihydrodibenz[b,e]oxepin-2-carboxylate (Compound E-96a)

EXAMPLE 37

Methyl (E)-11-[2-(4,6-dimethyl-1-benzimidazolyl)ethylidene]-6,11-dihydrodibenz[b,e]oxepin-2-carboxylate (Compound E-99a)

EXAMPLE 38

Methyl (E)-11-[2-(4,6-dimethoxy-1-benzimidazolyl)ethylidene]-6,11-dihydrodibenz[b,e]oxepin-2-carboxylate (Compound E-106a)

EXAMPLE 39

Methyl (E)-11-[2-(5,7-dimethoxy-1-benzimidazolyl)ethylidene]-6,11-dihydrodibenz[b,e]oxepin-2-carboxylate (Compound E-107a)

In Examples 36 through 39, the products were prepared using Compound h and corresponding benzimidazole derivatives in a similar manner to Example 26.

EXAMPLE 40

Methyl (E)-11-[2-(5,6-dimethyl-1-benzimidazolyl)ethylidene]-6,11-dihydrodibenz[b,e]oxepin-2-carboxylate (Compound E-89a)

EXAMPLE 41

Methyl (E)-11-[2-(5,6-methylenedioxy-1-benzimidazolyl)ethylidene]-6,11-dihydrodibenz[b,e]oxepin-2-carboxylate (Compound E-100a)

EXAMPLE 42

Methyl (E)-11-[2-(5,6-dimethoxy-1-benzimidazolyl)ethylidene]-6,11-dihydrodibenz[b,e]oxepin-2-carboxylate (Compound E-101a)

EXAMPLE 43

Methyl (E)-11-[2-(5,6-dichloro-1-benzimidazolyl)ethylidene]-6,11-dihydrodibenz[b,e]oxepin-2-carboxylate (Compound E-108a)

EXAMPLE 44

Methyl (E)-11-[2-(1-naphtho[2,3-d]imidazolyl)ethylidene]-6,11-dihydrodibenz[b,e]oxepin-2-carboxylate (Compound E-109a)

EXAMPLE 45

Methyl (E)-11-[2-(4-aza-1-benzimidazolyl)ethylidene]-6,11-dihydrodibenz[b,e]oxepin-2-carboxylate (Compound E-110a)

EXAMPLE 46

Methyl (E)-11-[2-(2-methylthio-1-benzimidazolyl)ethylidene]-6,11-dihydrodibenz[b,e]oxepin-2-carboxylate (Compound E-113a)

EXAMPLE 47

Methyl (E)-11-[2-(2-methyl-1-benzimidazolyl)ethylidene]-6,11-dihydrodibenz[b,e]oxepin-2-carboxylate (Compound E-114a)

EXAMPLE 48

Methyl (E)-11-[2-(1-benzotriazolyl)ethylidene]-6,11-dihydrodibenz[b,e]oxepin-2-carboxylate (Compound E-118a)

EXAMPLE 49

Methyl (E)-11-[2-(7-aza-1-indolyl)ethylidene]-6,11-dihydrodibenz[b,e]oxepin-2-carboxylate (Compound E-121a)

In Examples 40 through 49, the products were prepared in a manner similar to Example 23, using Compound h and the corresponding benzimidazole or indole derivatives.

EXAMPLE 50

Methyl (Z,E)-9-bromo-11-[2-(1-benzimidazolyl)ethylidene]-6,11-dihydrodibenz[b,e]oxepin-2-carboxylate (Compound 43a)

Methyl (Z,E)-9-bromo-11-(2-chloroethylidene)-6,11-dihydrodibenz[b,e]oxepin-2-carboxylate (Compound k; Z/E=½), 1.5 g obtained in Reference Example 11, and 1.1 g of benzimidazole were treated in a manner similar to Example 23 to prepare the objective compound (Z/E=½).

EXAMPLE 51

Methyl (Z)-11-[2-(5,6-dimethyl-1-benzimidazolyl)ethylidene]-6,11-dihydrodibenz[b,e]oxepin-2-carboxylate (Compound Z-89a)

Methyl (Z,E)-11-(2-chloroethylidene)-6,11-dihydrodibenz[b,e]oxepin-2-carboxylate (Compound h; Z/E=1/1), 1.1 g obtained in a similar manner to Reference Example 8 was reacted with 0.61 g of 5,6-dimethyl-benzimidazole in 50 ml of tetrahydrofuran in the presence of 0.17 g of 60% oily sodium hydride at room temperature for one night. The reaction mixture was extracted with 300 ml of ethyl acetate, and washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=20:20:1) to give 300 mg of the desired product (Z-form).

EXAMPLE 52

Methyl (E)-11-[2-(5,6-dimethyl-1-benzimidazolyl)ethylidene]-6,11-dihydrodibenz[b,e]oxepin-2-acetate (Compound E-90a)

EXAMPLE 53

Methyl (E)-11-[2-(5,6-dimethyl-1-benzimidazolyl)ethylidene]-6,11-dihydrodibenz[b,e]oxepin-3-carboxylate (Compound E-93a)

EXAMPLE 54

Methyl (E)-11-[2-(5,6-dimethyl-1-benzimidazolyl)ethylidene]-6,11-dihydrodibenz[b,e]oxepin-9-carboxylate (Compound E-94a)

In Examples 52 through 54, the desired products were prepared in a similar manner to Example 23, using Compound l, i or j obtained in Reference Example 12, 9 or 10 and 5,6-dimethylbenzimidazole.

EXAMPLE 55

Methyl (Z,E)-5-[2-(1-benzimidazolyl)ethylidene]-10,11-dihydro-5H-dibenzo[a,d]cyclohepten-3-carboxylate (Compound 172a; Z/E=7/3)

EXAMPLE 56

Methyl (Z,E)-5-[2-(5,6-dimethyl-1-benzimidazolyl)ethylidene]-10,11-dihydro-5H-dibenzo[a,d]cyclohepten-3-carboxylate (Compound 173a; Z/E=7/3)

EXAMPLE 57

Methyl (Z,E)-5-[2-(1-benzimidazolyl)ethylidene]-5H-dibenzo[a,d]cyclohepten-3-carboxylate (Compound 177a; Z/E=1/1)

EXAMPLE 58

Methyl (Z,E)-5-[2-(5,6-dimethyl-1-benzimidazolyl)ethylidene]-5H-dibenzo[a,d]cyclohepten-3-carboxylate (Compound 178a; Z/E=1/1)

EXAMPLE 59

Methyl (Z,E)-5-[2-(5,6-dimethyl-1-benzimidazolyl)ethylidene]-5H-dibenzo[a,b]cyclohepten-3-acetate (Compound 179a; Z/E=11/9)

In Examples 55 through 59, the products were prepared in a similar manner to Example 23 using Compound r, t or u obtained in Reference Example 18, 20 or 21 and corresponding benzimidazole derivatives.

The physicochemical properties of the compounds obtained in Examples 23 through 59 are shown in Table 5-3.

TABLE 5-3

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 23 (37a) | yellow amorphous | — | (CDCl$_3$) 3.82(s,3H), 4.60 (d,J=7.6Hz,2H), 4.55–5.56 (b,2H), 6.17(t,J=7.2Hz,1H), 6.66–8.04(m,10H) | (CHCl$_3$) 2950, 1713, 1609, 1296, 1121, 1005 | — |
| 24 (E-41a) | pale yellow amorphous | unclear | (CDCl$_3$) 3.86(s,3H),4.86 (d,J=7.2Hz,2H), 4.72–5.54 (b,2H), 6.24(t,J=7.2Hz,1H), 6.69–8.21(m,11H), 7.83(s,1H) | — | — |
| 25 (E-55a) | pale yellow oil | — | (CDCl$_3$) 3.87(s,3H), 4.97 (d,J=7.0Hz,2H), 4.80–5.45 (b,2H), 6.25(t,J=7.0Hz,1H), 6.64–8.29(m,10H), 8.58(d,J=1.8Hz,1H) | — | — |
| 25 (E-56a) | pale yellow oil | — | (DMSO-d$_6$) 3.78(s,3H), 4.80–5.50(m,4H), 6.31(t,J=7.0 Hz,1H), 6.75–8.08(m,10H), 8.55(s,1H) | — | — |
| 26 (E-61a) | white crystal | 99–101 (toluene) | (CDCl$_3$) 3.84(s,3H), 3.87 (s,3H), 4.7–5.6(m,4H), 4.88 (d,J=7.3Hz,2H), 6.28(t,J=7.3Hz,1H), 6.75–8.00(m,11H) | (KBr tablet) 3400, 2948, 1714, 1606, 1492, 1436, 1228, 1119, 837, 767 | — |
| 26 (E-62a) | white crystal | 179–180 (acetonitrile) | (CDCl$_3$) 3.80(s,3H), 3.88(s, 3H), 4.7–5.7(m,4H), 4.87(d, J=7.1Hz,2H), 6.29(t,J=7.1 Hz,1H), 6.54(d,J=2.2Hz,1H), 6.72–8.01(m,10H) | (KBr tablet) 3450, 1717, 1505, 1485, 1249, 1004, 818, 767 | — |
| 27 (E-38a) | colorless amorphous | — | (CDCl$_3$) 3.88(s,3H), 4.70(d, J=7.0Hz,2H), 4.8–5.6(b,2H), 6.30(t,J=7.0Hz,1H), 6.82(d, J=8.6Hz,1H), 7.14(d,J=1.5 | (CHCH$_3$) 1709, 1606, 1485, 1435, 1244, 1118, | [MS(m/z: 422(M$^+$)] |

TABLE 5-3-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| | | | Hz,1H), 7.1-7.5(m,9H), 7.70 (d,J=1.5Hz,1H), 7.83(dd,J= 2.2 & 8.5Hz,1H), 8.01(d,J= 2.2Hz,1H) | 1002 | |
| 28 (E-49a) | colorless amorphous | — | (CDCl$_3$) 3.87(s,3H), 4.93(d, J=7.0Hz,2H), 4.9-6.5(b,2H), 6.28(t,J=7.0Hz,1H), 6.80(d, J=8.5Hz,1H), 6.85-7.05(m, 2H), 7.2-7.5(m,5H), 7.81 (dd,J=2.0 & 8.5Hz,1H), 7.93 (s,1H), 7.98(d,J=2.0Hz,1H) | — | [MS(m/z): 414(M$^+$)] |
| 28 (E-50a) | colorless amorphous | — | (CDCl$_3$) 3.87(s,3H), 4.89(d, J=7.0Hz,2H), 5.0-6.5(b,2H), 6.25(t,J=7.0Hz,1H), 6.55- 6.70(m,1H), 6.80(d,J=8.5Hz, 1H), 6.85-7.10(m,1H), 7.2- 7.7(m,5H), 7.81(dd,J=2.0 & 8.5Hz,1H), 7.88(s,1H), 8.00 (d,J=2.0Hz,1H) | — | [MS(m/z): 414(M$^+$)] |
| 29 (E-51a) | colorless oil | — | (CDCl$_3$) 3.85(s,3H), 4.90(d, J=7.0Hz,2H), 4.8-5.6(b,2H), 6.24(t,J=7.0Hz,1H), 6.80(d, J=8.5Hz,1H), 7.0-8.3(m,10H) | (CHCl$_3$) 1712, 1608, 1328, 1251, 1166, 1112, 995 | [MS(m/z): 464(M$^+$)] |
| 29 (E-52a) | colorless oil | — | (CDCl$_3$) 3.85(s,3H), 4.88(d, J=7.0Hz,2H), 4.8-5.6(b,2H), 6.25(t,J=7.0Hz,1H), 6.78(d, J=8.5Hz,1H), 7.1-8.1(m,10H) | (CHCl$_3$) 1712, 1607, 1344, 1243, 1162, 1005 | [MS(m/z): 464(M$^+$)] |
| 30 (E-53a) | colorless oil | — | (CDCl$_3$) 3.87(s,3H), 4.90(d, J=7.0Hz,2H), 4.5-5.6(b,2H), 6.26(t,J=7.0Hz,1H), 6.80(d, J=8.5Hz,1H), 6.91-7.90(m, 9H), 7.99(d,J=2.2Hz,1H) | — | [MS(m/z): 430(M$^+$)] |
| 30 (E-54a) | colorless oil | — | (CDCl$_3$) 3.87(s,3H), 4.89(d, J=7.0Hz,2H), 4.5-5.7(b,2H), 6.22(t,J=7.0Hz,1H), 6.80(d, J=8.6Hz,1H), 6.91(d,J=1.3 Hz,1H), 7.10-7.87(m,7H), 7.83(s,1H), 7.99(d,J=2.2Hz, 1H) | — | [MS(m/z): 430(M$^+$)] |
| 31 (E-81a) | colorless oil | — | (CDCl$_3$) 3.87(s,3H), 4.91(d, J=7.0Hz,2H), 4.5-5.6(b,2H), 5.92(s,1H), 6.7-8.0(m,16H) | — | [MS(m/z): 502(M$^+$)] |
| 31 (E-82a) | colorless oil | — | — | — | [MS(m/z): 502(M$^+$)] |
| 32 (E-83a) | colorless oil | — | (CDCl$_3$) 3.87 & 3.93(each s, 6H), 4.95(d,J=7.1Hz,2H), 4.6-5.7(b,2H), 6.29(t,J=7.1 Hz,1H), 6.80(d,J=8.6Hz,1H), 7.07(d,J=8.6Hz,1H), 7.26- 7.52(m,5H), 7.81(dd,J=2.2 & 8.6Hz,1H), 7.90(s,1H), 8.00 (d,J=2.2Hz,1H), 8.50(d,J= 1.4Hz,1H) | (CHCl$_3$) 1711 | [MS(m/z): 454(M$^+$)] |
| 32 (E-84a) | white crystal | 231-232 (toluene) | (CDCl$_3$) 3.87 & 3.95(each s, 6H), 4.99(d,J=7.0Hz,2H), 4.5-5.8(b,2H), 6.23(t,J=7.0 Hz,1H), 6.80(d,J=8.6Hz,1H), 7.25-8.01(m,10H) | (KBr tablet) 1712, 1282, 1250, 1131, 1004 | C$_{27}$H$_{22}$N$_2$O$_5$<br>　　　C　　H　　N<br>Found　71.42　4.91　6.25<br>Calcd.　71.35　4.88　6.16 |
| 33 (mixture of E-47a and E-48a) | colorless oil | — | (CDCl$_3$) 2.37(s,1.5H), 2.41 (s,1.5H), 3.86(s,3H), 4.84 (d,J=7.2Hz,2H), 4.58-5.57 (b,2H), 6.23(t,J=7.2Hz,1H), 6.78-7.50(m,8H), 7.76(s,1H), 7.79(dd,J=2.0 & 8.6Hz,1H), 7.98(d,J=2.0Hz,1H) | — | [MS(m/z): 410(M$^+$)] |
| 34 (mixture of E-85a and E-86a) | colorless oil | — | (CDCl$_3$) 0.75-1.90(m,11H), 3.35-3.70(m,2H), 3.87(s, 3H), 4.97(d,J=7.3Hz,2H), 4.8-5.3(b,2H), 6.0-6.4(m, 1H), 6.80(d,J=8.6Hz,1H), 7.0-8.40(m,11H) | (neat) 1715, 1246, 1002 | [MS(m/z): 523(M$^+$)] |
| 35 (mixture of E-87a and E-88a) | colorless oil | — | (CDCl$_3$) 3.86(s,3H), 4.3- 5.7(b,2H), 4.68(d,J=5.7Hz, 2H), 4.89-5.00(m,2H), 6.14- 6.31(m,1H), 6.3-8.17(m, 11H) | (neat) 1704, 1118, 1002 | [MS(m/z): 529(M$^+$)] |
| 36 | colorless | — | (CDCl$_3$) 2.37(s,3H), 2.57(s, | — | [MS(m/z): 424(M$^+$)] |

TABLE 5-3-continued

| Example No. (Compound No.) | Appearance | MP °C. (Solvent for recrystallization) | NMR (Solvent) δ, ppm | IR (Method) cm⁻¹ | Elemental analysis % |
|---|---|---|---|---|---|
| (E-96a) | oil | | 3H), 3.86(s,3H), 4.86(d,J= 7.0Hz,2H), 4.68-5.57(b,2H), 6.25(t,J=7.2Hz,1H), 6.68-7.50(m,7H), 7.76(s,1H), 7.79(dd,J=2.2 & 8.6Hz,1H), 7.98(d,J=2.2Hz,1H) | | |
| 37 (E-99a) | colorless oil | — | (CDCl₃) 2.37(s,3H), 2.59(s, 3H), 3.86(s,3H), 4.84(d,J= 7.3Hz,2H), 4.50-5.56(b,2H), 6.23(t,J=7.2Hz,1H), 6.55-6.90(m,2H), 7.15-7.50(m, 5H), 7.74(s,1H), 7.72-7.85 (m,1H), 7.89-8.01(m,1H) | — | [MS(m/z): 424(M⁺)] |
| 38 (E-106a) | colorless oil | — | (CDCl₃) 3.77(s,3H), 3.88(s, 3H), 3.98(s,3H), 4.84(d,J= 7.0Hz,2H), 4.6-5.6(b,2H), 6.1-6.4(m,2H), 6.80(d,J= 8.8Hz,1H), 7.2-7.5(m,4H), 7.62(s,1H), 7.83(dd,J=2.0 & 8.8Hz,1H), 8.00(d,J=2.0Hz, 1H) | (neat) 1716, 1607, 1437, 1248, 1153, 1005 | [MS(m/z): 456(M⁺)] |
| 39 (E-107a) | colorless oil | — | (CDCl₃) 3.80(s,3H), 3.83(s, 3H), 3.87(s,3H), 5.10(d,J= 6.8Hz,2H), 4.8-5.6(b,2H), 6.2-7.5(m,8H), 7.77(dd,J= 1.8 & 8.5Hz,1H), 7.99(d,J= 1.8Hz,1H) | (neat) 1713, 1603, 1304, 1246, 1148, 1117, 999 | [MS(m/z): 456(M⁺)] |
| 40 (E-89a) | white amorphous | — | (CDCl₃) 2.32(bs,6H), 3.89 (s,3H), 4.82(d,J=7.0Hz,2H), 4.67-5.71(b,2H), 6.25(t,J= 7.0Hz,1H), 6.71-8.11(m,10H) | (KBr tablet) 2924, 1720, 1607, 1489, 1293, 1232, 1003 | — |
| 41 (E-100a) | colorless oil | — | (CDCl₃) 3.87(s,3H), 4.86(d, J=7.0Hz,2H), 4.6-5.6(b,2H), 5.96(s,2H), 6.25(t,J=7.0Hz, 2H), 6.46(s,1H), 6.80(d,J= 8.6Hz,1H), 7.17-7.51(m,5H), 7.82(dd,J=2.0 & 8.6Hz,1H), 7.84(s,1H), 7.99(d,J=2.0Hz, 1H) | (neat) 1711, 1606, 1464, 1228, 1114, 1004 | [MS(m/z): 440(M⁺)] |
| 42 (E-101a) | pale yellow oil | — | (CDCl₃) 3.84(s,3H), 3.87(s, 3H), 3.92(s,3H), 4.87(d,J= 7.0Hz,2H), 4.80-5.50(b,2H), 6.30(t,J=7.0Hz,1H), 6.53(s, 1H), 6.80(d,J=8.6Hz,1H), 7.26-8.02(m,8H) | — | — |
| 43 (E-108a) | pale yellow oil | — | (CDCl₃) 3.88(s,3H), 4.7-5.5 (b,2H), 4.89(d,J=7.3Hz,1H), 6.21(t,J=7.3Hz,1H), 6.80(d, J=8.6Hz,1H), 7.00(s,1H), 7.19-8.00(m,8H) | (neat) 2878, 1711, 1607, 1488, 1313, 1246, 1118, 1004 | — |
| 44 (E-109a) | colorless oil | — | (CDCl₃) 3.81(s,3H), 4.88(d, J=7.0Hz,2H), 4.75-5.56(b, 2H), 6.28(t,J=7.0Hz,1H), 6.67-8.26(m,14H) | — | — |
| 45 (E-110a) | colorless oil | — | (CDCl₃) 3.84(s,3H), 4.7-5.7 (m,4H), 6.36(t,J=6.9Hz,1H), 6.80(d,J=8.6Hz,1H), 7.1-7.5 (m,5H), 7.81(dd,J=2.2 & 8.6 Hz,1H), 7.92(s,1H), 8.01(d, J=2.2Hz,1H), 8.09(bs,1H), 8.39(dd,J=1.3, 4.8Hz,1H) | — | — |
| 46 (E-113a) | pale yellow oil | — | (CDCl₃) 2.76(s,3H), 3.87(s, 3H), 4.7-5.7(m,4H), 6.12(t, J=6.8Hz,1H), 6.77(d,J=8.6Hz, 1H), 6.85-7.70(m,8H), 7.78 (dd,J=2.2 & 8.6Hz,1H), 7.99 (d,J=2.2Hz,1H) | (KBr tablet) 2926, 1607, 1435, 1246, 1118, 1005 | — |
| 47 (E-114a) | colorless amorphous | — | (CDCl₃) 2.41(s,3H), 3.85(s, 3H), 4.78(d,J=7.2Hz,2H), 4.60-5.64(b,2H), 6.06(t,J= 7.2Hz,1H), 6.63-7.98(m,11H) | (KBr tablet) 2924, 1711, 1606, 1401, 1245, 1118, 1005 | — |
| 48 (E-118a) | colorless oil | — | (CDCl₃) 3.84(s,3H), 4.82-5.69(m,4H), 6.36(t,J=5.4Hz, 1H), 7.19-8.16(m,11H) | — | — |
| 49 | yellow | | (CDCl₃) 3.80(s,3H), 4.79- | — | — |

TABLE 5-3-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| (E-121a) | amorphous | | 5.78(m,4H), 6.38(t,J=6.8Hz, 1H), 6.51-6.88(m,2H), 7.13-7.48(m,5H), 7.61-8.16(m,5H) | | |
| 50 (43a) | colorless oil | — | (CDCl$_3$) 3.87(s,3H), 4.87(d, J=7.0Hz,2H), 4.77-5.62(b, 2H), 6.25(t,J=7.0Hz,1H), 6.82-8.07(m,10H) | — | — |
| 51 (Z-89a) | colorless oil | — | (CDCl$_3$) 2.36(s,6H), 3.89(s, 3H) | (CHCl$_3$) 1714, 1610, 1487, 1245, 1126, 999 | [MS(m/z): 424(M$^+$)] |
| 52 (E-90a) | colorless oil | — | (CDCl$_3$) 2.33(bs,6H), 3.51 (s,2H), 3.65(s,3H), 4.90(d, J=7.5Hz,2H), 5.20(bs,2H), 6.18(t,J=7.5Hz,1H), 6.67-7.55(m,9H), 7.99(s,1H) | (neat) 1738, 1493, 1223, 1160, 1001 | [MS(m/z): 438(M$^+$)] |
| 53 (E-93a) | colorless oil | — | (CDCl$_3$) 2.32 & 2.35(each s, 6H), 3.86(s,3H), 4.86(d,J= 7.1Hz,2H), 5.22(bs,2H), 6.23(t,J=7.1Hz,1H), 6.80(s, 1H), 7.25-7.56(m,8H), 7.72 (s,1H) | (neat) 1715, 1489 1096, 1027 | [MS(m/z): 424(M$^+$)] |
| 54 (E-94a) | white crystal | 202-203 (acetonitrile) | (CDCl$_3$) 2.33(s,6H), 3.93(s, 3H), 4.86(d,J=7.0Hz,2H), 5.22(bs,2H), 6.22(t,J=7.0 Hz, 1H), 6.65-8.15(m,10H) | (KBr tablet) 1721, 1435, 1288, 1262, 1215, 1009 | C$_{27}$H$_{24}$N$_2$O$_3$<br>    C   H   N<br>Found 76.42 5.88 6.51<br>Calcd. 76.39 5.70 6.60 |
| 55 (172a) | pale yellow oil | — | (CDCl$_3$) 2.73-3.48(m,4H), 3.88(s,1H), 3.90(s,2H), 4.82-4.89(m,2H), 6.09(t,J= 7.0Hz,0.7H; Z form), 6.12 (t,J=6.9Hz,0.3H; E form), 6.98-7.45(m,8H), 7.70-8.03 (m,4H) | — | — |
| 56 (173a) | pale yellow oil | — | (CDCl$_3$) 2.34(s,6H), 2.80-3.45(m,4H), 3.89(s,1H), 3.91(s,2H), 4.77-4.85(m, 2H), 6.07(t,J=7.0Hz,0.7H; Z form), 6.08(t,J=7.1Hz, 0.3H; E form), 6.91-8.04(m, 10H) | — | — |
| 57 (177a) | pale yellow oil | — | (CDCl$_3$) 3.91(s,1.5H), 3.93 (s,1.5H), 4.77(dd,J=2.6 & 8.8Hz,1H), 4.85(dd,J=2.6 & 5.5Hz,1H), 5.73(dd,J=1.3 & 5.4Hz,0.5H), 5.82(dd,J=1.6 & 5.1Hz,0.5H), 6.81-8.07 (m,14H) | — | — |
| 58 (178a) | pale yellow oil | — | (CDCl$_3$) 2.32(s,6H), 3.91(s, 1.5H), 4.66-4.84(m,2H), 5.66-5.82(m,1H), 6.89(bs, 2H), 6.95-8.08(m,10H) | — | — |
| 59 (179a) | pale yellow oil | — | (CDCl$_3$) 2.32(s,6H), 3.61(s, 2H), 3.65 & 3.66(each s,1H), 4.67-4.83(m,2H), 5.70(dd, J=5.5 & 8.4Hz,1H), 6.91(bs, 2H), 7.00-7.48(m,9H), 7.70 & 7.73(each s,1H) | — | [MS(m/z): 434(M$^+$)] |

EXAMPLE 60

(Z)-11-[2-(1-Imidazolyl)ethylidene]-6,11-dihydrodibenz[b,e]oxepin-2-carboxylic acid (Compound Z-37b) and (E)-11-[2-(1-imidazolyl)ethylidene]-6,11-dihydrodibenz[b,e]oxepin-2-carboxylic acid 0.2 hydrate (Compound E-37b′):

Compound 37a, 5.9 g, obtained in Example 23 was hydrolyzed in a manner similar to Example 14 to give a mixture (Z/E=1/9) of crude Compounds Z-37b and E-37b.

The mixture was repeatedly washed with hot methanol to give 1.7 g of (E)-11-[2-(1-imidazolyl)ethyliden]-6,11-dihydrodibenz[b,e]oxepin-2-carboxylic acid 0.2 hydrate (Compound E-37b′).

The washing liquid was concentrated and then allowed to stand at room temperature. The precipitated crystals were taken by filtration to give 0.1 g of (Z)-11-[2-(1-imidazolyl)ethylidene]-6,11-dihydrodibenz[b,e]oxepin-2-carboxylic acid (Compound E-37b).

EXAMPLE 61

(E)-11-[2-(1-Benzimidazolyl)ethylidenel-6,11-dihydrodibenz[b,e]oxepin-2-carboxylic acid (Compound E-41b)

Compound E-41a, 12.9 g, obtained in Example 24 was hydrolyzed in a manner similar to Example 15 to give a crude product.

The resulting crude product was recrystallized from isopropanol and then washed with hot methanol to give 10.0 g of the product.

EXAMPLE 62

Sodium (E)-11-[2-(1-benzimidazolyl)ethylidene]-6,11-dihydrodibenz[b,e]oxepin-2-carboxylate 0.6 ethanol 0.6 hydrate (Compound E-41b′)

Compound E-41b, 59.4 g, obtained in Example 61 was suspended in 1.5 l of methanol and 29.9 g of 28% sodium methoxide/methanol solution was added to the suspension followed by stirring at room temperature for 2 hours.

The solvent was distilled off under reduced pressure. The resulting residue was recrystallized from 30 ml of water and 1.2 l of acetone. The crystals were taken by filtration to give a crude product. The crude product was washed with hot methanol to give 64.5 g of the product.

EXAMPLE 63

(E)-11-[2-(4-Phenyl-1-imidazolyl)ethylidene]-6,11-dihydrodibenz[b,e]oxepin-2-carboxylic acid (Compound E-38b)

EXAMPLE 64

(Z,E)-9-Bromo-11-[2-(1-benzimidazolyl)ethylidene]-6,11-dihydrodibenz[b,e]oxepin-2-carboxylic acid monohydrate (Compound 43b′; Z/E=½)

EXAMPLE 65

(E)-11-[2-(5-Fluoro-1-benzimidazolyl)ethylidene]-6,11-dihydrodibenz[b,e]oxepin-2-carboxylic acid (Compound E-49b)

EXAMPLE 66

(E)-11-[2-(6-Fluoro-1-benzimidazolyl)ethylidene]-6,11-dihydrodibenz[b,e]oxepin-2-carboxylic acid (Compound E-50b)

EXAMPLE 67

(E)-11-[2-(5-Trifluoromethyl-1-benzimidazolyl)ethylidene]-6,11-dihydrodibenz[b,e]oxepin-2-carboxylic acid .0.5 isopropanol (Compound E-51b′)

EXAMPLE 68

(E)-11-[2-(6-Trifluoromethyl-1-benzimidazolyl)ethylidene]-6,11-dihydrodibenz[b,e]oxepin-2-carboxylic acid (Compound E-52b)

EXAMPLE 69

(E)-11-[2-(5-Chloro-1-benzimidazolyl)ethylidene]-6,11-dihydrodibenz[b,e]oxepin-2-carboxylic acid .0.5 hydrate (Compound E-53b′)

EXAMPLE 70

(E)-11-[2-(6-Chloro-1-benzimidazolyl)ethylidene]-6,11-dihydrodibenz[b,e]oxepin-2-carboxylic acid .0.25 hydrate (Compound E-54b′)

EXAMPLE 71

(E)-11-[2-(5-Nitro-1-benzimidazolyl)ethylidene]-6,11-dihydrodibenz[b,e]oxepin-2-carboxylic acid .0.2 hydrate (Compound E-55b′)

EXAMPLE 72

(E)-11-[2-(6-Nitro-1-benzimidazolyl)ethylidene]-6,11-dihydrodibenz[b,e]oxepin-2-carboxylic acid (Compound E-56b)

EXAMPLE 73

(E)-11-[2-(5-Methoxy-1-benzimidazolyl)ethylidene]-6,11-dihydrodibenz[b,e]oxepin-2-carboxylic acid (Compound E-61b)

EXAMPLE 74

(E)-11-[2-(6-Methoxy-1-benzimidazolyl)ethylidene]-6,11-dihydrodibenz[b,e]oxepin-2-carboxylic acid (Compound E-62b)

EXAMPLE 75

(E)-11-[2-[5-(1-Phenyl-1-hydroxy)methyl-1-benzimidazolyl]ethylidene]-6,11-dihydrodibenz[b,e]oxepin-2-carboxylic acid .monohydrate (Compound E-81b′)

EXAMPLE 76

(E)-11-[2-[6-(1-phenyl-1-hydroxy)methyl-1-benzimidazolyl]ethylidene]-6,11-dihydrodibenz[b,e]oxepin-2-carboxylic acid .1.5 hydrate (Compound E-82b′)

EXAMPLE 77

(E)-11-[2-(5-Carboxy-1-benzimidazolyl)ethylidene]-6,11-dihydrodibenz[b,e]oxepin-2-carboxylic acid .0.25 hydrate (Compound E-83b′)

EXAMPLE 78

(E)-11-[2-(6-Carboxy-1-benzimidazolyl)ethylidene]-6,11-dihydrodibenz[b,e]oxepin-2-carboxylic acid (Compound E-84b)

EXAMPLE 79

(E)-11-[2-(5,6-Dimethyl-1-benzimidazoly)ethylidene]-6,11-dihydrodibenz[b,e]oxepin-2-carboxylic acid .0.25 hydrate (Compound E-89b′)

In Examples 63 through 79, the products were prepared by hydrolyzing esters of the corresponding oxepine derivative in a manner similar to Example 14 or 15.

EXAMPLE 80

(E)-11-[2-(5,6-Dimethyl-1-benzimidazoly)ethylidene]-6,11-dihydrodibenz[b,e]oxepin-2-carboxylic acid .monohydrochloride .1 isopropanol (Compound E-89b)

Compound E-89b′, 0.5 g, obtained in Example 79 was treated in a manner similar to Example 3 to give 0.5 g of the product.

EXAMPLE 81

Sodium (E)-11-[2-(5,6-Dimethyl-1-benzimidazolyl)ethylidene]-6,11-dihydrodibenz[b,e]oxepin-2-carboxylate .monohydrate (Compound E-89b‴)

Compound E-89b′, 0.5 g, obtained in Example 79 was treated in a manner similar to Example 62 to give 0.3 g of the product.

EXAMPLE 82

(Z)-11-[2-(5,6-Dimethyl-1-benzimidazolyl)ethylidene]-6,11-dihydrodibenz[b,e]oxepin-2-carboxylic acid (Compound Z-89b)

EXAMPLE 83
(E)-11-[2-(5,6-Dimethyl-1-benzimidazolyl)ethylidene]-6,11-dihydrodibenz[b,e]oxepin-2-acetic acid (Compound E-90b)

EXAMPLE 84
(E)-11-[2-(5,6-Dimethyl-1-benzimidazolyl)ethylidene]-6,11-dihydrodibenz[b,e]oxepin-3-carboxylic acid .0.5 isopropanol (Compound E-93b')

EXAMPLE 85
(E)-11-[2-(5,6-Dimethyl-1-benzimidazolyl)ethylidene]-6,11-dihydrodibenz[b,e]oxepin-9-carboxylic acid .0.25 hydrate (Compound E-94b')

EXAMPLE 86
(E)-11-[2-(4,5-Dimethyl-1-benzimidazolyl)ethylidene]-6,11-dihydrodibenz[b,e]oxepin-2-carboxylic acid (Compound E-96b)

EXAMPLE 87
(E)-11-[2-(4,6-Dimethyl-1-benzimidazolyl)ethylidene]-6,11-dihydrodibenz[b,e]oxepin-2-carboxylic acid .0.3 isopropanol (Compound E-99b')

EXAMPLE 88
(E)-11-[2-(5,6-Methylenedioxy-1-benzimidazolyl)ethylidene]-6,11-dihydrodibenz[b,e]oxepin-2-carboxylic acid .0.5 hydrate (Compound E-100b')

EXAMPLE 89
(E)-11-[2-(5,6-Dimethoxy-1-benzimidazolyl)ethylidene]-6,11-dihydrodibenz[b,e]oxepin-2-carboxylic acid (Compound E-101b)

EXAMPLE 90
(E)-11-[2-(4,6-Dimethoxy-1-benzimidazolyl)ethylidene]-6,11-dihydrodibenz[b,e]oxepin-2-carboxylic acid .0.25 hydrate (Compound E-106b')

EXAMPLE 91
(E)-11-[2-(5,7-Dimethoxy-1-benzimidazolyl)ethylidene]-6,11-dihydrodibenz[b,e]oxepin-2-carboxylic acid (Compound E-107b)

EXAMPLE 92
(E)-11-[2-(5,6-Dichloro-1-benzimidazolyl)ethylidene]-6,11-dihydrodibenz[b,e]oxepin-2-carboxylic acid .0.5 acetonitrile .0.25 hydrate (Compound E-108b')

EXAMPLE 93
(E)-11-[2-(1-Naphtho[2,3-d]imidazolyl)ethylidene]-6,11-dihydrodibenz[b,e]oxepin-2-carboxylic acid .0.5 N,N-dimethylformamide .0.25 hydrate (Compound E-109b')

EXAMPLE 94
(E)-11-[2-(4-Aza-1-benzimidazolyl)ethylidene]-6,11-dihydrodibenz[b,e]oxepin-2-carboxylic acid (Compound E-110b)

EXAMPLE 95
(E)-11-[2-(2-Methylthio-1-benzimidazolyl)ethylidene]-6,11-dihydrodibenz[b,e]oxepin-2-carboxylic acid .0.25 hydrate (Compound E-113b')

EXAMPLE 96
(E)-11-[2-(2-Methyl-1-benzimidazolyl)ethylidene]-6,11-dihydrodibenz[b,e]oxepin-2-carboxylic acid (Compound E-114b)

EXAMPLE 97
(E)-11-[2-(1-Benzotriazolyl)ethylidene]-6,11-dihydrodibenz[b,e]oxepin-2-carboxylic acid (Compound E-118b)

EXAMPLE 98
(E)-11-[2-(7-Aza-1-indolyl)ethylidene]-6,11-dihydrodibenz[b,e]oxepin-2-carboxylic acid 1.4 hydrate (Compound E-121b')

In Examples 82 through 98, the products were prepared by hydrolyzing esters of the corresponding oxepine derivatives in a manner similar to Example 14 or 15.

EXAMPLE 99
A 1:1 mixture of (E)-11-[2-(5-methyl-1-benzimidazolyl)ethylidene]-6,11-dihydrodibenz[b,e]oxepin-2-carboxylic acid (Compound E-47b) and
(E)-11-[2-(6-methyl-1-benzimidazolyl)ethylidene]-6,11-dihydrodibenz[b,e]oxepin-2-carboxylic acid (Compound E-48b)

EXAMPLE 100
A 81:19 mixture .0.6 isopropanol of (E)-11-[2-[5-[N-(1-hexyl)carbamoyl]-1-benzimidazolyl]ethylidene]-6,11-dihydrodibenz[b,e]oxepin-2-carboxylic acid (Compound E-85b') and
(E)-11-[2-[6-[N-(1-hexyl)carbamoyl]-1-benzimidazolyl]ethylidene]-6,11-dihydrodibenz[b,e]oxepin-2-carboxylic acid (Compound E-86b')

EXAMPLE 101
A 57:43 mixture of (E)-11-[2-[5-(N-benzylcarbamoyl)-1-benzimidazolyl]ethylidene]-6,11-dihydrodibenz[b,e]oxepin-2-carboxylic acid (Compound E-87b) and
(E)-11-[2-[6-(N-benzylcarbamoyl)-1-benzimidazolyl]ethylidene]-6,11-dihydrodibenz[b,e]oxepin-2-carboxylic acid (Compound E-88b)

In Examples 99 through 101, the products were prepared by hydrolyzing esters of the corresponding oxepine derivatives which is a mixture of position isomers in a manner similar to Example 14 or 15.

EXAMPLE 102
(Z)-5-[2-(1-Benzimidazolyl)ethylidene]-10,11-dihydro-5H-dibenz[a,d]cyclohepten-3-carboxylic acid (Compound Z-172b)

EXAMPLE 103
(E)-5-[2-(5,6-Dimethyl-1-benzimidazolyl)ethylidene]-10,11-dihydro-5H-dibenzo[a,d]cyclohepten-3-carboxylic acid (Compound E-173b) and
(Z)-5-[2-(5,6-Dimethyl-1-benzimidazolyl)ethylidene]-10,11-dihydro-5H-dibenzo]a,d]cyclohepten-3-carboxylic acid (Compound Z-173b)

EXAMPLE 104
(Z,E)-5-[2-(1-Benzimidazolyl)ethylidene]-5H-dibenzo[a,d]cyclohepten-3-carboxylic acid (Compound 177b; Z/E=1/1)

EXAMPLE 105

(E)-5-[2-(5,6-Dimethyl-1-benzimidazolyl)ethylidene]-5H-dibenzo[a,d]cyclohepten-3-carboxylic acid .0.3 isopropanol (Compound E-178b')

EXAMPLE 106

(E)-5-[2-(5,6-Dimethyl-1-benzimidazolyl)ethylidene]-5H-dibenzo[a,d]cyclohepten-3-acetic acid .0.2 hydrate (Compound E-179b')

In Examples 102 through 106, the products were prepared by hydrolyzing esters of corresponding cycloheptene derivatives in a manner similar to Example 14 or 15 and if possible isolating Z-form from E-form of isomers by recrystallization.

Physicochemical properties of the compounds obtained in Examples 60 through 106 are shown in Table 5-4.

TABLE 5-4

| Example No. (Compound No.) | Appearance | MP °C. (Solvent for recrystallization) | NMR (Solvent) δ, ppm | IR (Method) cm$^{-1}$ | Elemental analysis % | | | |
|---|---|---|---|---|---|---|---|---|
| 60 (Z-37b) | white flossy | 284–285 (dec.) (methanol) | (DMSO-d$_6$) 4.99(d,J=6.8Hz, 2H), 5.33(bs,2H), 5.85(t, J=6.8Hz,1H), 6.95(d,J=8.6 Hz, 1H), 6.96(bs,1H), 7.31–7.47(m,5H), 7.73–7.82(m, 2H), 7.83(bs,1H) | (KBr tablet) 3118, 1690, 1605, 1288, 1245, 1099, 1001 | Found Calcd. | C$_{20}$H$_{16}$N$_2$O$_3$ | | |
| | | | | | | C 72.14 72.28 | H 4.84 4.85 | N 8.37 8.43 |
| 60 (E-37b') | white crystal | 264–265 (dec.) (methanol) | (DMSO-d$_6$) 4.50–5.70(m,4H), 6.23(t,J=7.0Hz,1H), 6.84(d, J=8.6Hz,1H), 6.92(bs,1H), 7.17(bs,1H), 7.35–7.59(m, 4H), 7.63(bs,1H), 7.73(dd, J=2.2,8.6Hz,1H), 7.92(d,J= 2.2Hz,1H) | (KBr tablet) 3120, 2336, 1695, 1603, 1455, 827 | Found Calcd. | C$_{20}$H$_{16}$O$_3$.0.2H$_2$O | | |
| | | | | | | C 71.41 71.50 | H 4.90 4.92 | N 8.15 8.34 |
| 61 (E-41b) | white crystal | 249–252 (isopropanol) | (DMSO-d$_6$) 4.6–5.6(m,4H), 6.28(t,J=7.0Hz,1H), 6.81(d, J=8.6Hz,1H), 7.14–7.78(m, 9H), 7.95(d,J=2.2Hz,1H), 8.18(s,1H) | 1004 tablet) 1685, 1606, 1487, 1249, 1004, 773, 744 | Found Calcd. | C$_{24}$H$_{18}$N$_2$O$_3$ | | |
| | | | | | | C 75.35 75.38 | H 4.62 4.74 | N 7.37 7.33 |
| 62 (E-41b') | white crystal | >250 (unclear) (acetone-water) | — | — | Found Calcd. | C$_{14}$H$_{17}$N$_2$O$_3$Na.0.6C$_2$H$_5$OH.0.6H$_2$O | | |
| | | | | | | C 68.28 68.35 | H 4.89 4.96 | N 6.15 6.33 |
| 63 (E-38b) | white crystal | 275–276 (isopropanol) | (DMSO-d$_6$) 4.5–5.8(m,4H), 6.30(t,J=6.8Hz,1H), 6.85(d, J=8.5Hz,1H), 7.14–7.78(m, 12H), 7.95(d,J=1.9Hz,1H) | (KBr tablet) 1608, 1486, 1247, 1004 | Found Calcd. | C$_{26}$H$_{20}$N$_2$O$_3$ | | |
| | | | | | | C 76.40 76.45 | H 4.66 4.94 | N 6.92 6.86 |
| 64 (43b') | white crystal | 262–265 (dec.) (isopropanol) | (DMSO-d$_6$) 4.75–5.60(m,4H), 6.30(t,J=6.6Hz,1H), 6.82(d, J=8.5Hz,1H), 7.16–7.87(m, 8H), 7.93(d,J=2.2Hz,1H), 8.22(s,1H) | — | Found Calcd. | C$_{24}$H$_{17}$BrN$_2$O$_3$.H$_2$O | | |
| | | | | | | C 60.17 60.14 | H 3.67 3.99 | N 5.72 5.84 |
| 65 (E-49b) | white crystal | 174–177 (isopropanol) | (DMSO-d$_6$) 4.8–5.6(m,4H), 6.30(t,J=6.8Hz,1H), 6.83(d, J=8.5Hz,1H), 7.08(dt,J=9.3 & 2.2Hz,1H), 7.23(dd,J=4.7 & 9.0Hz,1H), 7.40–7.56(m, 4H), 7.57–7.62(m,1H), 7.72 (dd,J=2.2 & 8.5Hz,1H), 7.94 (d,J=2.2Hz,1H), 8.26(s,1H) | (KBr tablet) 1690, 1606, 1487, 1243 | Found Calcd. | C$_{24}$H$_{17}$FN$_2$O$_3$ | | |
| | | | | | | C 72.03 71.99 | H 4.48 4.28 | N 7.00 7.00 |
| 66 (E-50b) | white crystal | 287–288 (isopropanol) | (DMSO-d$_6$) 4.7–5.6(m,4H), 6.31(t,J=6.8Hz,1H), 6.83(d, J=8.5Hz,1H), 6.98–7.10(m, 2H), 7.44–7.58(m,3H), 7.58–7.70(m,2H), 7.73(dd,J=2.2 & 8.5Hz,1H), 7.95(d,J=2.2Hz, 1H), 8.20(s,1H) | (KBr tablet) 1690, 1606, 1504; 1485, 1248 | Found Calcd. | C$_{24}$H$_{17}$FN$_2$O$_3$ | | |
| | | | | | | C 71.89 71.99 | H 4.44 4.28 | N 7.18 7.00 |
| 67 (E-51b') | white crystal | 290–291 (dec.) (isopropanol) | (DMSO-d$_6$) 4.7–5.7(m,4H), 6.33(t,J=6.7Hz,1H), 6.83(d, J=8.5Hz,1H), 7.43–7.62(m, 6H), 7.72(dd,J=2.2 & 8.5Hz, 1H), 7.95(d,J=2.2Hz,1H), 8.00(s,1H), 8.41(s,1H) | (KBr tablet) 1695, 1606, 1501, 1325, 1242, 1123, 998 | Found Calcd. | C$_{25}$H$_{17}$F$_3$N$_2$O$_3$.0.5C$_3$H$_8$O | | |
| | | | | | | C 66.49 66.25 | H 4.55 4.41 | N 5.74 5.83 |
| 68 (E-52b) | white crystal | 286–288 (dec.) (isopropanol) | (DMSO-d$_6$) 4.7–5.6(m,4H), 6.34(t,J=7.0Hz,1H), 6.83(d, J=8.5Hz,1H), 7.47–7.63(m, 6H), 7.73(dd,J=2.2 & 8.5Hz, 1H), 7.83(d,J=8.3Hz,1H), 7.96(d,J=2.2Hz,1H), 8.46(s,1H) | (KBr tablet) 1695, 1605, 1345, 1304, 1248, 1117, 1000 | Found Calcd. | C$_{25}$H$_{17}$F$_3$N$_2$O$_3$ | | |
| | | | | | | C 66.85 66.67 | H 3.83 3.80 | N 6.15 6.22 |
| 69 (E-53b') | white crystal | 277–278 (isopro- | (DMSO-d$_6$) 4.7–5.6(m,4H), 6.30(t,J=6.7Hz,1H), 6.83(d, | (KBr tablet) | | C$_{24}$H$_{17}$ClN$_2$O$_3$.0.5H$_2$O | | |
| | | | | | | C | H | N |

TABLE 5-4-continued

| Example No. (Compound No.) | Appearance | MP °C. (Solvent for recrystallization) | NMR (Solvent) δ, ppm | IR (Method) cm⁻¹ | Elemental analysis % | | |
|---|---|---|---|---|---|---|---|
| | | panol) | J=8.5Hz,1H), 7.2-7.75(m, 7H), 7.72(dd,J=2.2 & 8.6Hz, 1H), 7.94(d,J=2.2Hz,1H), 8.27(s,1H) | 1690, 1606, 1488, 1245, 1194, 1004 | Found 67.78 4.01 6.56 Calcd. 67.69 4.26 6.58 | | |
| 70 (E-54b′) | pale yellow crystal | 310–311.5 (isopropanol) | (DMSO-d₆) 4.7–5.6(m,4H), 6.30(t,J=6.7Hz,1H), 6.83(d, J=8.6Hz,1H), 7.15-7.65(m, 7H), 7.73(dd,J=2.2 & 8.5Hz, 1H), 7.95(d,J=2.2Hz,1H), 8.24(s,1H) | (KBr tablet) 1695, 1605, 1488, 1242, 1102, 1001 | $C_{24}H_{17}ClN_2O_3 \cdot 0.25H_2O$ C H N Found 66.58 4.12 6.61 Calcd. 68.40 4.19 6.65 | | |
| 71 (E-55b′) | white crystal | 290–293 (isopropanol-water) | (DMSO-d₆) 4.85–5.6(m,4H), 6.35(t,J=6.7Hz,1H), 6.83(d, J=8.6Hz,1H), 7.46-7.74(m, 6H), 7.95(d,J=2.2Hz,1H), 8.15(dd,J=2.2, 9.0Hz,1H), 8.50-8.53(m,2H) | (KBr tablet) 1677, 1607, 1517, 1346, 1319, 1286, 1247, 1004 | $C_{24}H_{17}N_3O_5 \cdot 0.2H_2O$ C H N Found 66.85 3.88 9.61 Calcd. 66.88 4.07 9.75 | | |
| 72 (E-56b) | white crystal | 287–290 (isopropanol) | (DMSO-d₆) 4.8–5.6(m,4H), 6.34(t,J=6.8Hz,1H), 6.83 (d,J=8.5Hz,1H), 7.48-8.10 (m,9H), 8.58(s,1H) | (KBr tablet) 1690, 1604, 1520, 1486, 1343, 1240, 1201 | $C_{24}H_{17}N_3O_5$ C H N Found 66.17 3.89 9.95 Calcd. 67.44 4.01 9.83 | | |
| 73 (E-61b) | white crystal | 257–258 (methanol) | (DMSO-d₆) 3.77(s,3H), 4.8–5.6(m,4H), 6.27(t,J=6.8Hz, 1H), 6.82(d,J=8.5Hz,1H), 6.82-7.62(m,6H), 7.16(bs, 1H), 7.72(dd,J=2.2, 8.5Hz, 1H), 7.93(d,J=2.2Hz,1H), 8.11(bs,1H) | (KBr tablet) 3450, 1715, 1602, 1488, 1243, 837, 770 | $C_{25}H_{20}N_2O_4 \cdot 0.2H_2O$ C H N Found 72.35 4.78 6.73 Calcd. 72.17 4.94 6.73 | | |
| 74 (E-62b) | white crystal | 272–273 (methanol) | (DMSO-d₆) 3.73(s,3H), 6.30 (t,J=7.0Hz,1H), 6.71(d,J= 2.2Hz,1H), 6.82(dd,J=2.2, 8.5Hz,1H), 6.83(d,J=8.5Hz, 1H), 7.46-7.62(m,5H), 7.72 (dd,J=2.2, 8.5Hz,1H), 7.96 (d,J=2.2Hz,1H), 8.10(bs,1H) | (KBr tablet) 3450, 1680, 1605, 1505, 1245, 1002, 815, 772 | $C_{25}H_{20}N_2O_4 \cdot 0.3H_2O$ C H N Found 70.86 4.69 6.67 Calcd. 70.74 5.07 6.60 | | |
| 75 (E-81b′) | white crystal | 182–184 (acetonitrile) | (DMSO-d₆) 4.6–5.6(m,4H), 5.79(s,1H), 6.25(t,J=6.7Hz, 1H), 6.82(d,J=8.5Hz,1H), 7.1-7.65(m,12H), 7.71(dd, J=2.1 & 8.5Hz,1H), 7.92(d, J=2.1Hz,1H), 8.17(s,1H) | (KBr tablet) 1690, 1605, 1491, 1245, 1004 | $C_{31}H_{24}N_2O_4 \cdot H_2O$ C H N Found 73.74 5.01 5.35 Calcd. 73.50 5.17 5.53 | | |
| 76 (E-82b′) | white crystal | 270–271 (dec.) (acetonitrile) | (DMSO-d₆) 4.65–5.80(m,4H), 6.23(t,J=6.7Hz,1H), 6.85 (d,J=8.5Hz,1H), 7.10-7.70 (m,12H), 7.73(dd,J=2.1 & 8.5Hz,1H), 7.94(d,J=2.1Hz, 1H), 8.20(s,1H) | (KBr tablet) 1690, 1605, 1487, 1451, 1242, 1000 | $C_{31}H_{24}N_2O_4 \cdot 1.5H_2O$ C H N Found 72.02 5.05 5.11 Calcd. 72.22 5.28 5.43 | | |
| 77 (E-83b′) | white crystal | 318–319 (dec.) (isopropanol) | (DMSO-d₆) 4.7–5.7(m,4H), 6.32(t,J=6.7Hz,1H), 6.83(d, J=8.6Hz,1H), 7.28(d,J=8.3 Hz,1H), 7.4-7.65(m,4H), 7.72(dd,J=2.2 & 8.6Hz,1H), 7.85(d,J=8.3Hz,1H), 7.95(d, J=2.2Hz,1H), 8.23(s,1H), 8.34(s,1H) | (KBr tablet) 1683, 1608, 1316, 1269, 1249, 1003 | $C_{25}H_{18}N_2O_5 \cdot 0.25H_2O$ C H N Found 69.45 4.33 6.32 Calcd. 69.68 4.33 6.50 | | |
| 78 (E-84b) | white crystal | 321–323 (dec.) (ethanol) | (DMSO-d₆) 4.7–5.7(m,4H), 6.28(t,J=6.8Hz,1H), 6.83(d, J=8.5Hz,1H), 7.4-7.85(m, 8H), 7.95(d,J=2.2Hz,1H), 8.41(s,1H) | (KBr tablet) 1686, 1608, 1311, 1265, 1243, 1122, 1006 | $C_{25}H_{18}N_2O_5$ C H N Found 70.54 4.27 6.28 Calcd. 70.42 4.25 6.57 | | |
| 79 (E-89b′) | white crystal | 275–277 (isopropanol-water) | (DMSO-d₆) 2.25(s,3H), 2.28 (s,3H), 2.48-2.51(m,2H), 4.8-5.4(m,4H), 6.24(t,J= 7.0Hz,1H), 6.80(s,1H), 6.82 (d,J=8.5Hz,1H), 7.38(s,1H), 7.45-7.65(m,4H), 7.71(dd, J=2.2, 8.5Hz,1H), 7.93(d, J=2.2Hz,1H), 8.02(s,1H) | (KBr tablet) 1683, 1606, 1488, 1244, 1002 | $C_{26}H_{22}N_2O_3 \cdot 0.25H_2O$ C H N Found 75.23 5.29 6.73 Calcd. 75.25 5.46 6.75 | | |
| 80 (E-89b″) | white crystal | 235–237 (isopropanol) | — | — | $C_{26}H_{22}N_2O_3 \cdot C_3H_8O \cdot HCl$ C H N Found 68.41 5.98 5.73 Calcd. 68.42 6.14 5.50 | | |

TABLE 5-4-continued

| Example No. (Compound No.) | Appearance | MP °C. (Solvent for recrystallization) | NMR (Solvent) δ, ppm | IR (Method) cm⁻¹ | Elemental analysis % |
|---|---|---|---|---|---|
| 81 (E-89b''') | white crystal | 241-242 (water) | — | — | $C_{26}H_{21}N_2O_3Na \cdot 1.5H_2O$<br>　　C　　H　　N<br>Found　68.19　5.04　5.87<br>Calcd.　67.96　5.27　6.10 |
| 82 (Z-89b) | white crystal | 281.5-283 (dec.) (isopropanol) | (DMSO-d₆) 2.29 & 2.31(each s, 6H), 5.1-5.5(m,4H), 5.81(t, J=6.6Hz,1H), 7.02(d,J=9.3 Hz,1H), 7.22(bs,1H), 7.30-7.45(m,5H), 7.82-7.86(m, 2H), 8.18(bs,1H) | (KBr tablet) 1680, 1608, 1495, 1303, 1244, 1106, 999 | $C_{26}H_{22}N_2O_3 \cdot 0.5H_2O$<br>　　C　　H　　N<br>Found　74.82　5.51　6.50<br>Calcd.　74.45　5.53　6.68 |
| 83 (E-90b) | white solid | 277.5-278 (isopropanol)* | (DMSO-d₆) 2.24 & 2.27(each s,6H), 3.48(s,2H), 4.6-5.5 (m,4H), 6.14(t,J=7.0Hz,1H), 6.69(d,J=8.5Hz,1H), 6.78(s, 1H), 7.06(dd,J=2.2 & 8.6Hz, 1H), 7.22(s,1H), 7.40(s, 1H), 7.41-7.65(m,4H), 8.08 (s,1H) | (KBr tablet) 1708, 1489, 1224, 1010 | $C_{27}H_{24}N_2O_3$<br>　　C　　H　　N<br>Found　76.16　5.92　5.68<br>Calcd.　76.39　5.70　6.60 |
| 84 (E-93b') | white crystal | 267-268 (dec.) (ethanol-isopropanol) | (DMSO-d₆) 2.25 & 2.28(each s,6H), 4.6-5.6(m,4H), 6.28 (t,J=7.0Hz,1H), 6.81(s,1H), 7.26(s,1H), 7.40-7.67(m, 7H), 8.08(s,1H) | (KBr tablet) 1692, 1411, 1312, 1025 | $C_{26}H_{22}N_2O_3 \cdot 0.5C_3H_8O$<br>　　C　　H　　N<br>Found　74.84　5.77　6.08<br>Calcd.　74.98　5.95　6.36 |
| 85 (E-94b') | white crystal | 290.5-292 (dec.) (dioxane) | (DMSO-d₆) 4.8-5.4(m,4H), 6.23(d,J=6.9Hz,1H), 6.75-7.25(m,4H), 7.34(dd,J=1.6 & 7.8Hz,1H), 7.40(bs,1H), 7.74(d,J=7.8Hz,1H), 7.93(s, 1H), 8.01-8.06(m,2H) | (KBr tablet) 1683, 1480, 1285, 1268, 1217, 1007 | $C_{26}H_{22}N_2O_3 \cdot 0.25H_2O$<br>　　C　　H　　N<br>Found　75.56　5.31　6.63<br>Calcd.　75.25　5.47　6.75 |
| 86 (E-96b) | white crystal | 302-306 (toluene) | (DMSO-d₆) 2.32(s,3H), 2.45 (s,3H), 4.80-5.30(b,2H), 6.27(t,J=6.8Hz,1H), 6.83(d, J=8.6Hz,1H), 6.92 & 7.05 (ABq,J=8.2Hz,2H), 7.46-7.63 (m,6H), 7.23(dd,J=2.2 & 8.6 Hz,1H), 7.93(d,J=2.2Hz,1H), 8.31(s,1H) | (KBr tablet) 3420, 1673, 1605, 1503, 1227, 1001 | $C_{26}H_{22}N_2O_3$<br>　　C　　H　　N<br>Found　75.87　5.24　6.43<br>Calcd.　76.08　5.40　6.82 |
| 87 (E-99b') | white crystal | 308-311 (isopropanol-methanol-water) | (Pyridine-d₅) 2.37(s,3H), 2.77(s,3H), 4.80-4.93(b, 2H), 4.85-5.69(m,2H), 6.26 (t,J=7.1Hz,1H), 6.70(s,1H), 6.98(s,1H), 7.10(d,J=8.9Hz, 1H), 7.20-7.56(m,4H), 8.15 (s,1H), 8.25(dd,J=2.2 & 8.6 Hz,1H), 8.45(d,J=2.0Hz,1H) | (KBr tablet) 3420, 1673, 1605, 1504, 1309, 1227, 1200, 1001 | $C_{26}H_{22}N_2O_3 \cdot 0.3C_3H_8O$<br>　　C　　H　　C<br>Found　75.36　5.42　6.18<br>Calcd.　75.40　5.70　6.52 |
| 88 (E-100b') | white crystal | 273 (dec.) (isopropanol) | (DMSO-d₆) 4.6-5.6(m,4H), 5.99(s,2H), 6.26(t,J=6.7Hz, 1H), 6.78(s,1H), 6.84(d,J= 8.5Hz,1H), 7.13(s,1H), 7.4-7.65(m,4H), 7.73(dd,J=2.2 & 8.5Hz,1H), 7.93(d,J=2.2Hz, 1H), 7.99(s,1H) | (KBr tablet) 1689, 1606, 1486, 1350, 1244, 1001 | $C_{25}H_{18}N_2O_5 \cdot 0.5H_2O$<br>　　C　　H　　C<br>Found　68.83　4.69　6.12<br>Calcd.　68.95　4.40　6.43 |
| 89 (E-101b) | white crystal | 290-292 (partially dec.) (isopropanol) | (DMSO-d₆) 3.72(s,3H), 3.77 (s,3H), 4.70-5.7(m,4H), 6.31(t,J=6.8Hz,1H), 6.74(s, 1H), 6.84(d,J=8.5Hz,1H), 7.19(s,1H), 7.45-7.64(m, 4H), 7.73(dd,J=2.0 & 8.5Hz, 1H), 7.95(d,J=2.0Hz,1H), 8.04(s,1H) | (KBr tablet) 2942, 2838, 1697, 1606, 1492, 1229, 1001 | $C_{26}H_{22}N_2O_5$<br>　　C　　H　　C<br>Found　70.25　5.03　6.36<br>Calcd.　70.58　5.01　6.33 |
| 90 (E-106b') | white solid | 259-261 (dec.) (acetonitrile)* | (DMSO-d₆) 3.69 & 3.89(each s,6H), 4.5-5.8(m,4H), 6.24-6.32(m,3H), 6.83(d,J=8.5 Hz,1H), 7.43-7.60(m,3H), 7.61(d,J=5.4Hz,1H), 7.72 (dd,J=2.0 & 8.5Hz,1H), 7.94 (s,2H) | (KBr tablet) 1606, 1505, 1248, 1205, 1150, 1006 | $C_{26}H_{22}N_2O_5 \cdot 0.25H_2O$<br>　　C　　H　　N<br>Found　70.06　4.89　6.26<br>Calcd.　69.87　5.07　6.27 |
| 91 (E-107b) | white solid | 278-279 (dec.) (acetonitrile)* | (DMSO-d₆) 3.61 & 3.75(each s,6H), 4.9-5.7(m,4H), 6.18 (t,J=6.5Hz,1H), 6.37(bs, 1H), 6.73(bs,1H), 6.81(d,J= 8.6Hz,1H), 7.37-7.63(m,4H), 7.70(dd,J=2.2 & 8.6Hz,1H), | (KBr tablet) 1700, 1608, 1500, 1307, 1255, 1122, 1003 | $C_{26}H_{22}N_2O_5$<br>　　C　　H　　N<br>Found　69.60　4.90　6.12<br>Calcd.　69.87　5.07　6.27 |

TABLE 5-4-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 92 (E-108b') | white crystal | 287–289 (acetonitrile-isopropanol) | 7.92(d,J=2.2Hz,1H), 8.06 (bs,1H) (DMSO-d$_6$) 4.7–5.6(m,4H), 6.83(d,J=8.5Hz,1H), 7.44 (s,1H), 7.46–7.63(m,4H), 7.73(dd,J=2.2, 8.5Hz,1H), 7.89(s,1H), 7.95(d,J=2.2Hz, 1H), 8.31(s,1H) | (KBr tablet) 1698, 1607, 1488, 1312, 1262, 996, 765 | C$_{24}$H$_{16}$Cl$_2$N$_2$O$_3$·0.5C$_2$H$_3$N·0.25H$_2$O<br>　　C　　H　　N<br>Found　63.10　3.56　7.19<br>Calcd.　63.04　3.81　7.35 |
| 93 (E-109b') | white crystal | 287–290 (dec.) (N,N-dimethylformamide) | (DMSO-d$_6$) 4.8–5.6(m,4H), 6.37(t,J=6.8Hz,1H), 6.83(d, J=8.6Hz,1H), 7.37–8.03(m, 11H), 8.21(s,1H), 8.46(s, 1H), 12.7(bs,1H) | (KBr tablet) 1676, 1602, 1514, 1382, 1244, 1194, 1005 | C$_{28}$H$_{20}$N$_2$O$_3$·0.5C$_3$H$_7$NO·0.25H$_2$O<br>　　C　　H　　N<br>Found　74.83　5.02　7.74<br>Calcd.　74.82　5.11　7.39 |
| 94 (E-110b) | white crystal | 260–263 (dec.) (isopropanol) | (DMSO-d$_6$) 4.8–5.4(m,4H), 6.31(t,J=5.2Hz,1H), 6.83(d, J=8.5Hz,1H), 7.27(dd,J=4.8 & 8.1Hz,1H), 7.44–7.58(m, 4H), 7.71(dd,J=2.2 & 8.5Hz, 1H), 7.90(d,J=2.2Hz,1H), 8.06(d,J=7.2Hz,1H), 8.33 (dd,J=1.2 & 4.8Hz,1H), 8.49 (bs,1H) | (KBr tablet) 1683, 1605, 1505, 1412, 1393, 1313, 1247, 1206, 1000, 772 | C$_{23}$H$_{17}$N$_3$O$_3$<br>　　C　　H　　N<br>Found　71.92　4.31　10.94<br>Calcd.　72.05　4.47　10.96 |
| 95 (E-113b') | white crystal | 234–236 (dec.) (isopropanol) | (DMSO-d$_6$) 2.67(s,3H), 4.5–5.7(m,4H), 6.06(t,J=6.6 Hz,1H), 6.84(d,J=8.5Hz,1H), 7.13–7.65(m,8H), 7.72(dd,J= 2.2 & 8.5Hz,1H), 7.93(d,J= 2.2Hz,1H) | (KBr tablet) 2928, 1685, 1608, 1488, 1450, 1314, 1232, 1008, 774, 742 | C$_{26}$H$_{22}$N$_2$O$_3$S·0.25H$_2$O<br>　　C　　H　　N<br>Found　69.33　4.57　6.39<br>Calcd.　69.35　4.71　6.47 |
| 96 (E-114b) | white crystal | 318 (dec.) (isopropanol) | (DMSO-d$_6$) 2.39(s,3H), 4.6–5.6(m,4H), 6.17(t,J=6.7 Hz,1H), 6.83(d,J=8.5Hz,1H), 7.12–7.16(m,3H), 7.50–7.66 (m,5H), 7.72(dd,J=2.1 & 8.5 Hz,1H), 7.96(d,J=2.1Hz,1H) | (KBr tablet) 1695, 1606, 1487, 1404, 1310, 1240, 1001 | C$_{25}$H$_{20}$N$_2$O$_3$<br>　　C　　H　　N<br>Found　75.76　5.05　7.00<br>Calcd.　75.74　5.09　7.06 |
| 97 (E-118b) | white crystal | 215–219 (isopropanol-water) | (DMSO-d$_6$) 5.0–5.7(m,4H), 6.40(t,J=7.0Hz,1H), 6.85(d, J=8.5Hz,1H), 7.38–7.76(m, 8H), 7.93(d,J=2.0Hz,1H), 8.05(d,J=8.5Hz,1H), 12.76 (bs,1H) | (KBr tablet) 1686, 1604, 1407, 1306, 1261, 1248, 996, 747 | C$_{23}$H$_{17}$N$_3$O$_3$<br>　　C　　H　　N<br>Found　72.19　4.45　11.20<br>Calcd.　72.05　4.47　10.96 |
| 98 (E-121b') | white crystal | 201–203 (isopropanol)* | (DMSO-d$_6$) 5.05–5.65(m,4H), 6.30(t,J=6.3Hz,1H), 6.62(d, J=2.2Hz,1H), 6.81(d,J=8.6 Hz,1H), 7.1–7.75(m,7H), 7.95(d,J=2.2Hz,1H), 8.09(d, J=5.9Hz,1H), 8.24(d,J=6.6 Hz,1H) | (KBr tablet) 1608, 1481, 1373, 1313, 1285, 1101, 1009 | C$_{24}$H$_{18}$N$_2$O$_3$·1.4H$_2$O<br>　　C　　H　　N<br>Found　70.63　4.87　6.85<br>Calcd.　70.72　5.14　6.87 |
| 99 (mixture of E-47b and E-48b) | white crystal | 291–295 (toluene) | (Pyridine-d$_5$) 2.36(s,1.5H), 2.40(s,1.5H), 4.85–5.10(m, 2H), 4.80–5.64(m,2H), 6.26 (t,J=7.2Hz,1H), 6.85(s,1H), 7.00(d,J=8.6Hz,1H), 7.12–7.58(m,6H), 8.22(s,1H), 8.24(dd,J=2.2 & 8.6Hz,1H), 8.44(d,J=2.2Hz,1H) | (KBr tablet) 3450, 1683, 1608, 1505, 1243, 1007, 775 | C$_{25}$H$_{20}$N$_2$O$_3$<br>　　C　　H　　N<br>Found　74.90　4.92　6.84<br>Calcd.　74.74　5.08　7.07 |
| 100 (mixture of E-85b' and E-86b') | white solid | 226–228 (isopropanol) | (DMSO-d$_6$) 0.8–1.6(m,11H), 3.2–3.3(m,2H), 4.80–5.65(m, 4H), 6.31(t,J=6.8Hz,1H), 6.83(d,J=8.5Hz,1H), 7.2–7.8 (m,7H), 7.94(d,J=2.2Hz,1H), 8.19–8.38(m,3H) | (KBr tablet) 1694, 1611, 1223, 1130, 1004 | C$_{31}$H$_{31}$N$_3$O$_4$·0.6C$_3$H$_8$O<br>　　C　　H　　N<br>Found　72.40　6.73　7.38<br>Calcd.　72.33　6.44　7.71 |
| 101 (mixture of E-87b and E-88b) | white solid | 251–255 (isopropanol) | (DMSO-d$_6$) 4.51(t,J=6.6Hz, 2H), 4.7–5.7(m,4H), 6.26–6.35(m,1H), 6.84(d,J=8.8Hz, 1H), 7.22–8.36(m,14H), 7.95 (d,J=2.2Hz,1H), 8.98–9.05 (m,1H) | (KBr tablet) 1670, 1631, 1317, 1246, 1205, 1006 | C$_{32}$H$_{25}$N$_3$O$_4$<br>　　C　　H　　N<br>Found　74.62　4.61　7.85<br>Calcd.　74.55　4.89　8.15 |
| 102 (Z-172b) | white crystal | 303–308 (isopropanol) | (DMSO-d$_6$) 2.70–3.42(m,4H), 5.00–5.30(m,2H), 6.04(t,J= 7.0Hz,1H), 7.03–7.43(m,9H), 8.00–8.08(m,1H), 8.31(s, 2H), 8.36(dd,J=1.3 & 7.9Hz,1H) | (KBr tablet) 1716, 1670, 1493, 1288, 1103 | C$_{25}$H$_{20}$N$_2$O$_2$<br>　　C　　H　　N<br>Found　78.91　5.21　7.40<br>Calcd.　78.93　5.30　7.36 |
| 103 | white | 262–266 | (Pyridine-d$_5$) 2.28(s,6H), | (KBr tablet) | C$_{27}$H$_{24}$N$_2$O$_2$ |

TABLE 5-4-continued

| Example No. (Compound No.) | Appearance | MP °C. (Solvent for recrystallization) | NMR (Solvent) δ, ppm | IR (Method) cm$^{-1}$ | Elemental analysis % | | | |
|---|---|---|---|---|---|---|---|---|
| (E-173b) | crystal | (isopropanol) | 2.65–2.87(m,2H), 3.02–3.34 (m,2H), 4.55–4.86(m,2H), 6.02(t,J=4.2Hz,1H), 6.87–7.78(m,7H), 8.14(s,1H), 8.43(dd,J=1.7 & 8.0Hz,1H), 8.61(d,J=1.1Hz,1H) | 3430, 1678, 1454, 1256, 1210 | Found Calcd. | C 79.21 79.39 | H 5.86 5.92 | N 6.91 6.86 |
| 103 (Z-173b) | white crystal | 288–289 (isopropanol) | (Pyridine-d$_5$) 2.30(s,3H), 2.33(s,3H), 2.73–3.00(m, 2H), 3.12–3.44(m,2H), 4.80–5.20(m,2H), 6.04(t,J=4.2Hz, 1H), 7.05–7.58(m,7H), 8.20 (s,1H), 8.33(d,J=1.7Hz,1H), 8.38(dd,J=1.7 & 8.6Hz,1H) | (KBr tablet) 3430, 1678, 1454, 1256, 1210 | Found Calcd. | $C_{27}H_{24}N_2O_2$ C 79.40 79.39 | H 5.89 5.92 | N 6.88 6.86 |
| 104 (177b) | white crystal | 263–265 (isopropanol) | (Pyridine-d$_5$) 4.70–5.00(m, 2H), 5.50–5.83(m,1H), 6.90–7.00(m,2H), 7.05–7.48(m, 7H), 7.53–7.79(m,2H), 8.01 (s,1H) | (KBr tablet) 3420, 1695, 1494, 1250, 1183 | Found Calcd. | $C_{25}H_{18}N_2O_2$ C 79.10 79.35 | H 4.58 4.79 | N 7.66 7.40 |
| 105 (E-178b') | white crystal | 306–308 (isopropanol) | (Pyridine-d$_5$) 2.26(s,3H), 2.31(s,3H), 4.70(dd,J=9.6 & 15.6Hz,1H), 4.95(dd,J=4.2 & 15.6Hz,1H), 5.71(dd,J=4.2 & 9.6Hz,1H), 6.98–7.56(m,6H), 7.74(s,1H), 8.11(s,1H), 8.35(dd,J=1.7 & 8.0Hz,1H), 8.45(d,J=1.7Hz,1H) | (KBr tablet) 3450, 1678, 1504, 1454, 1280, 1210, 769 | Found Calcd. | $C_{27}H_{22}N_2O_2 \cdot 0.3 C_3H_8O$ C 78.89 78.94 | H 5.51 5.79 | N 5.99 6.39 |
| 106 (E-179b') | white crystal | 280–283 (isopropanol) | (DMSO-d$_6$) 2.25(s,6H), 3.60 (s,2H), 4.59(dd,J=9.5 & 15.4 Hz,1H), 5.04(dd,J=4.6 & 15.4 Hz,1H), 5.60(dd,J=4.6 & 9.5 Hz,1H), 6.74(s,1H), 6.93 & 7.04(ABq,J=12.0Hz,2H), 7.35 (s,1H), 7.20–7.60(m,7H), 8.04(s,1H) | (KBr tablet) 3406, 2924, 1707, 1496, 1287 | Found Calcd. | $C_{28}H_{24}N_2O_2 \cdot 0.2H_2O$ C 79.42 79.56 | H 5.97 5.75 | N 6.48 6.26 |

EXAMPLE 107

5-[2-(5,6-Dimethyl-1-benzimidazolyl)ethyl]-10,11-dihydro-5H-dibenzo[a,d]cyclohepten-3-carboxylic acid .0.1 hydrate (Compound 174b')

5-(2-Hydroxyethyl)-3-(4,4-dimethyl-2-oxazoline-2-yl)-10,11-dihydro-5H-dibenzo[a,d]cycloheptene (Compound s), 0.32 g, obtained in Reference Example 19 was dissolved in 9.6 ml of methylene chloride, and 3.2 ml of triethylamine and 0.2 ml of methanesulfonyl chloride were successively added to the solution. The mixture was stirred for 1.5 hours at room temperature, and extracted with 100 ml of methylene chloride. The extract was washed with 1N hydrochloric acid aqueous solution, saturated sodium bicarbonate aqueous solution and saturated sodium chloride aqueous solution successively, and dried over anhydrous magnesium sulfate. The solvent was distilled off under reduced pressure to obtain the corresponding methanesulfonyloxy compound as a crude product. The crude product was served as it is for further reaction.

5,6-Dimethylbenzimidazole, 0.21 g, and 62 mg of sodium hydride (oily: 60%) were dissolved in 15 ml of tetrahydrofuran and 2.5 ml of N,N-dimethylformamide. To the solution was dropwise added the crude methanesulfonyloxy compound dissolved in 10 ml of tetrahydrofuran, and the mixture was heated under reflux for 4 hours. The mixture was extracted with 100 ml of ethyl acetate and washed successively with saturated sodium bicarbonate aqueous solution and saturated sodium chloride aqueous solution. The mixture was dried over anhydrous magnesium sulfate, and the solvent was distilled off under reduced pressure. The resulting residue was subjected to silica gel column chromatography (eluting solvent; ethyl acetate:triethylamine = 10:1) to give 0.47 g of 5-[2-(5,6-dimethyl-1-benzimidazolyl)ethyl]-3-(4,4-dimethyl-2-oxazoline-2-yl)-10,11-dihydro-5H-dibenzo[a,d]cycloheptene as pale yellow oily.

The above-mentioned compound, 0.36 g was dissolved in a solvent mixture of 18 ml of dioxane and 18 ml of water, and 0.36 ml of concentrated sulfuric acid was added thereto. The mixture was stirred at 60°–80° C. for 1.5 hours, and water was added thereto. The mixture was washed with ether, and adjusted to pH6 with 10N sodium hydroxide aqueous solution. The precipitated solid was taken off by filtration to give 0.19 g of the desired product.

EXAMPLE 108

5-[2-(5,6-Dimethyl-1-benzimidazolyl)ethyl]-5H-dibenzo[a,d]cyclohepten-3-carboxylic acid .0.8 isopropanol .monohydrate (Compound 180b')

The product was prepared using Compound v obtained in Reference Example 22 in a manner similar to Example 107.

The physicochemical properties or the compounds obtained in Examples 107 and 108 are shown in Table 5-5.

TABLE 5-5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 107 (174b') | white crystal | 232–235 (isopropanol) | (DMSO-d$_6$) 2.29(s,6H), 2.53–2.73(m,2H), 2.93–3.40(m, 4H), 4.08–4.23(m,2H), 4.23–4.37(m,1H), 7.08(s,1H), 7.14–7.26(m,5H), 7.40(s, 1H), 7.70(dd,J=1.7 & 7.8Hz, 1H), 7.82(d,J=1.5Hz,1H), 7.99(s,1H) | (KBr tablet) 3450, 2922, 1692, 1657, 1496, 1254, 1205 | $C_{27}H_{26}N_2O_2.0.1H_2O$<br>  C    H    N<br>Found 78.53 6.35 6.91<br>Calcd. 78.65 6.40 6.79 |
| 108 (180b') | yellow solid | 302–306 (isopropanol)* | (DMSO-d$_6$) 2.10–2.22(m,2H), 2.28(s,6H), 3.79–3.84(m, 2H), 4.30(t,J=7.8Hz,1H), 7.03 & 7.10(ABq,J=12.0Hz, 2H), 7.00–7.56(m,7H), 7.79–8.06(m,3H) | (KBr tablet) 3440, 2922, 1689, 1652, 1498, 1264 | $C_{27}H_{24}N_2O_2.0.4C_3H_8O.H_2O$<br>  C    H    N<br>Found 75.31 6.19 6.54<br>Calcd. 75.17 6.53 6.21 |

EXAMPLE 109

Methyl 11-(4-pyridyl)thio-6,11-dihydrodibenz[b,e]oxepin-2-carboxylate (Compound 8a)

Methyl 11-hydroxy-6,11-dihydrodibenz[b,e]oxepin-2-carboxylate (Compound b), 4.0 g, obtained in Reference Example 2 was dissolved in 200 ml of methylene chloride and 2.5 ml of trifluoroacetic anhydride was added to the solution. The mixture was stirred at room temperature for an hour. Further 2.5 g of 4-mercaptopyridine and 1 ml of boron trifluoride diethyl ether complex were added to the reaction mixture followed by stirring at room temperature for 2 hours. Then, crushed small ice pieces were added to the mixture. After stirring for an hour, the solvent was distilled off under reduced pressure. The aqueous phase was extracted with 300 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=10:10:1) to give 2.9 g of the product.

EXAMPLE 110

Methyl 11-(4-pyridyl)thio-6,11-dihydrodibenz[b,e]oxepin-2-carboxylate monofumarate (Compound 8a')

Compound 8a, 1.2 g, obtained in Example 109 was treated in a manner similar to Example 10 to give 1.2 g of the objective compound.

EXAMPLE 111

Methyl 11-[(3-pyridyl)methyl]thio-6,11-dihydrodibenz[b,e]oxepin-2-carboxylate (Compound 14a)

EXAMPLE 112

Methyl 11-[(3-pyridyl)methyl]thio-6,11-dihydrodibenz[b,e]oxepin-3-carboxylate (Compound 15a)

EXAMPLE 113

Methyl 11-(benzyl)thio-6,11-dihydrodibenz[b,e]oxepin-2-carboxylate (Compound 19a)

EXAMPLE 114

Methyl 11-(benzyl)thio-6,11-dihydrodibenz[b,e]oxepin-2-acetate (Compound 20a)

EXAMPLE 115

Methyl 11-(2-benzothiazolyl)thio-6,11-dihydrodibenz[b,e]oxepin-2-acetate (Compound 126a)

EXAMPLE 116

Methyl 11-[2-(2-benzimidazolyl)ethyl]thio-6,11-dihydrodibenz[b,e]oxepin-2-carboxylate (Compound 129a)

EXAMPLE 117

Methyl 11-[2-(1-methyl-2-benzimidazolyl)ethyl]thio-6,11-dihydrodibenz[b,e]oxepin-2-carboxylate (Compound 130a)

EXAMPLE 118

Methyl 11-[2-[1-(4-methoxy)benzyl-2-benzimidazolyl]ethyl]thio-6,11-dihydrodibenz[b,e]oxepin-2-carboxylate (Compound 132a)

EXAMPLE 119

Methyl 11-(5-mercapto-1,3,4-thiadiazol-2-yl)thio-6,11-dihydrodibenz[b,e]oxepin-2-carboxylate (Compound 153a)

In Examples 111 through 119, the objective compounds were prepared in a manner similar to Example 109, using the corresponding 11-hydroxy- or 11-methoxy-6,11-dihydrodibenz[b,e]oxepin derivative (Compound b, f and p) and thiol compounds.

EXAMPLE 120

Methyl 11-(5-octadecylthio-1,3,4-thiadiazol-2-yl)thio-6,11-dihydrodibenz[b,e]oxepin-2-carboxylate (Compound 154a)

After 50 ml of an N,N-dimethylformamide solution containing a mixture of 2.0 g of Compound 153a obtained in Example 119, 2 ml of octadecyl bromide and 2.0 g of potassium carbonate was stirred at 80° C. at 1.5 hours, the solvent was distilled off under reduced pressure. The aqueous phase was extracted with 200 ml of methylene chloride. The extract was washed with saturated sodium chloride aqueous solution. After drying over anhydrous sodium sulfate, the solvent was distilled off under reduced pressure. The resulting residue was subjected to silica gel column chromatography (eluting solvent; hexane:ethyl acetate=15:1) to give 0.8 g of the product.

EXAMPLE 121

Methyl 11-phenylsulfonyl-6,11-dihydrodibenz[b,e]oxepin-2-carboxylate (Compound 157a)

Compound b, 10 g, 15 g of sodium benzenesulfinate dihydrate and 25 ml of trifluoroacetic anhydride were treated in a manner similar to Example 109 to give 14.3 g of the objective compound.

EXAMPLE 122

Methyl 11-[(3-pyridyl)methyl]thio-6,11-dihydrodibenzo[b,e]thiepin-2-carboxylate (Compound 166a)

The product was prepared in a similar manner to Example 109 using Compound q obtained in Reference Example 17 and (3-methylpyridyl)methylthiol.

Physicochemical properties of the compounds obtained in Examples 109 to 122 are shown in Table 5-6.

TABLE 5-6

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 109 (8a) | colorless oil | — | (CDCl$_3$) 3.78(s,3H), 5.38 (s,1H), 4.91 & 6.26(ABq,J=12.5Hz,2H), 6.69-8.01(m,9H), 8.33(d,J=5.4Hz,2H) | (neat) 3030, 2950, 1711, 1570, 1434, 1245, 1118, 1007, 767 | — |
| 110 (8a′) | white solid | 129-131 (dec.) (diethylether)* | — | (KBr tablet) 1707, 1614, 1437, 1281, 1241, 1005 | C$_{21}$H$_{17}$NO$_3$S·C$_4$H$_4$O$_4$<br>　　C　　H　　N<br>Found 62.59　4.40　2.93<br>Calcd. 62.62　4.41　2.92 |
| 111 (14a) | yellow amorphous | — | (CDCl$_3$) 3.55(s,2H), 3.82 (s,3H), 4.86(s,1H), 4.84 & 6.36(ABq,J=13.4Hz,2H), 6.70-7.90(m,2H), 8.35-8.58(m,2H) | (CHCl$_3$) 2954, 1715, 1612, 1575, 1437, 1296, 1008 | — |
| 112 (15a) | colorless amorphous | 124-125 (methanol) | (CDCl$_3$) 3.56(bs,2H), 3.79 (s,3H), 4.79(s,1H), 4.84 & 6.18(ABq,J=12.7Hz,2H), 6.82-7.71(m,11H), 8.27-8.65(m,2H) | (CHCl$_3$) 2954, 1718, 1567, 1458, 1437, 1376, 1127, 1034 | C$_{22}$H$_{19}$NO$_3$S<br>　　C　　H　　N<br>Found 70.04　5.09　3.60<br>Calcd. 70.00　5.07　3.71 |
| 113 (19a) | colorless oil | — | (CDCl$_3$) 3.66(s,2H), 3.85(s,3H), 4.83(s,1H), 4.85 & 6.39 (ABq,J=12.8Hz,2H), 6.71-7.89(m,12H) | — | — |
| 114 (20a) | colorless oil | — | (CDCl$_3$) 3.50(s,2H), 3.63(s,2H), 3.67(s,3H), 4.78(s,1H), 4.85 & 6.25(ABq,J=13.0Hz,2H), 6.75-7.40(m,12H) | — | — |
| 115 (126a) | pale yellow oil | — | (CDCl$_3$) 3.51(s,2H), 3.63(s,3H), 4.99 & 5.89(ABq,J=13.7Hz,2H), 6.47(s,1H), 6.85-8.04(m,11H) | (neat) 2950, 1731, 1499, 1456, 1425, 1310, 1229, 757, 726 | — |
| 116 (129a) | colorless oil | — | (CDCl$_3$) 2.53-3.25(m,4H), 3.74(s,3H), 4.79(s,1H), 4.68 & 6.17(ABq,J=13.1Hz,2H), 6.64-7.90(m,11H) | — | — |
| 117 (130a) | colorless amorphous | — | (CDCl$_3$) 2.8-3.3(m,4H), 3.69 (s,3H), 3.86(s,3H), 4.85 & 6.37(ABq,J=12.9Hz,2H), 4.94 (s,1H), 6.82(d,J=8.5Hz,1H), 7.1-7.4(m,8H), 7.77(dd,J=2.2 & 8.5Hz,1H), 7.89(d,J=2.2Hz,1H) | (CHCl$_3$) 1714, 1611, 1249, 1120, 1008 | [MS(m/z): 444(M$^+$)] |
| 118 (132a) | yellow amorphous | — | (CDCl$_3$) 2.7-3.1(m,4H), 3.74 (s,6H), 3.84(s,2H), 4.84 & 6.36(ABq,J=13.1Hz,2H), 4.90 (s,1H), 5.23(s,2H), 6.6-7.4 (m,13H), 7.76(dd,J=2.1 & 8.5 Hz,1H), 7.90(d,J=2.1Hz,1H) | — | [MS(m/z): 550(M$^+$)] |
| 119 (153a) | pale yellow amorphous | — | (CDCl$_3$) 3.84(s,3H), 4.95 & 5.97(ABq,J=13.7Hz,2H), 6.20 (s,1H), 6.78-8.22(m,7H) | — | — |
| 120 (154a) | pale yellow crystal | (ethyl acetate) | (CDCl$_3$) 0.73-2.02(m,35H), 3.24(t,J=6.9Hz,2H), 3.82(s,3H), 4.98 & 6.04(ABq,J=12.5 Hz,2H), 6.13(s,1H), 6.84(d,J=8.5Hz,1H), 7.11-7.41(m,4H), 7.78(dd,J=2.0, 8.5Hz,1H), 8.03(d,J=2.0Hz,1H) | — | C$_{36}$H$_{50}$N$_2$O$_3$S$_3$<br>　　C　　H　　N<br>Found 66.21　7.66　4.27<br>Calcd. 66.02　7.69　4.28 |
| 121 (157a) | white solid | 189-191 (diisopropylether)* | (CDCl$_3$) 3.78(s,3H), 4.80 & 6.30(ABq,J=13.2Hz,2H), 5.25 (s,1H), 6.63-7.97(m,12H) | — | C$_{22}$H$_{18}$O$_5$S<br>　　C　　H<br>Found 66.85　4.61<br>Calcd. 66.99　4.60 |
| 122 | pale | | (CDCl$_3$) 3.62(s,2H), 3.89(s, | — | [MS(m/z): 393(M$^+$)] |

TABLE 5-6-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| (166a) | yellow oil | | 3H), 5.08(s,1H), 5.3-5.8(b, 2H), 7.0-7.35(m,6H), 7.5-7.7(m,2H), 7.82(bs,1H), 8.38(bs,1H), 8.45(d,J=8.0 Hz,1H) | | |

EXAMPLE 123
11-(4-Pyridyl)thio-6,11-dihydrodibenz[b,e]oxepin-2-carboxylic acid (Compound 8b)

EXAMPLE 124
11-[(3-Pyridyl)methyl]thio-6,11-dihydrodibenz[b,e]oxepin-2-carboxylic acid (Compound 14b)

EXAMPLE 125
11-[(3-Pyridyl)methyl]thio-6,11-dihydrodibenz[b,e]oxepin-3-carboxylic acid (Compound 15b)

EXAMPLE 126
Sodium 11-[(3-pyridyl)methyl]thio-6,11-dihydrodibenz[b,e]oxepin-3-carboxylate (Compound 15b′)

EXAMPLE 127
11-(Benzyl)thio-6,11-dihydrodibenz[b,e]oxepin-2-carboxylic acid (Compound 19b)

EXAMPLE 128
11-(Benzyl)thio-6,11-dihydrodibenz[b,e]oxepin-2-acetic acid (Compound 20b)

EXAMPLE 129
11-[2-(2-Benzimidazolyl)ethyl]thio-6,11-dihydrodibenz[b,e]oxepin-2-carboxylic acid 1.5 hydrate (Compound 129b′)

EXAMPLE 130
11-[2-(1-Methyl-2-benzimidazolyl)ethyl]thio-6,11-dihydrodibenz[b,e]oxepin-2-carboxylic acid (Compound 130b)

EXAMPLE 131
11-Phenylsulfonyl-6,11-dihydrodibenz[b,e]oxepin-2-carboxylic acid (Compound 157b)

EXAMPLE 132
11-[(3-Pyridyl)methyl]thio-6,11-dihydrodibenzo[b,e]-thiepin-2-carboxylic acid (Compound 166b)

In Examples 123 through 132, the objective compounds were prepared by hydrolyzing esters of the corresponding oxepine or thiepine derivatives in a manner similar to Example 14 or 15.

Compound 15b′ in Example 126 was treated in a manner similar to Example 62 to give the product as the sodium salt.

Physicochemical properties of the compounds obtained in Examples 123 to 132 are shown in Table 5-7.

TABLE 5

| Example No. (Compound No.) | Appearance | MP °C. (Solvent for recrystallization) | NMR (Solvent) δ, ppm | IR (Method) cm$^{-1}$ | Elemental analysis % | | |
|---|---|---|---|---|---|---|---|
| 123 (8 b) | white solid | 217-218 (dec.) (isopropanol) | (DMSO-d$_6$) 5.15 & 6.23 (ABq, J=12.9 Hz, 2H), 6.29 (s, 1H), 6.94 (d, J=8.5 Hz, 1H), 7.23-7.52 (m, 6H), 7.76 (dd, J=2.2, 8.5 Hz, 1H), 8.11 (d, J=2.2 Hz, 1H), 8.42 (d, J=4.4 Hz, 2H) | (KBr tablet) 1671, 1582, 1496, 1409, 1296, 1032, 1011 | C$_{20}$H$_{15}$NO$_3$S | | |
| | | | | | | C | H | N |
| | | | | | Found | 68.58 | 4.27 | 3.83 |
| | | | | | Calcd. | 68.75 | 4.33 | 4.01 |
| 124 (14 b) | white solid | 233-235 (diethylether)* | (DMSO-d$_6$) 3.67 & 3.78 (ABq, J=13.6 Hz, 2H), 4.95 & 6.13 (ABq, J=12.7 Hz, 2H), 5.23 (s, 1H), 6.68 (d, J=8.4 Hz, 1H), 7.28-7.41 (m, 6H), 7.65 (dd, J=1.9, 8.4 Hz, 1H), 7.80 (d, J=1.9 Hz, 1H), 8.41 (bs, 2H) | — | C$_{21}$H$_{17}$NO$_3$S | | |
| | | | | | | C | H | N |
| | | | | | Found | 69.56 | 4.65 | 3.56 |
| | | | | | Calcd. | 69.40 | 4.71 | 3.85 |
| 125 (15 b) | white solid | 107-110 (water)* | (DMSO-d$_6$) 3.75 & 3.83 (Abq, J=13.4 Hz, 2H), 5.02 & 6.09 (ABq, J=13.1 Hz, 2H), 5.30 (s, 1H), 7.29-7.68 (m, 9H), 8.43-8.44 (m, 2H), 13.01 (bs, 1H) | (KBr tablet) 2886, 1696, 1565, 1454, 1415, 1191, 1095, 1028 | C$_{21}$H$_{17}$NO$_3$S | | |
| | | | | | | C | H | N |
| | | | | | Found | 69.31 | 4.85 | 3.66 |
| | | | | | Calcd. | 69.40 | 4.71 | 3.85 |
| 126 (15 b′) | white solid | Impossible to measure due to hygroscopic nature | — | — | — | | |
| 127 (19 b) | white crystal | 211-212 (toluene) | (DMSO-d$_6$) 3.65 & 3.84 (ABq, J=12.9 Hz, 2H), 5.06 & 6.23 (ABq, J=12.8 Hz, 2H), 5.32 (s, 1H), 6.87 (d, J=8.5 Hz, 1H), 7.24-7.49 (m, 9H), 7.71 (dd, | (KBr tablet) 1682, 1608, 1454, 1428, 1407, 1298, 1254, 1108, | C$_{22}$H$_{18}$O$_3$S | | |
| | | | | | | C | H | |
| | | | | | Found | 72.92 | 4.83 | |
| | | | | | Calcd. | 72.90 | 5.01 | |

TABLE 5-continued

| Example No. (Compound No.) | Appearance | MP °C. (Solvent for recrystallization) | NMR (Solvent) δ, ppm | IR (Method) cm$^{-1}$ | Elemental analysis % | | |
|---|---|---|---|---|---|---|---|
| 128 (20 b) | white crystal | 125–127 (toluene) | (DMSO-d$_6$) 3.45 (s, 2H), 3.64 & 3.79 (ABq, J=13 Hz, 2H), 4.95 & 6.07 (ABq, J=12.9 Hz, 2H), 5.08 (s, 1H), 6.75 (d, J=8.1 Hz, 1H), 7.03–7.41 (m, 11H), J=2.2 & 8.5 Hz, 1H), 7.87 (d, J=2.2 Hz, 1H) | 1009, 715 (KBr tablet) 3450, 3022, 1694, 1499, 1313, 1203, 1123, 1019, 799, 759 | C$_{23}$H$_{20}$O$_3$S<br>C H<br>Found 73.11 5.56<br>Calcd. 73.38 5.35 | | |
| 129 (129 b′) | white crystal | 164–166 (isopropanol) | (DMSO-d$_6$) 2.87–3.36 (m, 4H), 5.04 & 6.22 (ABq, J=12.7 Hz, 2H), 5.43 (s, 1H), 6.86 (d, J = 8.5 Hz, 1H), 7.11–7.51 (m, 8H), 7.70 (dd, J=2.2 & 8.5 Hz, 1H), 8.00 (d, J=2.2 Hz, 1H) | (KBr tablet) 1611, 1577, 1379, 1367, 1252, 1226, 1007, 761 | C$_{24}$H$_{20}$N$_2$O$_3$S · 1.5 H$_2$O<br>C H N<br>Found 65.34 5.18 6.07<br>Calcd. 64.99 5.23 6.32 | | |
| 130 (130 b) | white crystal | 207–208 (isopropanol) | (DMSO d$_6$) 3.72 (s, 3H), 5.04 & 6.24 (ABq, J=12.7 Hz, 2H), 5.51 (s, 1H), 6.89 d, J=8.5 Hz, 1H), 7.11–7.23 (m, 2H), 7.35 –7.58 (m, 6H), 7.71 (dd, J=2.2 & 8.5 Hz, 1H), 8.02 (d, J=2.2 Hz, 1H) | (KBr tablet) 1695, 1615, 1231, 1007 | C$_{25}$H$_{22}$N$_2$O$_3$S<br>C H N<br>Found 69.78 5.11 6.38<br>Calcd. 69.75 5.15 6.51 | | |
| 131 (157 b) | white crystal | 233 (dec.) (isopropanol) | (CDCl$_3$ + DMSO-d$_6$) 4.92 & 6.35 (ABq, J=13.1 Hz, 2H), 5.85 (s, 1H), 6.90–8.07 (m, 12H) | — | C$_{21}$H$_{16}$O$_5$S<br>C H<br>Found 66.20 4.25<br>Calcd. 66.30 4.24 | | |
| 132 (166 b) | pale yellow crystal | 226–227.5 (methanol) | — | (KBr tablet) 1678, 1594, 1553, 1280, 1130, 1048 | C$_{21}$H$_{17}$NO$_2$S$_2$<br>C H N<br>Found 66.46 4.44 3.58<br>Calcd. 66.47 4.52 3.69 | | |

EXAMPLE 133

Methyl (E)-11-[2-[(2-pyridyl)thio]ethylidene]-6,11-dihydrodibenz[b,e]oxepin-2-carboxylate (Compound E-138a)

In 100 ml of N,N-dimethylformamide were stirred 2.0 g of methyl (E)-11-(2-chloroethylidene)-6,11-dihydrodibenz[b,e]oxepin-2-carboxylate (Compound h) obtained in Reference Example 8 and 1.1 g of 2-mercaptopyridine at 60° C. for 1.5 hours. The solvent was distilled off under reduced pressure. The obtained residue was extracted with 200 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate=5:1) to give 2.4 g of the product.

EXAMPLE 134

Methyl (E)-11-[2-[(2-pyrimidyl)thio]ethylidene]-6,11-dihydrodibenz[b,e]oxepin-2-carboxylate (Compound E-139a)

EXAMPLE 135

Methyl (E)-11-[2-[(2-quinolyl)thio]ethylidene]-6,11-dihydrodibenz[b,e]oxepin-2-carboxylate (Compound E-140a)

EXAMPLE 136

Methyl (E)-11-[2-[3-hydroxy-2-pyridyl)thio]ethylidene]-6,11-dihydrodibenz[b,e]oxepin-2-carboxylate (Compound E-141a)

EXAMPLE 137

Methyl (E)-11-[2-[(4-methyl-4H-1,2,4-triazol-3-yl)thio]ethylidene]-6,11-dihydrodibenz[b,e]oxepin-2-carboxylate (Compound E-156a)

In Examples 134 through 137, the objective compounds were prepared using Compound h and the corresponding thiol compounds in a manner similar to Example 133.

Physicochemical properties of the compounds obtained in Examples 133 to 137 are shown in Table 5-8.

TABLE 5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 133 (E-138 a) | colorless oil | — | (CDCl$_3$) 3.84 (s, 3H), 3.92 (d, J=7.9 Hz, 2H), 4.64–5.52 (b, 2H), 6.21 (t, J=7.9 Hz, 1H), 6.61–8.32 (m, 11H) | — | — |
| 134 (E-139 a) | colorless oil | — | (CDCl$_3$) 3.81 (s, 3H), 3.90 (d, J=7.7 Hz, 2H), 4.60–5.65 (b, 2H), 6.29 (t, J=7.7 Hz, 1H), | — | — |

TABLE 5-continued

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 135 (E-140 a) | — | — | 6.61–8.04 (m, 8H), 8.37 (d, J = 5.6 Hz, 2H) (CDCl$_3$) 3.79 (s, 3H), 4.10 (d, J=7.4 Hz, 2H), 4.56–5.58 (b, 2H), 6.31 (t, J=7.4 Hz, 1H), 6.66–8.06 (m, 13H) | — | — |
| 136 (E-141 a) | pale yellow crystal | 142–144 (toluene) | (CDCl$_3$) 3.86 (s, 3H), 4.6–5.6 (b, 2H), 6.25 (t, J=7.0 Hz, 1H), 6.83 (d, J=8.5 Hz, 1H), 7.0–8.1 (m, 9H) | (KBr tablet) 1682, 1445, 1305, 1247, 1129, 999 | C$_{23}$H$_{19}$NO$_4$S<br>　　　C　　H　　N<br>Found　68.01　4.88　3.51<br>Calcd.　68.13　4.72　3.45 |
| 137 (E-156 a) | colorless oil | — | (CDCl$_3$) 3.41 (s, 3H), 3.78 (s, 3H), 4.62–5.53 (m, 4H), 6.21 (t, J=7.9 Hz, 1H), 6.60–7.94 (m, 7H), 8.05 (s, 1H) | — | — |

EXAMPLE 138

(E)-11-[2-[(2-Pyridyl)thio]ethylidene]-6,11-dihydrodibenz[b,e]oxepin-2-carboxylic acid (Compound E-138b)

EXAMPLE 139

(E)-11-[2-[(2-Pyrimidyl)thio]ethylidene]-6,11-dihydrodibenz[b,e]oxepin-2-carboxylic acid (Compound E-139b)

EXAMPLE 140

(E)-11-[2-[(2-Quinolyl)thio]ethylidene]-6,11-dihydrodibenz[b,e]oxepin-2-carboxylic acid (Compound E-140b)

EXAMPLE 141

(E)-11-[2-[(3-Hydroxy-2-pyridyl)thio]ethylidene]-6,11-dihydrodibenz[b,e]oxepin-2-carboxylic acid (Compound E-141b)

EXAMPLE 142

(E)-11-[2-[(4-Methyl-4H-1,2,4-triazol-3-yl)thio]ethylidene]-6,11-dihydrodibenz[b,e]oxepin-2-carboxylic acid (Compound E-156b)

In Examples 138 through 142, the products were prepared by hydrolyzing esters of the corresponding oxepine derivatives in a manner similar to Example 14 or 15.

Physicochemical properties of the compounds obtained in Examples 138 to 142 are shown in Table 5-9.

TABLE 5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 138 (E-138 b) | white crystal | 242–243 (isopropanol) | (DMSO-d$_6$) 3.84–3.93 (m, 2H) 5.01 & 5.36 (each bs, 2H), 6.21 (t, J = 7.8 Hz, 1H), 6.81 (d, J = 8.5 Hz, 1H), 7.08–7.65 (m, 7H), 7.71 (dd, J = 2.2, 8.5 Hz, 1H), 7.84 d, J = 2.2 Hz, 1H), 8.29–8.31 (m, 1H), 12.73 (bs, 1H) | (KBr tablet) 1684, 1602, 1454, 1435, 1418, 1315, 1262, 995, 756 | C$_{22}$H$_{17}$NO$_3$S<br>　　　C　　H　　N<br>Found　70.30　4.55　3.35<br>Calcd.　70.38　4.56　3.73 |
| 139 (E-139 b) | yellow crystal | 250–253 (isopropanol) | (DMSO-d$_6$) 3.80–3.87 (m, 2H), 5.04 & 5.45 (each bs, 2H), 6.24 (t, J = 7.7 Hz, 1H), 6.82 (d, J = 8.6 Hz, 1H), 7.19–7.60 (m, 5H), 7.71 (dd, J = 2.1, 8.6 Hz, 1H), 7.86 (d, J = 2.2 Hz, 1H), 8.56 (d, J = 4.9 Hz, 2H) | (KBr tablet) 1690, 1605, 1568, 1553, 1408, 1382, 1248, 1194, 1003, 754, | C$_{21}$H$_{16}$N$_2$O$_3$S<br>　　　C　　H　　N<br>Found　66.98　4.42　7.52<br>Calcd.　67.01　4.28　7.44 |
| 140 (E-140 b) | yellow crystal | 225–228 (dec.) (isopropanol) | — | (KBr tablet) 3450, 1693, 1602, 1591, 1496, 1311, 1259, 1135, 1088, 1001, 810 | C$_{26}$H$_{19}$NO$_3$S<br>　　　C　　H　　N<br>Found　73.38　4.52　3.37<br>Calcd.　73.39　4.50　3.29 |
| 141 (E-141 b) | pale yellow crystal | 201.5–203 (acetonitrile) | (DMSO-d$_6$) 3.65 (m, 2H), 5.02 & 5.43 (each bs, 2H), 6.20 (t, J = 7.8 Hz, 1H), 6.81 (d, J = 8.5 Hz, 1H), 6.95–7.10 (m, 2H), 7.35–7.60 (m, 4H), 7.71 (dd, J = 2.2 & 8.5 Hz, 1H), 7.80–7.85 (m, 2H), 10.40 (s, 1H) | (KBr tablet) 1678, 1605, 1441, 1294, 1264, 1241, 1003 | C$_{22}$H$_{17}$NO$_4$S<br>　　　C　　H　　N<br>Found　67.88　4.23　3.81<br>Calcd.　67.50　4.38　3.58 |
| 142 (E-156 b) | white crystal | 236–237 (isopro- | (DMSO-d$_6$) 3.35 (s, 3H), 3.80 –3.84 (m, 2H), 4.88 & 5.14 | (KBr tablet) 1670, 1607, | C$_{20}$H$_{17}$N$_3$O$_3$S<br>　　　C　　H　　N |

TABLE 5-continued

| Example No. (Compound No.) | Appearance | MP °C. (Solvent for recrystallization) | NMR (Solvent) δ, ppm | IR (Method) cm$^{-1}$ | Elemental analysis % | | |
|---|---|---|---|---|---|---|---|
| | | panol) | (each bs, 2H), 6.20 (t, J = 7.9 Hz, 1H), 6.81 (d, J = 8.5 Hz, 1H), 7.2–7.5 (m, 4H), 7.72 (dd, J = 2.2, 8.5 Hz, 1H), 7.84 (d, J = 2.2 Hz, 1H), 8.51 (s, 1H) | 1484, 1426, 1318, 1242, 1198, 1014 770, 755 | Found 63.28 Calcd. 63.31 | 4.55 4.52 | 11.22 11.07 |

EXAMPLE 143

Methyl 11-[2-(1-benzimidazolyl)ethyl]thio-6,11-dihydrodibenz[b,e]oxepin-2-carboxylate (Compound 45a)

The objective compound was prepared in a manner similar to Example 23, using 1.6 g of methyl 11-(2-iodoethyl)thio-6,11-dihydrodibenz[b,e]oxepin-2-carboxylate (Compound n) obtained in Reference Example 14 and 1.4 g of benzimidazole.

EXAMPLE 144

Methyl 11-[2-[(1,2,3,4-tetrahydroisoquinolin)-2-yl]ethyl]thio-6,11-dihydrodibenz[b,e]oxepin-2-carboxylate (Compound 158a)

In a solvent mixture of 200 ml of ethanol and 50 ml of dioxane were heated to reflux 6.0 g of Compound n and 10 ml of 1,2,3,4-tetrahydroisoquinoline for 4.5 hours. After allowing to cool, the solvent was distilled off under reduced pressure. The obtained residue was extracted with 500 ml of methylene chloride and washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=50:10:5) to give 5.2 g of the product.

EXAMPLE 145

Methyl 11-[2-[(6,7-dimethoxy-1,2,3,4-tetrahydroisoquinolin)-2-yl]ethyl]thio-6,11-dihydrodibenz[b,e]oxepin-2-carboxylate (Compound 161a)

The objective compound was prepared in a manner similar to Example 144, using Compound n and the corresponding isoquinoline derivative.

EXAMPLE 146

Methyl (Z,E)-11-[3-[(1,2,3,4-tetrahydroisoquinolin)-2-yl]propylidene]-6,11-dihydrodibenz[b,e]oxepin-2-carboxylate (Compound 162a)

The objective compound was prepared in a manner similar to Example 144, using Compound m and the corresponding isoquinoline derivative.

Physicochemical properties of the compounds obtained in Examples 143 to 146 are shown in Table 5-10.

TABLE 5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 143 (45 a) | pale yellow amorphous | — | (CDCl$_3$) 2.79 (t, J=6.9 Hz, 2H), 3.82 (s, 3H), 4.01 (t, J=6.9 Hz, 2H), 4.76 (s, 1H), 4.76 & 6.25 (ABq, J=12.8 Hz, 2H), 6.64 –7.91 (m, 11H) | — | — |
| 144 (158 a) | yellow oil | — | (CDCl$_3$) 2.20–3.03 (m, 8H), 3.57 (s, 2H), 3.83 (s, 3H), 5.10 (s, 1H), 4.86 & 6.47 (ABq, J=12.7 Hz, 2H), 6.75–8.06 (m, 11H) | (neat) 3400, 2948, 2800, 1718, 1611, 1497, 1435, 1244, 1118, 1008, 769, 741 | — |
| 145 (161 a) | colorless oil | — | (CDCl$_3$) 2.68–3.77 (m, 8H), 3.78 (s, 6H), 3.81 (s, 3H), 4.38 (bs, 2H), 4.98 & 6.28 (ABq, J=11.5 Hz, 2H), 5.56 (s, 1H), 6.58–8.14 (m, 9H) | — | — |
| 146 (162 a) | colorless oil | — | (CDCl$_3$) 2.41–2.92 (m, 8H), 3.57 (bs, 2H), 3.79 (s, 2H), 5.14 (bs, 2H), 5.73 (bs, 1H), 7.59–7.99 (m, 11H) | (neat) 2948, 2922, 1711, 1607, 1488, 1435, 1239, 1130, 1118, 1004, 767 | — |

EXAMPLE 147

11-[2-(1-Benzimidazolyl)ethyl]thio-6,11-dihydrodibenz[b,e]oxepin-2-carboxylate .monohydrochloride (Compound 45b')

Compound 45a, 0.85 g, obtained in Example 143 was hydrolyzed in a manner similar to Example 15. By adjusting pH to 1.8, the hydrochloride of the product was precipitated and collected.

EXAMPLE 148

11-[2-[(1,2,3,4-Tetrahydroisoquinolin)-2-yl]ethyl]thio-6,11-dihydrodibenz[b,e]oxepin-2-carboxylate .1.8 hydrate (Compound 158b')

EXAMPLE 149

11-[2-[(6,7-Dimethoxy-1,2,3,4-tetrahydroisoquinolin)-2-yl]ethyl]thio-6,11-dihydrodibenz[b,e]oxepin-2-carboxylate .1.5 hydrate (Compound 161b')

In Examples 148 and 149, the objective compound was prepared by hydrolyzing esters of the corresponding oxepine derivative in a manner similar to Example 14 or 15.

EXAMPLE 150

(Z,E)-11-[3-[(1,2,3,4-Tetrahydroisoquinolin)-2-yl]propylidene]-6,11-dihydrodibenz[b,e]oxepin-2-carboxylate .monohydrochloride (Compound 162b')

Compound 162a (Z/E=7/3), 2.1 g obtained in Example 146 was hydrolyzed in a manner similar to Example 15. By adjusting pH to 1.0, the objective compound was precipitated as the hydrochloride and collected by filtration. The crude product was recrystallized from isopropanol twice to give 0.9 g of the objective compound (Z/E=9/1).

Physicochemical properties of the compounds obtained in Examples 147 to 150 are shown in Table 5-11.

TABLE 5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 147 (45 b') | white crystal | 230–231.5 (dec.) (acetonitrile) | (DMSO-d$_6$) 2.99 (t, J=6.7 Hz, 2H), 4.61–4.74 (m, 2H), 4.99 & 6.14 (ABq, J = 12.8 Hz, 2H), 5.65 (s, 1H), 6.87 (d, J=8.6 Hz, 1H), 7.34–7.94 (m, 9H), 8.05 (d, J=2.0 Hz, 1H), 9.34 (s, | (KBr tablet) 1698, 1608, 1499, 1446, 1236, 1202, 1114, 1005, 759 | C$_{24}$H$_{20}$N$_2$O$_3$S · HCl<br>　　C　　H　　N<br>Found　63.59　4.64　6.29<br>Calcd.　63.64　4.67　6.18 |
| 148 (158 b') | yellow powder | 139–141 (isopropyl ether) | (DMSO-d$_6$) 2.50–3.78 (m, 10H), 5.06 & 6.25 (ABq, J=12.7 Hz, 2H), 5.50 (s, 1H), 6.87–8.02 (m, 11H) | (KBr tablet) 3450, 2930, 1700, 1608, 1232, 1107, 1007, 750 | C$_{26}$H$_{25}$NO$_3$S · 1.8 H$_2$O<br>　　C　　H　　N<br>Found　67.06　6.00　3.04<br>Calcd.　67.31　6.21　3.02 |
| 149 (161 b') | white crystal | 112–113 (isopropanol) | (DMSO-d$_6$) 2.50–2.65 (m, 6H), 3.43–3.69 (m, 2H), 3.69 (s, 3H), 3.70 (s, 3H), 3.80–3.95 (m, 2H), 5.05 & 6.28 (ABq, J = 12.7 Hz, 2H), 5.48 (s, 1H), 6.58 (s, 1H), 6.64 (s, 1H), 6.87 (d, J=8.5 Hz, 1H), 7.37–7.48 (m, 4H), 7.71 (dd, J=2.2 & 8.5 Hz, 1H), 7.99 (d, J=2.2 Hz, 1H) | (KBr tablet) 2930, 1610, 1519, 1456, 1371, 1229, 1122, 1009, 787 | C$_{28}$H$_{29}$NO$_5$S · 1.5 H$_2$O<br>　　C　　H　　N<br>Found　64.96　6.22　2.45<br>Calcd.　64.85　6.22　2.70 |
| 150 (162 b') | white crystal | 253–254 (dec.) (isopropanol) | — | — | C$_{27}$H$_{25}$NO$_3$S · HCl<br>　　C　　H　　N<br>Found　72.30　5.96　3.01<br>Calcd.　72.39　5.85　3.13 |

EXAMPLE 151

Methyl 11-[(3-pyridyl)methyl]oxy-6,11-dihydrodibenz[b,e]oxepin-2-carboxylate (Compound 21a)

EXAMPLE 152

Methyl 11-[(3-pyridyl)ethyl]oxy-6,11-dihydrodibenz[b,e]oxepin-2-carboxylate (Compound 22a)

EXAMPLE 153

Methyl 11-[2-[(2-hydroxy)phenyl]ethyl]oxy-6,11-dihydrodibenz[b,e]oxepin-2-carboxylate (Compound 165a)

In Examples 151 through 153, the objective compounds were prepared in a manner similar to Example 1, using methyl 11-hydroxy-6,11-dihydrodibenz[b,e]oxepin-2-carboxylate (Compound b) obtained in Reference Example 2 and the corresponding alcohol compounds.

Physicochemical properties of the compounds obtained in Examples 151 to 153 are shown in Table 5-12.

TABLE 5

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 151 (21 a) | white solid | unclear (isopropanol) | (CDCl$_3$) 3.83 (s, 3H), 4.48 (s, 2H), 5.20 (s, 1H), 4.87 & 6.14 (ABq, J=12 Hz, 2H), 6.73–8.01 (m, 9H), 8.31–8.60 (m, 2H) | (KBr tablet) 1717, 1609, 1252, 1124, 1030, 1012, 769 | C$_{22}$H$_{19}$NO$_4$<br>　　C　　H　　N<br>Found　73.15　5.30　3.70<br>Calcd.　73.12　5.30　3.88 |
| 152 (22 a) | colorless oil | — | (CDCl$_3$) 3.02 (t, J=6.5 Hz, 2H), 3.84 (t, J=6.5 Hz, 2H), 3.81 (s, 3H), 5.11 (s, 1H), 4.70 & 5.86 (ABq, J=12.2 Hz, 2H), 6.69– | (neat) 1716, 1613, 1436, 1290, 1245, 1006, | — |

TABLE 5-continued

| Example No. (Compound No.) | Appearance | MP °C. (Solvent for recrystallization) | NMR (Solvent) δ, ppm | IR (Method) cm⁻¹ | Elemental analysis % |
|---|---|---|---|---|---|
| 153 (165 a) | yellow oil | — | (CDCl₃) 2.86 (t, J=5.4 Hz, 2H), 3.42–3.90 (m, 2H), 3.82 (s, 3H), 4.78 & 5.92 (ABq, J=12.0 Hz, 2H), 5.15 (s, 1H), 6.58–7.98 (m, 11H) 8.02 (m, 10H), 8.31–8.50 (m, 1H) | 769 (CHCl₃) 3270, 1715, 1615, 1490, 1295, 1253, 1122, 1006 | — |

EXAMPLE 154

11-[(3-Pyridyl)methyl]oxy-6,11-dihydrodibenz[b,e]oxepin-2-carboxylic acid .dihydrate (Compound 21b′)

EXAMPLE 155

Sodium 11-[(3-pyridyl)ethyl]oxy-6,11-dihydrodibenz[b,e]oxepin-2-carboxylic acid .monohydrate (Compound 22b′)

EXAMPLE 156

11-[2-[(2-Hydroxy)phenyl]ethyl]oxy-6,11-dihydrodibenz[b,e]oxepin-2-carboxylic acid .0.2 isopropyl ether (Compound 165b′)

In examples 154 through 156, the objective compounds were prepared by hydrolyzing esters of the corresponding oxepine derivatives in a manner similar to Example 14 or 15.

Compound 22b′ in Example 155 was treated in a manner similar to Example 62 to give the product as the sodium salt.

Physicochemical properties of the compounds obtained in Examples 154 to 156 are shown in Table 5-13.

and 15.8 ml of dicyclohexylmethylamine was dropwise added 50 ml of a dry benzene solution containing 4.1 ml of titanium tetrachloride. After heating to reflux for 3.5 hours, saturated sodium bicarbonate aqueous solution was added to the reaction mixture followed by stirring. Insoluble matters were filtered off and the filtrate was extracted with 300 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=10:5:1) to give 1.7 g of the crude product. The obtained crude product was recrystallized from isopropyl ether to give 1.3 g of the product.

EXAMPLE 158

Methyl 11-(3-pyridyl)imino-6,11-dihydrodibenz[b,e]oxepin-2-carboxylate (Compound 23a)

EXAMPLE 159

Methyl 11-(3-pyridyl)imino-6,11-dihydrodibenz[b,e]oxepin-2-acetate (Compound 24a)

TABLE 5

| Example No. (Compound No.) | Appearance | MP °C. (Solvent for recrystallization) | NMR (Solvent) δ, ppm | IR (Method) cm⁻¹ | Elemental analysis % |
|---|---|---|---|---|---|
| 154 (21 b′) | white crystal | (isopropanol) | (DMSO-d₆) 4.45 & 4.56 (ABq, J=11.8 Hz, 2H), 4.98 & 5.98 (ABq, J=12.1 Hz, 2H), 5.46 (s, 1H), 6.72 (d, J=8.4 Hz, 1H), 7.31–7.69 (m, 6H), 7.75 (dd, J=1.9, 8.3 Hz, 1H), 7.95 (d, J=1.9 Hz, 1H), 8.47 (bs, 2H) | (KBr tablet) 1615, 1584, 1541, 1394, 1256, 1232, 1136, 1049, 1008 | C₂₁H₁₇NO₄ · 2H₂O<br>    C    H    N<br>Found 65.58 5.20 3.52<br>Calcd. 65.79 5.52 3.65 |
| 155 (11 b′) | white solid | unclear (isopropyl ether)* | — | (KBr tablet) 1614, 1590, 1549, 1393, 1254, 1230, 1111, 1072, 1008 | C₂₂H₁₈NO₄Na · H₂O<br>    C    H    N<br>Found 65.45 4.80 3.54<br>Calcd. 65.83 5.02 3.49 |
| 156 (165 b′) | yellow powder | 110–120 (unclear) (isopropyl ether - hexane) | (CDCl₃) 2.90–2.94 (m, 2H), 3.62–3.81 (m, 2H), 4.86 & 5.98 (ABq, J=12.4 Hz, 2H), 5.22 (s, 1H), 6.79–7.42 (m, 9H), 7.96 (dd, J=2.2, 8.7 Hz, 1H), 8.07 (d, J=2.2 Hz, 1H) | — | C₂₃H₂₀O₅ · 0.2 C₆H₁₄O<br>    C    H<br>Found 73.55 5.84<br>Calcd. 73.24 5.79 |

EXAMPLE 157

Methyl 11-[(3-pyridyl)methyl]imino-6,11-dihydrodibenz[b,e]oxepin-2-carboxylate (Compound 25a)

To 150 ml of a dry benzene solution containing a mixture of 5.0 g of methyl 11-oxo-6,11-dihydrodibenz[b,e]oxepin-2-carboxylate (Compound a) obtained in Reference Example 1, 13 ml of 3-aminomethylpyridine

EXAMPLE 160

Methyl 11-[2-(2-pyridyl)ethyl]imino-6,11-dihydrodibenz[b,e]oxepin-2-carboxylate (Compound 28a)

EXAMPLE 161

Methyl 11-[2-(1-methylpyrrol-2-yl)ethyl]imino-6,11-dihydrodibenz[b,e]oxepin-2-carboxylate (Compound 29a)

In Examples 158 through 161, the objective compounds were prepared in a manner similar to Example 157, using the corresponding 11-oxo-6,11-dihydrodibenz[b,e]oxepine derivative (Compounds a and e) and amino compounds.

Physicochemical properties of the compounds obtained in Examples 157 to 161 are shown in Table 5-14.

EXAMPLE 165

11-[2-(2-Pyridyl)ethyl]imino-6,11-dihydrodibenz[b,e]oxepin-2-carboxylic acid (Compound 28b)

EXAMPLE 166

11-[2-(2-Pyridyl)ethyl]imino-6,11-dihydrodibenz[b,e]oxepin-2-carboxylic acid .0.5 fumarate (Compound 28b')

EXAMPLE 167

11-[2-(1-Methylpyrrol-2-yl)ethyl]imino-6,11-dihydrodibenz[b,e]oxepin-2-carboxylic acid (Compound 29b)

In Examples 162 through 167, the objective compounds were prepared by hydrolyzing esters of the corresponding oxepine derivatives in a manner similar to Example 14 or 15.

Compound 28b' in Example 166 was treated in a manner similar to Example 10 to give the product as the fumarate.

Physicochemical properties of the compounds obtained in Examples 162 to 167 are shown in Table 5-15.

TABLE 5-14

| Example No. (Compound No.) | Appearance | MP °C. (Solvent for recrystallization) | NMR (Solvent) δ, ppm | IR (Method) cm$^{-1}$ | Elemental analysis % | | | |
|---|---|---|---|---|---|---|---|---|
| 157 (25a) | white crystal | 111–112 (isopropyl ether) | (CDCl$_3$) 3.85(s,3H), 4.79 (bs,2H), 5.14(bs,2H), 6.73–8.05(m,9H), 8.33–8.66(m,2H) | (KBr tablet) 1715, 1610, 1490, 1435, 1250, 1120, 1005, 765 | | C$_{22}$H$_{18}$N$_2$O$_3$ | | |
| | | | | | | C | H | N |
| | | | | | Found | 73.70 | 5.00 | 7.70 |
| | | | | | Calcd. | 73.73 | 5.06 | 7.82 |
| 158 (23a) | colorless crystal | 129.5–131 (isopropyl ether) | (CDCl$_3$) 3.89(s,3H), 5.27 (s,2H), 6.62–8.22(m,10H), 8.62–8.76(m,1H) | (CHCl$_3$) 2925, 1718, 1608, 1580, 1410, 1250, 1120, 1002 | | C$_{21}$H$_{16}$N$_2$O$_3$ | | |
| | | | | | | C | H | N |
| | | | | | Found | 73.20 | 4.88 | 8.30 |
| | | | | | Calcd. | 73.24 | 4.68 | 8.13 |
| 159 (24a) | yellow crystal | 153–155 (isopropyl ether) | (CDCl$_3$) 3.65(s,2H), 3.71 (s,3H), 5.27(bs,2H), 6.6–8.3(m,11H) | (KBr tablet) 1737, 1605, 1473, 1414, 1303, 1230, 1003, 810, 714 | | C$_{22}$H$_{18}$N$_2$O$_3$ | | |
| | | | | | | C | H | N |
| | | | | | Found | 73.56 | 5.41 | 7.59 |
| | | | | | Calcd. | 73.73 | 5.06 | 7.82 |
| 160 (28a) | yellow crystal | 120–122 (isopropyl ether)* | (CDCl$_3$) 3.25(t,J = 6.9 Hz,2H), 3.82(s,3H), 4.00(t,J = 6.9 Hz, 2H), 4.88(bs,2H), 6.67–7.90 (m,10H), 8.24–8.47(m,2H) | (KBr tablet) 1708, 1626, 1607, 1590, 1479, 1435, 1258, 1238, 1130, 1006, 766 | | C$_{23}$H$_{20}$N$_2$O$_3$ | | |
| | | | | | | C | H | N |
| | | | | | Found | 74.20 | 5.42 | 7.53 |
| | | | | | Calcd. | 74.18 | 5.41 | 7.52 |
| 161 (29a) | yellow solid | 114–115 (isopropyl ether)* | (CDCl$_3$) 2.99(t,J = 7.1 Hz,2H) 3.30(s,3H), 3.83(t,J = 7.1 Hz, 2H), 3.80(s,3H), 4.88(bs, 2H), 5.72(bs,1H), 5.90(t, J = 3.2 Hz,1H), 6.36(bs,1H), 6.63–7.91(m,6H), 8.29(d, J = 2.4 Hz,1H) | (KBr tablet) 1712, 1626, 1607, 1487, 1438, 1289, 1265, 1241, 1129, 1001, 766, 725 | | C$_{23}$H$_{22}$N$_2$O$_3$ | | |
| | | | | | | C | H | N |
| | | | | | Found | 73.48 | 5.99 | 7.30 |
| | | | | | Calcd. | 73.78 | 5.92 | 7.48 |

EXAMPLE 162

11-[(3-Pyridyl)methyl]imino-6,11-dihydrodibenz[b,e]oxepin-2-carboxylic acid (Compound 25b)

EXAMPLE 163

11-(3-Pyridyl)imino-6,11-dihydrodibenz[b,e]oxepin-2-carboxylic acid (Compound 23b)

EXAMPLE 164

11-(3-Pyridyl)imino-6,11-dihydrodibenz[b,e]oxepin-2-acetic acid .monohydrate (Compound 24b')

TABLE 5-15

| Example No. (Compound No.) | Appearance | MP °C. (Solvent for recrystallization) | NMR (Solvent) δ, ppm | IR (Method) cm$^{-1}$ | Elemental analysis % | | | |
|---|---|---|---|---|---|---|---|---|
| 162 (25b) | white solid | 244–245.5 (isopropanol) | (DMSO-d$_6$) 4.5–5.5(m,4H), 6.96(d,J = 8.6 Hz,1H), 7.37–7.80(m,6H), 7.87(dd,J = 2.2 & 8.6 Hz,1H), 8.34(d,J = 2.2 Hz,1H), 8.49(d,J = 3.9 Hz,1H), 8.57(bs,1H) | (KBr tablet) 2374, 1701, 1630, 1606, 1486, 1428, 1312, 1236, 1047, 1005, 791, 772, | | C$_{21}$H$_{16}$N$_2$O$_3$ | | |
| | | | | | | C | H | N |
| | | | | | Found | 72.96 | 4.52 | 8.10 |
| | | | | | Calcd. | 73.24 | 4.68 | 8.13 |

TABLE 5-15-continued

| Example No. (Compound No.) | Appearance | MP °C. (Solvent for recrystallization) | NMR (Solvent) δ, ppm | IR (Method) cm$^{-1}$ | Elemental analysis % |
| --- | --- | --- | --- | --- | --- |
| 163 (23b) | white solid | 307–308 (isopropanol) | (DMSO-d$_6$) 5.48(bs,2H), 6.80(d,J = 7.8 Hz,1H), 7.04(d, J = 8.5 Hz,1H), 7.13–7.60(m, 5H), 7.94(dd,J = 2.2 & 8.5 Hz, 1H), 8.04(d,J = 2.2 Hz,1H), 8.18(d,J = 3.2 Hz,1H), 8.63(d, J = 2.2 Hz,1H) | 647 (KBr tablet) 2368, 1680, 1662, 1604, 1489, 1411, 1331, 1269, 1185, 1096, 1044, 1005, 775, 767 | C$_{20}$H$_{14}$N$_2$O$_3$<br>    C    H    N<br>Found 72.52 4.13 8.50<br>Calcd. 72.72 4.27 8.48 |
| 164 (24b') | white crystal | 230–232 (isopropanol) | (DMSO-d$_6$) 3.60(s,2H), 5.36 (s,2H), 6.75(d,J = 7.6 Hz,1H), 6.89(d,J = 8.5 Hz,1H), 7.09–7.38(m,5H), 7.56(d,J = 7.1 Hz, 1H), 7.89(d,J = 2.2 Hz,1H), 8.00(bs,1H), 8.15–8.17(m,1H) | (KBr tablet) 1715, 1605, 1490, 1420, 1300, 1218, 1015, 815 | C$_{21}$H$_{16}$N$_3$O$_3$·H$_2$O<br>    C    H    N<br>Found 71.70 4.64 7.80<br>Calcd. 71.38 4.85 7.92 |
| 165 (28b) | white amorphous | Impossible to measure due to hygroscopic nature | — | — | — |
| 166 (28b') | white crystal | unclear (isopropanol) | (DMSO-d$_6$) 3.16(bs,2H), 5.00 (s,2H), 6.58(s,1H), 6.87 (d,J = 8.5 Hz,1H), 7.15–7.68 (m,7H), 7.81(dd,J = 2.2 & 8.5 Hz,1H), 8.21(d,J = 2.2 Hz,1H), 8.37–8.39(m,1H) | (KBr tablet) 1699, 1622, 1606, 1486, 1285, 1236, 1015, 768, 655 | C$_{22}$H$_{18}$N$_2$O$_3$·0.5C$_4$H$_4$O$_4$<br>    C    H    N<br>Found 63.51 4.45 6.70<br>Calcd. 63.45 4.84 6.72 |
| 167 (29b) | white crystal | unclear (isopropanol) | (DMSO-d$_6$) 2.96–3.08(m,3H), 3.34(s,3H), 3.34–3.59(m, 2H), 3.6–3.9(m,2H), 5.03 (bs,2H), 5.58–5.60(m,1H), 5.80–5.83(m,1H), 6.52–6.54 (m,1H), 6.89(d,J = 8.5 Hz,1H), 7.40–7.60(m,4H), 7.82(dd,J = 2.2 & 8.5 Hz,1H), 8.26(d,J = 2.2 Hz,1H), 12.79(bs,1H) | (KBr tablet) 2904, 1696, 1606, 1568, 1487, 1407, 1315, 1248, 1201, 1120, 995, 775, 764, 711 | C$_{23}$H$_{22}$N$_2$O$_3$<br>    C    H    N<br>Found 73.23 5.60 7.70<br>Calcd. 73.32 5.59 7.77 |

EXAMPLE 168

Methyl 11-(3-pyridine)carboxamine-6,11-dihydrodibenz[b,e]oxepin-2-carboxylate (Compound 30a)

Methyl 11-amino-6,11-dihydrodibenz[b,e]oxepin-2-carboxylate (Compound o), 4.0 g, obtained in Reference EXAMPLE 15 was suspended in 200 ml of methylene chloride and, 7.0 g of nicotinic chloride and then 50 ml of triethylamine were added to the suspension. The mixture was stirred at room temperature for a day. Water was further added to the reaction mixture. After stirring for 2 hours, the reaction mixture was extracted with 200 ml of methylene chloride. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; ethyl acetate:triethylamine=10:1) to give 2.0 g of the product.

EXAMPLE 169

Methyl 11-(1-imidazolyl)acetamido-6,11-dihydrodibenz[b,e]oxepin-2-carboxylate (Compound 33a)

Compound o, 10.0 g, was suspended in a solvent mixture of 200 ml of methylene chloride and 5.2 ml of triethylamine and, 20 ml of a methylene chloride solution containing 3 ml of chloroacetic chloride was dropwise added to the suspension. The mixture was stirred at room temperature for further 2 hours. The solvent was distilled off under reduced pressure to give methyl 11-chloroacetamide-6,11-dihydrodibenz[b,e]oxepin-2-carboxylate. This ester was used in the following reaction without further purification.

Crude methyl 11-chloroacetamido-6,11-dihydrodibenz[b,e]oxepin-2-carboxylate, 3.0 g, was heated to reflux for 4 hours in 100 ml of toluene together with 0.9 g of imidazole. After allowing to cool, the solvent was distilled off under reduced pressure. The obtained residue was extracted with 300 ml of methylene chloride. The extract was washed successively with saturated sodium bicarbonate aqueous solution and saturated sodium chloride aqueous solution. After drying over anhydrous sodium sulfate, the solvent was distilled off under reduced pressure. The resulting residue was subjected to silica gel column chromatography (eluting solvent; chloroform:methanol=10:1) to give 1.6 g of the product.

EXAMPLE 170

Sodium 11-(3-pyridine)carboxamido-6,11-dihydrodibenz[b,e]oxepin-2-carboxylate .trihydrate (Compound 30b')

EXAMPLE 171

11-(1-Imidazolyl)acetamido-6,11-dihydrodibenz[b,e]oxepin-2-carboxylic acid (Compound 33b)

In Examples 170 and 171, the objective compounds were prepared by hydrolyzing esters of the corresponding oxepine derivatives in a manner similar to Example 14 or 15.

Compound 30b' in Example 170 was treated in a manner similar to Example 62 to give the product as the sodium salt.

Physicochemical properties of the compounds obtained in Examples 168 to 171 are shown in Table 5-16.

with 1N hydrochloric acid aqueous solution, saturated sodium bicarbonate aqueous solution and saturated sodium chloride aqueous solution. After drying over anhydrous sodium sulfate, the solvent was distilled off under reduced pressure. The resulting residue was subjected to silica gel column chromatography (eluting

TABLE 5-16

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 168 (30a) | pinkish crystal | 225–227 (isopropyl ether)* | (CDCl$_3$ + DMSO-d$_6$) 3.86(s,3H), 5.12 & 5.91(ABq,J = 12.7 Hz, 2H), 6.39(d,J = 6.0 Hz,1H), 6.91(d,J = 8.2 Hz,1H), 7.14–8.31(m,8H), 8.55–8.69(m,1H), 9.03–9.13(m,1H), 9.34 (d,J = 6.0 Hz, 1H) | — | C$_{22}$H$_{18}$N$_2$O$_4$<br>  C    H    N<br>Found 70.15 4.75 7.36<br>Calcd. 70.58 4.85 7.48 |
| 169 (33a) | white solid | 223–224 (isopropyl ether) | (CDCl$_3$ + DMSO-d$_6$) 3.80(s,3H), 4.66(s,2H), 5.11 & 5.69(Abq, J = 13.8 Hz,2H), 6.10(d,J = 6.6 Hz,1H), 6.74–8.01(m,10H), 9.26(d,J = 6.6 Hz,1H) | (KBr tablet) 3270, 1718, 1669, 1611, 1556, 1435, 1297, 1265, 1246, 1128, 998, 766 | C$_{21}$H$_{19}$N$_3$O$_4$<br>  C    H    N<br>Found 66.61 5.27 10.98<br>Calcd. 66.83 5.07 11.13 |
| 170 (30b') | white solid | 240 (dec.) (water) | (DMSO-d$_6$ + CD$_3$OD) 5.18 & 5.76(Abq,J = 13.3 Hz,2H), 6.42(s,1H), 6.75(d,J = 8.3 Hz, 1H), 7.31–8.33(m,8H), 8.69 (dd,J = 1.6, 4.8 Hz,1H), 9.07 (d,J = 1.6 Hz,1H) | — | C$_{21}$H$_{15}$N$_2$O$_4$Na.3H$_2$O<br>  C    H    N<br>Found 57.62 4.51 6.52<br>Calcd. 57.80 4.85 6.42 |
| 171 (33b) | white solid | 248.5–250 (dec.) (isopropanol) | (DMSO-d$_6$) 5.07 & 5.11(ABq, J = 16.7 Hz,2H), 5.23 & 5.86 (ABq,J = 13.3 Hz,2H), 6.13(d, J = 6.8 Hz,1H), 6.94(d,J = 8.5 Hz,1H), 7.32–7.69(m,6H), 7.78(dd,J = 2.2, 8.5 Hz,1H), 8.03(d,J = 2.2 Hz,1H), 9.06(s,1H), 9.72(d,J = 6.8 Hz,1H) | (KBr tablet) 1683, 1610, 1550, 1494, 1384, 1264, 1215, 1124, 995, 763 | C$_{20}$H$_{17}$N$_3$O$_4$<br>  C    H    N<br>Found 66.00 4.85 11.33<br>Calcd. 66.11 4.72 11.56 |

EXAMPLE 172

Methyl (E)-11-[2-(3-oxo-1-indazolyl)ethylidene]-6,11-dihydrodibenz[b,e]oxepin-2-carboxylate (Compound E-125a)

Methyl (E)-11-(2-chloroethylidene)-6,11-dihydrodibenz[b,e]oxepin-2-carboxylate (Compound h), 2.0 g, obtained in Reference Example 8, 4.3 g of 3-indazolinone and 14 ml of Triton B were heated to reflux in 100 ml of dioxane for 5 hours. After allowing to cool, the solvent was distilled off under reduced pressure. The obtained residue was extracted with 200 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=50:10:1) to give 0.5 g of the product.

EXAMPLE 173

Methyl (E)-11-[2-[(2H-1,4-benzothiazin-3(4H)-on)-4-yl]ethylidene]-6,11-dihydrodibenz[b,e]oxepin-2-carboxylate (Compound E-163a)

In 20 ml of N,N-dimethylformamide, 2.6 g of 2H-1,4-benzthiazin-3(4H)-one was stirred at room temperature for 2 hours, together with 0.6 g of sodium hydride (60% oily). Then 1.0 g of Compound h was added thereto followed by further stirring at room temperature overnight. The reaction mixture was extracted with 200 ml of ethyl acetate. The extract was washed successively solvent; toluene:ethyl acetate=5:1) to give 0.8 g of the crude product.

EXAMPLE 174

Methyl (E)-11-[2-(1,1,3-trioxo-2,3-dihydro-1,2-benzisothiazol-2-yl)ethylidene]-6,11-dihydrodibenz[b,e]oxepin-2-carboxylate (Compound E-164a)

The product was prepared in the same way as in EXAMPLE 173 except that saccharin was used in place of 2H-1,4-benzthiazin-3(4H)-one.

EXAMPLE 175

Methyl (E)-11-[2-[(2-hydroxy-1-benzimidazolyl)ethylidene]-6,11-dihydrodibenz[b,e]oxepin-2-carboxylate (Compound E-115a)

Compound h, 2.0 g and 4.3 g of 2-hydroxybenzimidazole were treated in a manner similar to Example 173 to give 0.3 g of the objective compound.

EXAMPLE 176

Methyl (E)-11-[2-(3-indolyl)]ethylidene]-6,11-dihydrodibenz[b,e]oxepin-2-carboxylate (Compound E-122a)

In 40 ml of tetrahydrofuran was dissolved 1.1 g of indole. Under ice cooling, 9.5 ml of 1N ethyl magnesium bromide was dropwise added to the solution. The mixture was stirred at room temperature for further 2 hours. Then, 30 ml of a tetrahydrofuran solution containing 2.0 g of Compound h was dropwise added to the reaction mixture under ice cooling. After stirring at room temperature for 2 hours, 10 ml of ammonium chloride aqueous solution was added to the mixture followed by stirring for 30 minutes. The reaction mixture was extracted with 300 ml of ethyl acetate. The extract was washed successively with saturated sodium bicarbonate aqueous solution and saturated sodium chloride aqueous solution. After drying over anhydrous magnesium sulfate, the solvent was distilled off under reduced pressure. The resulting residue was subjected to silica gel column chromatography (eluting solvent; hexane:ethyl acetate:triethylamine=50:10:1) to give 0.7 g of the product.

EXAMPLE 177

Methyl (E)-11-[2-(3-pyridyl)ethylidene]-6,11-dihydrodibenz[b,e]oxepin-2-carboxylate (Compound E-36b)

To 50 ml of pyridine was added 2.0 g of lithium aluminum hydride, and the mixture was stirred at room temperature for one night. Then, 90 ml of tetrahydrofuran solution containing 5.0 g of Compound h was dropwise added thereto under ice-cooling. The mixture was stirred at room temperature for 5 hours, and the solvent was distilled off under reduced pressure.. The residue was washed with tetrahydrofuran, and the washings were concentrated under reduced pressure. The residue was subjected to silica gel column chromatography (eluting solvent; hexane:ethyl acetate:triethylamine=10:10:1) to give 1.7 g of the desired product.

Physicochemical properties of the compounds obtained in Examples 172 to 177 are shown in Table 5-17.

EXAMPLE 178

(E)-11-[2-(3-Oxo-1-indazolyl)ethylidene]-6,11-dihydrodibenz[b,e]oxepin-2-carboxylic acid .0.25 hydrate (Compound E-125b')

EXAMPLE 179

(E)-11-[2-[(2H-1,4-Benzothiazin-3(4H)-on)-4-yl]ethylidene]-6,11-dihydrodibenz[b,e]oxepin-2-carboxylic acid (Compound E-163b)

EXAMPLE 180

(E)-11-[2-(1,1,3-Trioxo-2,3-dihydro-1,2-benzisothiazol-2-yl]ethylidene]-6,11-dihydrodibenz[b,e]oxepin-2-carboxylic acid .0.8 isopropylether .monohydrate (Compound E-164b')

EXAMPLE 181

(E)-11-[2-[(2-Hydroxy-1-benzimidazolyl)ethylidene]-6,11-dihydrodibenz[b,e]oxepin-2-carboxylic acid (Compound E-115b)

EXAMPLE 182

(E)-11-[2-(3-Indolyl)]ethylidene]-6,11-dihydrodibenz[b,e]oxepin-2-carboxylic acid 0.2 hydrate (Compound E-122b')

EXAMPLE 183

(E)-11-[2-(3-Pyridyl)ethylidene]-6,11-dihydrodibenz[b,e]oxepin-2-carboxylic acid .0.4 isopropanol (Compound E-36b')

In Examples 178 through 183, the objective compounds were prepared by hydrolyzing esters of the corresponding oxepine derivatives in a manner similar to Example 14 or 15.

TABLE 5-17

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 172 (E-125a) | yellow oil | — | (CDCl$_3$) 3.89(s,3H), 5.01 (d,J = 6.8 Hz,2H), 5.0–5.5(b, 2H), 6.53(t,J = 6.8 Hz,1H), 6.80(d,J = 8.8 Hz,1H), 7.0–7.9(m,9H), 8.11(d,J = 2.2 Hz, 1H), 8.79(bs,1H) | (neat) 1718, 1499, 1255, 1122, 1010 | — |
| 173 (E-163a) | pale yellow oil | — | (CDCl$_3$) 3.36(s,2H), 3.84(s, 3H), 4.56-5.35(m,4H), 6.03 (t,J = 5.9 Hz,1H), 6.40–8.09 (m,11H) | (neat) 3024, 2948, 1714, 1669, 1605, 1374, 1246, 1117, 1005, 767, 730 | — |
| 174 (E-164a) | colorless amorphous | — | (CDCl$_3$) 3.87(s,3H), 4.55 (bs,2H), 4.5–5.8(b,2H), 6.21(t,J = 7.1 Hz,1H), 6.79(d, J = 8.8 Hz,1H), 7.2–8.1(m,9H), 8.01(d,J = 2.2 Hz,1H) | — | [MS(m/z): 461(M$^+$)] |
| 175 (E-115a) | pale yellow oil | — | (CDCl$_3$) 3.77(s,3H), 4.32–5.60(m,4H), 6.15(t,J = 7.4 Hz, 1H), 6.30–8.10(m,12H) | — | — |
| 176 (E-122a) | colorless amorphous | — | (CDCl$_3$) 3.63(d,J = 7.9 Hz,1H), 3.87(s,3H), 4.6–5.8(b,2H), 6.40(t,J = 7.6 Hz,1H), 6.77(d, J = 8.6 Hz,1H), 7.01–7.49(m, 9H), 7.77(dd,J = 2.0 & 8.6 Hz, 1H), 8.05(d,J = 2.0 Hz,1H) | (KBr tablet) 3372, 2966, 1701, 1605, 1487, 1242, 1118, 1003, 767, 740 | — |
| 177 (E-36a) | yellow oil | — | (CDCl$_3$) 3.53(d,J = 7.5 Hz,2H), 3.87(s,3H), 6.24(t,J = 7.5 Hz, 1H), 6.78(d,J = 8.6 Hz,1H), 7.79(dd,J = 2.2 & 8.6 Hz,1H), 8.01(d,J = 2.2 Hz,1H) | (neat) 1711, 1606, 1244, 1117, 1033 | [MS(m/z): 357(M$^+$)] |

Physicochemical properties of the compounds obtained in Examples 178 to 183 are shown in Table 5-18.

The structure of intermediates obtained in Reference Examples hereinafter are illustrated in Table 6.

TABLE 5-18

| Example No. (Compound No.) | Appearance | MP °C. (Solvent for recrystallization) | NMR (Solvent) δ, ppm | IR (Method) cm$^{-1}$ | Elemental analysis % |
|---|---|---|---|---|---|
| 178 (E-125b′) | white crystal | 205-207 (dec.) (isopropanol) | (DMSO-d$_6$) 4.94(bs,2H), 6.46 (t,J = 6.6 Hz,1H), 6.86(d,J = 8.5 Hz,1H), 6.98-7.04(m,1H), 7.29-7.62(m,7H), 7.75(dd, J = 2.2, 8.5 Hz,1H), 7.97(d, J = 2.2 Hz,1H), 11.90(bs,1H), 12.7(bs,1H) | (KBr tablet) 1692, 1625, 1605, 1521, 1364, 1311, 1242, 1162, 1004, 763, 742 | C$_{24}$H$_{18}$N$_2$O$_4$.0.25H$_2$O<br>  C    H    N<br>Found 71.46 4.51 6.78<br>Calcd. 71.54 4.63 6.95 |
| 179 (E-163b) | yellow powder | 213-216 (isopropyl ether) | (DMSO-d$_6$) 3.49(s,2H), 4.1-4.5(m,4H), 5.95(t,J = 6.5 Hz, 1H), 6.71(d,J = 8.2 Hz,1H), 6.78(d,J = 8.5 Hz,1H), 6.97-7.60(m,7H), 7.70(dd,J = 2.2, 8.5 Hz,1H), 7.87(d,J = 2.2 Hz, 1H) | (KBr tablet) 2926, 1660, 1601, 1374, 1262, 1250, 1001, 771, 744 | C$_{26}$H$_{21}$NO$_4$S<br>  C    H    N<br>Found 68.24 4.40 3.20<br>Calcd. 69.91 4.46 3.26 |
| 180 (E-164b′) | white solid | 150 (dec.) (isopropyl ether)* | (DMSO-d$_6$) 4.95 & 5.38(each bs,2H), 5.95(t,J = 7.0 Hz,1H), 6.80(d,J = 8.5 Hz,1H), 7.17-7.72(m,9H), 7.77(d,J = 2.2 Hz,1H) | (KBr tablet) 1680, 1603, 1313, 1250, 1160, 997 | C$_{24}$H$_{17}$NO$_6$S.0.8C$_6$H$_{14}$O.H$_2$O<br>  C    H    N<br>Found 63.16 5.55 2.50<br>Calcd. 63.21 5.56 2.56 |
| 181 (E-115b) | white solid | 293-295 (methanol) | (DMSO-d$_6$) 4.2-5.6(m,4H), 6.06(t,J = 6.6 Hz,1H), 6.67-6.69(m,1H), 6.81(d,J = 8.5 Hz, 1H), 6.91-6.97(m,3H), 7.44-7.60(m,4H), 7.71(dd,J = 2.2, 8.5 Hz,1H), 7.89(d,J = 2.2 Hz, 1H), 10.78(bs,1H) | (KBr tablet) 1698, 1644, 1605, 1487, 1406, 1373, 1310, 1245, 1002 | C$_{24}$H$_{18}$N$_2$O$_4$<br>  C    H    N<br>Found 72.29 4.43 6.84<br>Calcd. 72.35 4.55 7.03 |
| 182 (E-122b′) | white solid | 230-232 (acetonitrile) | (DMSO-d$_6$) 3.56(bs,2H), 5.05 & 5.55(each bs,2H), 6.32(t, J = 7.8 Hz,1H), 6.82(d,J = 8.5 Hz,1H), 6.94-7.59(m,8H), 7.19(d,J = 2.2 Hz,1H), 7.70 (dd,J = 2.2, 8.5 Hz,1H), 7.92 (d,J = 2.2 Hz,1H), 10.88(bs, 1H), 12.65(bs,1H) | (KBr tablet) 1684, 1605, 1406, 1316, 1247, 1000, 769, 741, | C$_{25}$H$_{19}$NO$_3$.0.2H$_2$O<br>  C    H    N<br>Found 78.15 5.04 3.39<br>Calcd. 77.99 5.08 3.64 |
| 183 (E-36b′) | white crystal | 252-255 (dec.) (isopropanol) | (DMSO-d$_6$) 3.51(bs,2H), 5.05 & 5.53(each bs,2H), 6.26(t, J = 7.6 Hz,1H), 6.82(d,J = 8.6 Hz,1H), 7.31-7.65(m,6H), 7.71(dd,J = 2.2 & 8.5 Hz,1H), 7.91(d,J = 2.2 Hz,1H), 8.41 (bs,2H) | (KBr tablet) 1702, 1606, 1487, 1428, 1242, 1126, 1000 | C$_{22}$H$_{17}$NO$_3$.0.8C$_3$H$_8$O<br>  C    H    N<br>Found 75.98 5.42 3.52<br>Calcd. 75.84 5.54 3.81 |

TABLE 6

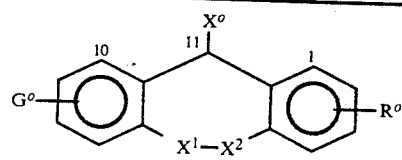

| Compound (Reference Example) | X$^1$—X$^2$ | G$^o$ | R$^o$ | —X$^o$ |
|---|---|---|---|---|
| a (1) | —CH$_2$O— | H | 2-COOCH$_3$ | =O |
| b (2) | ″ | ″ | ″ | —OH |
| c (3) | ″ | ″ | 2-COOC$_2$H$_5$ | ″ |

TABLE 6-continued

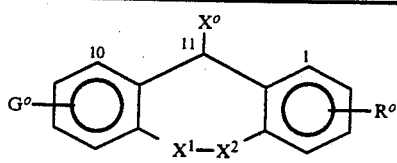

| Compound (Reference Example) | X¹—X² | G° | R° | —X° |
|---|---|---|---|---|
| d (4) | " | " | 2-COOn-C₄H₉ | " |
| e (5) | " | " | 2-CH₂COOCH₃ | =O |
| f (6) | " | " | " | —OH |
| g (7) | " | " | 2-C(CH₃)₂COOCH₃ | " |
| h (8) | " | " | 2-COOCH₃ | =CHCH₂Cl |
| i (9) | " | " | 3-COOCH₃ | " |
| j (10) | " | " | 9-COOCH₃ | " |
| k (11) | " | 9-Br | 2-COOCH₃ | " |
| l (12) | " | H | 2-CH₂COOCH₃ | " |
| m (13) | " | " | " | =CHCH₂CH₂OSO₂CH₃ |
| n (14) | " | " | " | —SCH₂CH₂I |
| o (15) | " | " | " | —NH₂ |
| p (16) | " | " | 3-COOCH₃ | —OCH₃ |
| q (17) | —CH₂S— | " | 2-COOCH₃ | " |
| r (18) | —CH₂CH₂— | H | 2-COOCH₃ | =CHCH₂Cl |
| s (19) | " | " | 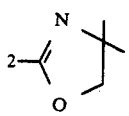 | —CH₂CH₂OH |
| t (20) | —CH=CH— | " | 2-COOCH₃ | =CHCH₂Cl |
| u (21) | " | " | 2-CH₂COOCH₃ | " |
| v (22) | " | " | 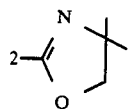 | —CH₂CH₂OH |

REFERENCE EXAMPLE 1

Methyl 11-oxo-6,11-dihydrodibenz[b,e]oxepin-2-carboxylate (Compound a)

A mixture of 348.9 g of methyl p-hydroxybenzoate sodium salt, 402.4 g of phthalide and 200 g of sodium chloride was stirred at 150° C. for 6 hours. After completion of the reaction, the reaction mixture was cooled to room temperature and 4 liters of 10 % acetic acid aqueous solution were added thereto. The mixture was allowed to stand at room temperature overnight. After stirring at room temperature for 3 hours, crystals were taken by filtration. To the crystals was added 6 liters of water. After stirring at room temperature for 30 minutes, the crystals were taken out by filtration. To the crystals was added 3 liters of toluene. The mixture was stirred at room temperature for an hour. The crystals were taken out by filtration and dried by heating under reduced pressure to give 393.9 g of 2-(4-methoxycarbonylphenoxy)methyl benzoate.

IR (KBR tablet, cm⁻¹): 3400, 1700, 1610, 1260, 1235

In 5.0 liters of methylene chloride was suspended 392.7 g of the thus obtained phenoxy compound and, 266.0 g of trifluoroacetic anhydride was added to the suspension. After stirring at room temperature for an hour, 19.4 g of boron trifluoride ethyl ether complex was added to the mixture followed by stirring at room temperature for 2 hours. The reaction solution was poured into ice water. After fractionation, the organic phase was washed with a diluted sodium hydroxide aqueous solution and then with water and dried over anhydrous magnesium sulfate. Concentration under reduced pressure gave 335.3 g of the product as white crystals (recrystallized from isopropyl ether).

Melting point: 128°–129° C.

| Elemental analysis: as C₁₆H₁₂O₄ | | |
|---|---|---|
| | C | H |
| Found (%) | 71.55 | 4.48 |
| Calcd. (%) | 71.63 | 4.51 |

NMR (CDCl₃, δ, ppm): 3.84(s, 3 H), 5.14(s, 2 H), 6.87–8.93(m, 7 H)

IR (KBr tablet, cm⁻¹): 1710, 1650, 1610, 1250, 1010

REFERENCE EXAMPLE 2

Methyl 11-hydroxy-6,11-dihydrodibenz[b,e]oxepin-2-carboxylate (Compound b)

Compound a, 50 g, obtained in Reference Example 1 was suspended in 300 ml of methanol and 6.3 g sodium borohydride was added to the suspension. The mixture was stirred at room temperature for 2 hours. After completion of the reaction, 10 ml of acetic acid and 300 ml of water were added thereto followed by stirring for 30 minutes. Insoluble matters were taken out by filtration and washed with methanol and then with water. By drying with heating under reduced pressure, 40 g of the product was obtained.

NMR (CDCl₃, δ, ppm): 2.16(s, 6 H), 2.30–2.76(m, 4 H), 3.83(s, 3 H), 4.83 and 6.40(ABq, J=12.6 Hz, 2 H), 5.01(s, 1 H), 6.79–7.93(m, 7 H)

IR (neat, cm⁻¹): 2950, 1710, 1240, 1015

REFERENCE EXAMPLE 3

Ethyl 11-hydroxy-6,11-dihydrodibenz[b,e]oxepin-2-carboxylate (Compound c)

The corresponding starting material was used and treated in a manner similar to Reference Examples 1 and 2 to give the product as colorless oil.

NMR (CDCl₃, δ, ppm): 1.31(t, J=7 Hz, 3 H), 3.60(d, J=3 Hz, 1 H), 4.25(q, J=7 Hz, 2 H), 4.91 and 5.95(ABq, J=12.5 Hz, 2 H), 5.61(d, J=3 Hz, 1 H), 6.69–8.12(m, 7 H)

IR (neat, cm⁻¹): 3430, 1675, 1610, 1480, 1250

REFERENCE EXAMPLE 4 n-Butyl 11-hydroxy-6,11-dihydrodibenz[b,e]oxepin-2-carboxylate (Compound d)

The corresponding starting material was used and treated in a manner similar to Reference Examples 1 and 2 to give the product as white crystals (recrystallized from isopropyl ether).

Melting point: 108°–110° C.

NMR (CDCl₃, δ, ppm): 0.7–2.0(m, 7 H), 3.21(bs, 1 H), 4.23(t, J=6.3 Hz, 2 H), 4.94 and 5.98(ABq, J=12.7 Hz, 2 H), 5.62(s, 1 H), 6.79(d, J=8.4 Hz, 1 H), 7.2–7.4 (m, 4 H), 7.77(dd, J=2.3, 8.4 Hz, 1 H), 7.99(d, J=2.3 Hz, 1 H)

REFERENCE EXAMPLE 5

Methyl 11-oxo-6,11-dihydrodibenz[b,e]oxepin-2-acetate (Compound e)

The corresponding starting material was treated in a manner similar to Reference Example 1 to give the product as pale yellow crystals (recrystallized from methanol).

Melting point: 75°–76° C.

REFERENCE EXAMPLE 6

Methyl 11-hydroxy-6,11-dihydrodibenz[b,e]oxepin-2-acetate (Compound f)

The compound e obtained in Reference Example 5 was treated in a manner similar to Reference Example 2 to give the product as pale yellow crystals (recrystallized from diethyl ether).

Melting point: 85°–87° C.

NMR (CDCl₃, δ, ppm): 2.08(s, 3 H), 3.49(s, 2 H), 3.59 (s, 3 H), 4.89 and 5.75(ABq, J=13 Hz, 2 H), 5.54(bs, 1 H), 6.7–7.4(m, 7 H)

REFERENCE EXAMPLE 7

Methyl 2-(11-hydroxy-6,11-dihydrodibenz[b,e]oxepin)-2-yl)-2-methylpropionate (Compound g)

The corresponding starting material was treated in a manner similar to Reference Examples 1 and 2 to give the product as colorless oil.

NMR (CDCl₃, δ, ppm): 1.56(s, 6 H), 3.62(s, 3 H), 4.97 and 5.90(ABq, J=13.1 Hz, 2 H), 5.61(s, 1 H), 6.87(d, J=8.3 Hz, 1 H), 7.05–7.40(m, 6 H)

IR (neat, cm⁻¹): 3418, 1708, 1610, 1231, 1012

REFERENCE EXAMPLE 8

Methyl (E)-11-(2-chloroethylidene-6,11-dihydrodibenz[b,e]oxepin-2-carboxylate (Compound h)

1-Methylpiperazine, 30 ml, and 74 g of paraformaldehyde were dissolved in 2 l of tetrachloroethane and 100 ml of trifluoroacetic acid was dropwise added to the solution. After stirring at 60° C. for 2 hours, a solution of 36 g of methyl 11-methylene-6,11-dihydrodibenz[b,e]oxepin-2-carboxylate in 600 ml of tetrachloroethane was dropwise added to the reaction mixture followed by stirring at 90° C. for further 3 hours. The reaction mixture was concentrated to dryness under reduced pressure and 4N hydrochloric acid aqueous solution was added to the residue to adjust pH to 1. Then, the mixture was washed with diethyl ether. Thereafter, 10N sodium hydroxide aqueous solution was added to adjust pH to 13. Extraction was performed with 3 l of methylene chloride. After washing with saturated sodium chloride aqueous solution and drying over anhydrous sodium sulfate, the solvent was distilled off under reduced pressure. The resulting residue was subjected to silica gel column chromatography (eluting solvent; hexane:ethyl acetate:triethylamine=5:5:1) to give 44 g of colorless oily methyl 11-[2-(4-methyl-1-piperazinyl)ethylidene]-6,11-dihydrodibenz[b,e]oxepin-2-carboxylate.

MS (m/z): 378 (M⁺)

NMR (CDCl₃, δ, ppm): 2.24(s, 3 H), 2.45(s, 8 H), 2.94–3.32(m, 2 H), 3.84(s, 3 H), 5.22(bs, 2 H), 5.85 and 6.22(t, J=6.8 Hz, 1 H), 6.66–8.07(m, 7 H)

E-form compound, 21.5 g, isolated from the Z/E mixture described above according to the conventional manner and 23.5 g of sodium acetate were suspended in 250 ml of dichloroethane and, 27.1 ml of ethyl chloroformate was dropwise added to the suspension. After completion of the dropwise addition, the mixture was stirred at room temperature for an hour and the solvent was distilled off under reduced pressure. The residue was extracted with 400 ml of ethyl acetate. After washing with saturated sodium chloride aqueous solution and drying over anhydrous sodium sulfate, the solvent was distilled off under reduced pressure. The obtained crude product was recrystallized from isopropanol to give 14.3 g of the product as white crystals.

Melting point: 134°–135° C.

| Elemental analysis: as C₁₈H₁₅ClO₃ | | |
|---|---|---|
| | C | H |
| Found (%) | 68.55 | 4.77 |
| Calcd. (%) | 68.68 | 4.80 |

NMR (CDCl₃, δ, ppm): 3.90(s, 3 H), 4.16(d, J=8.1 Hz, 2 H), 4.88(bs, 1 H), 5.57(bs, 1 H), 6.31(t, J=8.1 Hz, 1 H), 6.79–8.04(m, 7 H)

REFERENCE EXAMPLE 9

Methyl (E)-11-(2-chloroethylidene)-6,11-dihydrodibenz[b,e]oxepin-3-carboxylate (Compound i)

The corresponding starting material was treated in a manner similar to Reference Example 8 to give the product as white crystals.

Melting point: 102°–104° C.

| Elemental analysis: as C₁₈H₁₅ClO₃ | | |
|---|---|---|
| | C | H |
| Found (%) | 68.50 | 4.71 |
| Calcd. (%) | 68.68 | 4.80 |

NMR (CDCl₃, δ, ppm): 3.87(s, 3 H), 4.14(d, J=8.0 Hz, 2 H), 5.22(bs, 2 H), 6.29(t, J=8.0 Hz, 1 H), 7.26–7.61(m, 7 H)

IR (KBr tablet, cm$^{-1}$): 1718, 1558, 1293, 1235, 1095, 1028

REFERENCE EXAMPLE 10

Methyl (E)-11-(2-chloroethylidene)-6,11-dihydrodibenz[b,e]oxepin-9-carboxylate (Compound j)

The corresponding starting material was treated in a manner similar to Reference Example 8 to give the product as white solid.

Melting point: 83°–85° C.

| Elemental analysis: as $C_{18}H_{15}ClO_3$ | | |
|---|---|---|
| | C | H |
| Found (%) | 68.49 | 4.81 |
| Calcd. (%) | 68.68 | 4.80 |

NMR (CDCl$_3$, δ, ppm): 3.92(s, 2 H), 4.12(d, J=8.1 Hz, 2 H), 5.21(bs, 2 H), 6.27(t, J=8.1 Hz, 1 H), 6.7–8.1 (m, 7 H)

IR (KBr tablet, cm$^{-1}$): 1696, 1290, 1262, 1222, 1101, 1008

REFERENCE EXAMPLE 11

Methyl 9-bromo-11-(2-chloroethylidene)-6,11-dihydrodibenz[b,e]oxepin-2-carboxylate (Compound k)

The corresponding starting material was treated in a manner similar to Reference Example 8 to give the product as pale yellow oil.

NMR (CDCl$_3$, δ, ppm): 3.88(s, 3 H), 4.13(d, J=7.5 Hz, 2 H), 4.7–5.6(m, 2 H), 6.36(t, J=7.5 Hz, 1 H), 6.8–8.2(m, 6 H)

REFERENCE EXAMPLE 12

Methyl (E)-11-(2-chloroethylidene)-6,11-dihydrodibenz[b,e]oxepin-2-acetate (Compound l)

The corresponding starting material was treated in a manner similar to Reference Example 8 to give the product as white crystals (recrystallized from isopropanol).

Melting point: 127°–128° C.

| Elemental analysis: as $C_{19}H_{17}ClO_3$ | | |
|---|---|---|
| | C | H |
| Found (%) | 69.21 | 5.35 |
| Calcd. (%) | 69.41 | 5.21 |

NMR (CDCl$_3$, δ, ppm): 3.55(s, 2 H), 3.69(s, 3 H), 4.14 (d, J=8.1 Hz, 2 H), 4.7–5.4(m, 2 H), 6.23(t, J=8.1 Hz, 1 H), 6.74(d, J=8.1 Hz, 1 H), 6.95–7.40(m, 6 H)

IR (KBr tablet, cm$^{-1}$): 1734, 1489, 1284, 1257, 1227, 1138, 1004

REFERENCE EXAMPLE 13

Methyl (Z,E)-11-[3-(methylsulfonyl)oxy]propylidene-6,11-dihydrodibenz[b,e]oxepin-2-carboxylate (Compound m)

[3-[(Tetrahydro-2H-pyran-2-yl)oxy]propyl]triphenylphosphonium bromide, 40.0 g, was suspended in 250 ml of tetrahydrofuran. Under ice cooling in nitrogen atmosphere, 50 ml of n-butyl lithium/hexane solution (1.6N) was dropwise added to the suspension. After stirring at room temperature for further an hour, 15.0 g of Compound a obtained in Reference Example 1 was added thereto followed by stirring at room temperature for 12 hours. After 50 ml of water was added to the reaction mixture, it was extracted with 1 l of ethyl acetate. After washing thrice with saturated sodium chloride aqueous solution and drying over anhydrous sodium sulfate, the solvent was distilled off under reduced pressure. The obtained residue was dissolved in 500 ml of dioxane and 200 ml of water and 1.0 g of p-toluenesulfonic acid were added to the solution followed by heating to reflux for an hour. The mixture was concentrated under reduced pressure. The obtained residue was extracted with 1 l of ethyl acetate. After washing successively with saturated sodium bicarbonate aqueous solution and saturated sodium chloride aqueous solution, the extract was dried over anhydrous sodium sulfate. The solvent was distilled off under reduced pressure The resulting residue was subjected to silica gel column chromatography (eluting solvent; toluene:ethyl acetate=1:1) to give 9.8 g of methyl (Z,E)-11-(3-hydroxy)propylidene-6,11-dihydrodibenz[b,e]oxepin-2-carboxylate.

NMR (CDCl$_3$, δ, ppm): 2.17–2.72(m, 2 H), 3.37–3.76(m, 2 H), 3.77(s, 3 H), 4.68–5.43(m, 1 H), 5.70(t, J=7.4 Hz, 0.9 H; Z-form), 6.40(t, J=6.9 Hz, 2.1 H; E-form), 6.52–8.12(m, 7 H)

The thus obtained hydroxy product, 3.5 g, was dissolved in 50 ml of pyridine and 1.7 ml of methanesulfonyl chloride was dropwise added under ice cooling. After stirring for further an hour under ice cooling, the solvent was distilled off under reduced pressure. The residue was extracted with 200 ml of ethyl acetate. The extract was washed in succession with 1N hydrochloric acid aqueous solution, saturated sodium bicarbonate aqueous solution and saturated sodium chloride aqueous solution. After drying over anhydrous sodium sulfate, the solvent was distilled off under reduced pressure to give 4.3 g of the product (Z/E=7/3) as colorless oil.

NMR (CDCl$_3$, δ, ppm): 2.5–3.0(m, 2 H), 3.00(s, 3 H), 3.86 (s, 3 H), 4.37(t, J=6.3 Hz, 2 H), 5.26(bs, 1 H), 5.74 and 6.09(each t, J=7.5 Hz, 1 H), 6.7–8.1(m, 7 H)

REFERENCE EXAMPLE 14

Methyl 11-(2-iodoethyl)thio-6,11-dihydrodibenz[b,e]oxepin-2-carboxylate (Compound n)

In 400 ml of methylene chloride was suspended 40.0 g of Compound b obtained in Reference Example 2. Trifluoroacetic anhydride, 21.0 ml, was added to the suspension followed by stirring at room temperature for an hour. Then, 10.7 ml of 2-mercaptoethanol was added to the mixture followed by stirring for further 4 hours. After 100 ml of methylene chloride was added to the reaction mixture, the mixture was washed with saturated aqueous sodium chloride solution. After drying over anhydrous magnesium sulfate, the solvent was distilled off under reduced pressure. The obtained crude product was recrystallized from toluene to give 37.6 g of methyl 11-(2-hydroxyethyl)thio-6,11-dihydrodibenz[b,e]oxepin-2-carboxylate as white crystals.

Melting point: 128°–130° C.

| Elemental analysis: as $C_{18}H_{18}O_4S$ | | |
|---|---|---|
| | C | H |
| Found (%) | 65.26 | 5.55 |
| Calcd. (%) | 65.43 | 5.49 |

NMR (CDCl$_3$, δ, ppm): 2.66(dt, J=2.1, 6.0 Hz, 2 H), 3.69 (t, J=5.9 Hz, 2 H), 3.89(s, 3 H), 4.91 and 6.43(ABq, J=12.7 Hz, 2 H), 5.09(s, 1 H), 6.82–7.98(m, 7 H)

IR (KBr tablet, cm$^{-1}$): 3420, 1708, 1683, 1610, 1437, 1318, 1008

The thus obtained hydroxyethyl compound, 20.0 g, was dissolved in 200 ml of dimethylformamide, and 12 ml of 2,4,6-cholidine and 4.0 g of lithium chloride were added to the solution. Under ice cooling, 5.4 ml of methanesulfonyl chloride was dropwise added to the mixture. After stirring at room temperature overnight, the solvent was distilled off under reduced pressure. The residue was extracted with ethyl acetate. The extract was washed, in succession, with 1N hydrochloric acid aqueous solution and then with saturated aqueous sodium chloride solution. After drying over anhydrous magnesium sulfate, the solvent was distilled off under reduced pressure. The obtained residue was subjected to silica gel column chromatography (eluting solvent; hexane:ethyl acetate=5:1) and further crystallized from hexane to give 20.8 g of methyl 11-(2-chloroethyl)thio-6,11-dihydrodibenz[b,e]oxepin-2-carboxylate.

Melting point: 100°-102° C.

| Elemental analysis: as $C_{18}H_{17}ClO_3S$ | | |
| --- | --- | --- |
| | C | H |
| Found (%) | 61.77 | 4.80 |
| Calcd. (%) | 61.97 | 4.91 |

NMR (CDCl$_3$, δ, ppm): 2.54–3.62(m, 4 H), 3.84(s, 3 H), 5.04(s, 1 H), 4.87 and 6.37(ABq, J=13.2 Hz, 2 H), 6.76–8.12(m, 7 H)

The thus obtained chloroethyl compound, 10.1 g, obtained as above was dissolved in 150 ml of acetonitrile, and 14.6 g of sodium iodide was added to the solution. The mixture was heated to reflux for 5 hours. After allowing to cool, the reaction mixture was extracted with ethyl acetate and the extract was washed twice with saturated sodium chloride aqueous solution. After drying over anhydrous magnesium sulfate, the solvent was distilled off under reduced pressure. The residue was subjected to silica gel column chromatography (eluting solvent; hexane:ethyl acetate=10:1) and further solidified with hexane to give 3.1 g of the product as white solid.

Melting point: 111°-113° C.

| Elemental analysis: as $C_{18}H_{17}IO_3S$ | | |
| --- | --- | --- |
| | C | H |
| Found (%) | 49.08 | 3.71 |
| Calcd. (%) | 49.10 | 3.89 |

NMR (CDCl$_3$, δ, ppm): 2.68–3.22(m, 4 H), 3.88(s, 3 H), 5.09(s, 1 H), 4.91 and 6.37(ABq, J=13.2 Hz, 2 H), 6.78–8.08(m, 7 H)

REFERENCE EXAMPLE 15

Methyl 11-amino-6,11-dihydrodibenz[b,e]oxepin-2-carboxylate (Compound o)

The product was synthesized as white solid in a manner similar to the method of Example 32 in Japanese Published Unexamined Patent Application No. 21679/1983.

Melting point: 99°-100° C.

NMR (CDCl$_3$, δ, ppm): 3.82(s, 3 H), 4.95 and 6.21(ABq, J=12.6 Hz, 2 H), 5.14(s, 1 H), 6.80(t, J=9.0 Hz, 1 H), 7.0–7.3(m, 4 H), 7.74(dd, J=2.0, 9.0 Hz, 1 H), 7.93 (d, J=2.0 Hz, 1 H)

REFERENCE EXAMPLE 16

Methyl 11-methoxy-6,11-dihydrodibenz[b,e]oxepin-3-carboxylate (Compound p)

3-Bromo-11-methoxy-6,11-dihydrodibenz[b,e]oxepine, 30 g, was dissolved in 500 ml of tetrahydrofuran. After cooling to −78° C., 65 ml of 1.6N n-butyl lithium/hexane solution was dropwise added to the solution in a nitrogen atmosphere followed by stirring at −78° C. for further 40 minutes. The reaction solution was dropwise added onto 100 g of dry ice, which was allowed to stand to elevate to room temperature. The solvent was distilled off under reduced pressure. To the residue obtained, were added 500 ml of methanol and 10 ml of conc. sulfuric acid. The mixture was heated to reflux for 2 hours. After allowing to cool, the solvent was distilled off under reduced pressure. The residue was extracted with 500 ml of ethyl acetate. After washing successively with saturated sodium chloride aqueous solution, saturated sodium bicarbonate aqueous solution and saturated sodium chloride aqueous solution, the extract was dried over anhydrous magnesium sulfate. The solvent was then distilled off under reduced pressure. The residue was subjected to silica gel column chromatography (eluting solvent; hexane:ethyl acetate=1:1) to give 19.3 g of the product as pale yellow oil.

NMR (CDCl$_3$, δ, ppm): 3.34(s, 3 H), 3.86(s, 3 H), 4.93 and 5.99(ABq, J=12.4 Hz, 2 H), 5.07(s, 1 H), 7.24–7.62(m, 7 H)

REFERENCE EXAMPLE 17

Methyl 11-methoxy-6,11-dihydrodibenzo[b,e]thiepin-2-carboxylate (Compound q)

p-Bromothiophenol, 50.0 g, was suspended in 150 ml of methanol and 14.9 g of sodium methoxide was added to the suspension followed by stirring at 50° C. for an hour. The solvent was distilled off under reduced pressure and 35.5 g of phthalide was added to the residue followed by stirring at 180° C. for 3 hours. After allowing to cool to room temperature, 200 ml of water was added to the reaction mixture. The mixture was dissolved with heating. After allowing to cool, pH was adjusted to 1.5 with conc. hydrochloric acid. The precipitated crude product was taken by filtration. After drying, the crude product was further recrystallized from toluene to give 56.3 g of 2-[(4-bromophenyl)thio]-methylbenzoic acid.

Melting point: 139°-140° C.

The aforesaid compound, 12.0 g, was stirred at 90° C. together with 120.0 g of polyphosphoric acid. The reaction solution was poured onto 1 liter of ice followed by stirring for further an hour. The precipitated crude product was taken by filtration. After drying, the crude product was further recrystallized from toluene to give 9.0 g of 2-bromo-11-oxo-6,11-dihydrodibenzo[b,e]thiepine.

Melting point: 151°-152° C.

The aforesaid compound, 20.0 g, was suspended in a solvent mixture of 500 ml of methanol and 300 ml of tetrahydrofuran and 4.5 g of sodium borohydride was added to the suspension followed by stirring at room temperature for an hour. The solvent was distilled off under reduced pressure and the residue was recrystallized from methanol to give 12.0 g of 2-bromo-11-hydroxy-6,11-dihydrodibenzo[b,e]thiepine.

Melting point: 169°-170° C.

The aforesaid compound, 8.6 g, was suspended in 180 ml of methanol and 0.5 g of p-toluenesulfonic acid was added to the suspension followed by heating to reflux for an hour. The solvent was distilled off under reduced pressure and the residue was extracted with 200 ml of ethyl acetate. After washing successively with saturated sodium chloride aqueous solution and then with saturated sodium bicarbonate aqueous solution, the extract was dried over anhydrous sodium sulfate. The solvent was distilled off under reduced pressure. The resulting crude product was recrystallized from hexane to give 7.8 g of 2-bromo-11-methoxy-6,11-dihydrodibenzo[b,e]thiepine.

Melting point: 68°–71° C.

The aforesaid compound, 19.0 g, and 8.0 g of cuprous cyanide were heated to reflux in 100 ml of dimethylformamide for 8 hours. After allowing to cool, 25 ml of ethylenediamine was added thereto. The mixture was stirred at 60° C. for 30 minutes and 100 ml of water was added thereto followed by stirring at 60° C. for further 30 minutes. After allowing to cool, the reaction mixture was extracted with 500 ml of ethyl acetate. Insoluble matters were filtered off and washed 3 times with saturated sodium chloride aqueous solution. After drying over anhydrous sodium sulfate, the solvent was distilled off under reduced pressure. The resulting residue was subjected to silica gel column chromatography (eluting solvent; hexane:ethyl acetate=1:1) and further recrystallized from ethanol to give 11.3 g of 11-methoxy-2-cyano-6,11-dihydrodibenzo[b,e]thiepine.

Melting point: 117°–118° C.

The aforesaid compound, 7.3 g, was heated to reflux in a solvent mixture of 300 ml of conc. hydrochloric acid and 200 ml of acetic acid for 8 hours. The solvent was distilled off under reduced pressure and 200 ml of methanol and 0.5 g of p-toluenesulfonic acid were added to the obtained residue. The mixture was heated to reflux for 3 hours. After allowing to cool, the solvent was distilled off under reduced pressure and the residue was extracted with 500 ml of ethyl acetate. After washing successively with saturated sodium chloride aqueous solution and then with saturated sodium bicarbonate aqueous solution, the extract was dried over anhydrous sodium sulfate. The solvent was distilled off under reduced pressure. The resulting residue was subjected to silica gel column chromatography (eluting solvent; hexane:ethyl acetate=5:1) to give 4.5 g of the product as pale yellow amorphous.

IR (CHCl$_3$, cm$^{-1}$): 2994, 2952, 1715, 1437, 1301, 1120

REFERENCE EXAMPLE 18

Methyl (Z,E)-5-(2-chloroethylidene)-10,11-dihydro-5H-dibenzo[a,d]cyclohepten-3-carboxylate (Compound r)

The corresponding starting material was used and treated in a manner similar to Reference Example 8 to give the product (Z/E=7/3) as pale yellow oil.

NMR (CDCl$_3$, δ, ppm): 2.8–3.4(m, 4 H), 3.87(s, 2 H), 3.89(s, 1 H), 4.0–4.3(m, 2 H), 6.09(t, J=7.6 Hz, 0.7 H; Z-form), 6.11(t, J=7.6 Hz, 0.3 H; E.-form), 7.0–7.3(m, 5 H), 7.7–8.0(m, 2 H)

REFERENCE EXAMPLE 19

5-(2-Hydroxyethyl)-3-(4,4-dimethyl-2)oxazolin-2-yl)-10,11-dihydro-5H-dibenzo[a,d]cycloheptene (Compound s)

Sodium hydride, 4.9 g, was added to 100 ml of a solution of 22 ml of ethyl diethylphosphonoacetate in tetrahydrofuran followed by stirring at room temperature for 15 minutes. Then, 100 ml of 6.8 g of 5-oxo-3-(4,4-dimethyl-2-oxazolin-2-yl)-6,11-dihydro-5 H-dibenzo[a,d]cycloheptene in tetrahydrofuran was dropwise added to the mixture. The resulting mixture was heated to reflux for an hour. To the reaction solution was added 30 ml of ice water followed by extracting with 300 ml of ethyl acetate. The extract was successively washed with 1N hydrochloric acid aqueous solution, saturated sodium bicarbonate aqueous solution and then saturated sodium chloride aqueous solution. After drying over anhydrous magnesium sulfate, the solvent was distilled off under reduced pressure. The obtained residue was subjected to silica gel column chromatography (eluting solvent; hexane:ethyl acetate=3:1) to give 2.1 g of (Z,E)-5-(ethoxycarbonylmethylene)-3-(4,4-dimethyl-2-oxazolin-2-yl)-10,11-dihydro-5H-dibenzo[a,d]cycloheptene as pale yellow oil.

NMR (CDCl$_3$, δ, ppm): 1.11(t, J=7.0 Hz, 3 H), 1.38(s, 6 H), 2.94–3.36(m, 4 H), 4.05(q, J=7.0 Hz, 2 H), 4.09(s, 2 H), 6.29(s, 1 H), 7.06–7.29(m, 5 H), 7.75(dd, J=1.8, 7.9 Hz, 1 H), 7.94(d, J=1.8 Hz, 1 H)

The thus obtained compound, 1.6 g, was dissolved in 50 ml of tetrahydrofuran and 0.7 g of lithium aluminum hydride was added to the solution followed by stirring at room temperature for 30 minutes. Then, methanol, water and 1N hydrochloric acid aqueous solution were dropwise added to the mixture in succession. Thereafter, inorganic residue was filtered off. To the filtrate was added 200 ml of ethyl acetate. The mixture was washed with saturated aqueous sodium chloride solution. After drying over anhydrous magnesium sulfate, the solvent was distilled off under reduced pressure to give 0.36 g of the product as pale yellow oil.

NMR (CDCl$_3$, δ, ppm): 1.35(s, 6 H), 2.22–2.45(m, 3 H), 2.94–3.58(m, 4 H), 3.58(t, J=6.4 Hz, 2 H), 4.06(s, 2 H), 4.29(t, J=7.5 Hz, 1 H), 7.08–7.26(m, 5 H), 7.65 (dd, J=1.5, 7.8 Hz, 1 H), 7.82(d, J=1.5 Hz, 1 H)

REFERENCE EXAMPLE 20

Methyl (Z,E)-5-(2-chloroethylidene)-5H-dibenzo[a,d]cyclohepten-3-carboxylate (Compound t)

The corresponding starting material was treated in a manner similar to Reference Example 8 to give the product (Z/E=1/1) as pale yellow oil.

NMR (CDCl$_3$, δ, ppm): 3.92(s, 3H), 4.03(d, J=7.9 Hz, 1 H), 4.05(d, J=8.1 Hz, 1 H), 5.81(t, J=7.9 Hz, 0.5 H; Z-form), 5.82(t, J=8.1 Hz, 0.5 H; E-form), 6.90(s, 1 H), 6.92(s, 1 H), 7.1–7.5(m, 5 H), 7.8–8.1(m, 2 H)

REFERENCE EXAMPLE 21

Methyl (Z,E)-5-(2-chloroethylidene)-5H-dibenzo[a,d]cyclohepten-3-acetate (Compound u)

The corresponding starting material was treated in a manner similar to Reference Example 8 to give the product (Z/E=1/1) as pale yellow oil.

NMR (CDCl$_3$, δ, ppm): 3.62(s, 2 H), 3.64 and 3.65(each s, 3 H), 4.00 and 4.01 (each d, J=8.1 Hz, 2 H), 5.75 and 5.76(each t, J=8.1 Hz, 1 H), 6.80(s, 2 H), 7.11–7.38(m, 7 H)

REFERENCE EXAMPLE 22

5-(2-Hydroxyethyl)-3-(4,4-dimethyl-2-oxazolin-2-yl)-5H-dibenzo[a,d]cycloheptene (Compound v)

The corresponding starting material was treated in a manner similar to Reference Example 19 to give the product as pale yellow oil.

NMR (CDCl$_3$, δ, ppm): 1.29(s, 6 H), 1.82–2.05(m, 2 H), 3.29(t, J=6.3 Hz, 2 H), 3.44–3.79(m, 1 H), 4.02(s, 2 H), 4.29(t, J=7.7 Hz, 1 H), 6.82(s, 1 H), 6.83(s, 1 H), 7.00–7.33(m, 5 H), 7.27(dd, J=1.6, 8.0 Hz, 1 H), 7.92(d, J=1.8 Hz, 1 H)

PHARMACEUTICAL PREPARATION 1: Tablet

A tablet having the following composition is prepared in a conventional manner.

| Compound E-89b' | 100 mg |
|---|---|
| Lactose | 60 mg |
| Potato starch | 30 mg |
| Polyvinyl alcohol | 2 mg |
| Magnesium stearate | 1 mg |
| Tar pigment | trace |

PHARMACEUTICAL PREPARATION 2: Powder

Powders having the following composition are prepared in a conventional manner.

| Compound E-62b | 20 mg |
|---|---|
| Lactose | 300 mg |

PHARMACEUTICAL PREPARATION 3: Syrup

Syrup having the following composition is prepared in a conventional manner.

| Compound E-41b' | 100 mg |
|---|---|
| Refined sugar | 30 mg |
| Ethyl p-hydroxybenzoate | 40 mg |
| Propyl p-hydroxybenzoate | 10 mg |
| Strawberry flavor | 0.1 cc |

Water is added to make the whole volume 100 cc.

PHARMACEUTICAL PREPARATION 4: Capsule

Capsule having the following composition is prepared in a conventional manner.

| Compound E-62b | 20 mg |
|---|---|
| Lactose | 200 mg |
| Magnesium stearate | 5 mg |

The composition was mixed and packed in a gelatin capsule.

PHARMACEUTICAL PREPARATION 5: Injection

Injection having the following composition is prepared in a conventional manner.

| Compound E-62b | 20 mg |
|---|---|
| Sodium chloride | 45 mg |

Water for injection was added to the composition to make the whole volume 5 ml (amount per 1 ampoule). The solution was distilled and sterilized in an autoclave.

What is claimed is:

1. A tricyclic compound of the formula

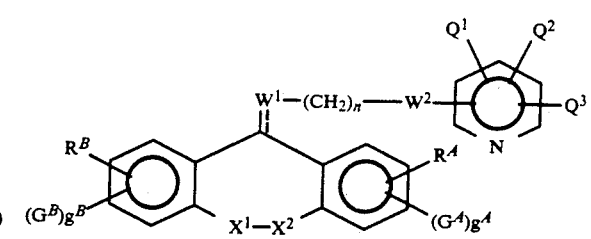

wherein:

------ is a single bond or a double bond;

$X^1$-$X^2$ is selected from the group consisting of;

—$CH_2$—O—, —$CH_2$—S—, —$CH_2$—$CH_2$— and —CH=CH—;

$G^A$ and $G^B$ are independently selected from the group consisting of:
lower alkyl, halogen and $OR^1$, wherein $R^1$ is hydrogen or lower alkyl;

$g^A$ and $g^B$ are independently 0, 1, 2 or 3;

one of $R^A$ and $R^B$ is hydrogen and the other is —Y—$COOR^{1a}$;

wherein $R^{1a}$ is hydrogen or lower alkyl; and Y is selected from the group consisting of a single bond, —$CR^{1b}$—$R^{1c}$—$(CH_2)_m$ and —$CR^{1b}$=$CR^{1c}$—$(CH_2)_m$— and each of $R^{1b}$ and $R^{1c}$ are independently hydrogen or lower alkyl and m is 0, 1, 2, 3 or 4, wherein the left side of Y is bound to the mother nucleus when Y is not a single bond;

$W^1$ is selected from the group consisting of:
—S—, —$SO_2$—, —O—, —$NR^{1d}$ wherein $R^{1d}$ is hydrogen or lower alkyl, —NHCO—, =N—, =CH— and —$CH_2$—; and the left side of $W^1$ is bound to the mother nucleus when $W^1$ is —NHCO—, =N— or =CH—;

n is 0, 1, 2, 3 or 4;

$W_2$ is selected from the group consisting of a single bond, —S— and —$NR^{1e}$— wherein $R^{1e}$ is hydrogen or lower alkyl;

$Q^1$, $Q^2$, and $Q^3$ are independently selected from the group consisting of hydrogen, lower alkyl, benzyl, substituted benzyl (wherein each substituent on the phenyl in the substituted benzyl independently represents 1 to 3 groups selected from halogen and $OR^{1f}$, wherein $R^{1f}$ is hydrogen or lower alkyl; and a substituent on the methylene is —$OR^{1g}$ wherein $R^{1g}$ is hydrogen or lower alkyl), phenyl, halogen, —$CF_3$, nitro, —CN, —$N_3$, —$COOR^2$, —$OR^2$, —$OCOR^2$, —$SR^2$, —$COR^2$, wherein $R_2$ is hydrogen, straight or branched alkyl having 1 to 18 carbon atoms, benzyl and phenyl —$CONR^{2a}R^{2b}$ (wherein each of $R^{2a}$ and $R^{2b}$ is independently selected from the group consisting of hydrogen, straight or branched $C_{1-18}$ alkyl, benzyl, phenyl) and methylenedioxy formed together with the ortho-position;

and pharmaceutically acceptable salts thereof.

2. A compound according to claim 1, wherein one of $R^A$ and $R^B$ represents hydrogen and the other represents —Y—COOH.

3. A compound according to claim 2, wherein Y is a member selected from the group consisting of single bond,

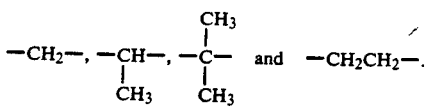

4. A compound according to claim 3, wherein $X^1$-$X^2$ represents —CH$_2$—O—, $W^1$ represents =CH—, n is 1 and $W^2$ represents single bond.

5. A compound according to claim 3, wherein $X^1$-$X^2$ represents —CH$_2$—O—; $W^1$ represents —NH—, —S—, —O—, =N— or =CH—; n is 1 or 2; and $W^2$ represents single bond.

6. A compound according to claim 1, which is selected from the group consisting of 11-[(3-pyridyl)methyl]amino-6,11-dihydrodibenz[b,e]oxepin-2-carboxylic acid,
11-[(3-pyridyl)methyl]thio-6,11-dihydrodibenz[b,e]oxepin-2-carboxylic acid,
11-[(3-pyridyl)methyl]oxy-6,11-dihydrodibenz[b,e]oxepin-2-carboxylic acid,
11-[(3-pyridyl)methyl]imino-6,11-dihydrodibenz[b,e]oxepin-2-carboxylic acid and
11-[2-(3-pyridyl)ethylidene]-6,11-dihydrodibenz[b,e]oxepin-2-carboxylic acid.

7. A compound according to claim 1, wherein said salt is selected from the group consisting of acid addition salt, metal salt, ammonium salt, organic amine addition salt and amino acid addition salt.

8. A pharmaceutical composition comprising a pharmaceutical carrier and, as an active ingredient, an effective amount of a tricyclic compound as defined by claim 1.

* * * * *

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

IN [57] ABSTRACT

In Formula, " 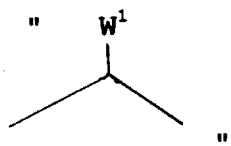 should read -- 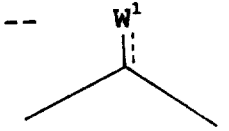 --.

COLUMN 1

Line 8, "chromboxane" should read --thromboxane--.

COLUMN 4

Line 44, "represents" should read --...... represents--.

COLUMN 8

Line 66, "wherein ," should read --wherein ......,--.

COLUMN 9

Line 20, "(IVe)" should read --(IVd)--.

COLUMN 12

Line 65, "$(CH_2)$" should read --$(CH_2)_n$--.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMN 14

Line 14, "N (CH$_2$)$_n$" should read -- N$\sim$(CH$_2$)$_n$ --.

Line 26, "N (CH$_2$)$_n$" should read -- N$\sim$(CH$_2$)$_n$ --.

Line 58, "HC (CH$_2$)$_n$" should read -- HC$\sim$(CH$_2$)$_n$ --.

COLUMN 15

Line 22, "Ph$_3$P$^\ominus$CH$_2$—(CH$_2$)$_n$—W$^2$—Z.Hal$^\oplus$" should read --Ph$_3$P$^\oplus$CH$_2$--(CH$_2$)$_n$--W$^2$--Z.Hal$^\ominus$ --.

Line 50, " $\times$ (IX) " should read -- $\times$ (IX) --.

COLUMN 17

Lines 15-35, "HC (CH$_2$)$_n$" (four occurrences) should read --HC$\sim\sim$(CH$_2$)$_n$--.

Lines 56-57, "HC CH$_2$" should read -- HC$\sim$CH$_2$ --.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMN 18

Lines 1 through 20,
"HC   $CH_2NR^{7a}R^{7b}$" should read --HC〜$CH_2NR^{7a}R^{7b}$--;
"HC   $CH_2OH$" should read --HC〜$CH_2OH$;
"HC   $CH_2Hal$" should read --HC〜$CH_2Hal$;
"HC   $CH_2O-R^5$" should read --HC〜$CH_2O-R^5$;
"HC   $CH_2-W^2-Z$" should read --HC〜$CH_2-W^2-Z$--.

COLUMN 19

Line 12, "$(R^{4a}O)_2\overset{O}{\underset{\|}{P}}-CH_2COOR^{4b} \longrightarrow$ " should read -- $(R^{4a}O)_2P--CH_2COOR^{4b} \xrightarrow{\text{(VIf)}}$ --.

COLUMN 23

Lines 12-15, " 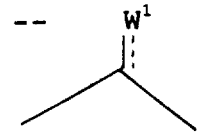 " should read -- 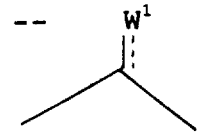 --.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMN 28

Line 20, "and          ," should read --and ......,--.

COLUMN 30

Lines 18-20, " 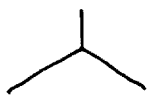 should read -- 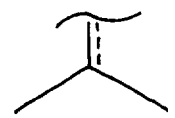 --.

Line 26, "X-X$^2$" should read --X$^1$-X$^2$--.

COLUMNS 29-30

TABLE 1, "—W$^1$—(CH$_2$)$_n$—W$^2$—Z" should read
-- ..... W$^1$—(CH$_2$)$_n$—W$^2$—Z--.

COLUMNS 31-32

TABLE 1-continued, "—W$^1$—(CH$_2$)$_n$—W$^2$—Z" should read
-- ..... W$^1$—(CH$_2$)$_n$—W$^2$—Z--.

COLUMNS 33-34

TABLE 1-continued, "—W$^1$—(CH$_2$)$_n$—W$^2$—Z" should read
-- ..... W$^1$—(CH$_2$)$_n$—W$^2$—Z--.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMNS 35-36

TABLE 1-continued, "$-W^1-(CH_2)_n-W^2-Z$" should read -- ..... $W^1-(CH_2)_n-W^2-Z$ --.

COLUMNS 37-38

TABLE 1-continued, "$-W^1-(CH_2)_n-W^2-Z$" should read -- ..... $W^1-(CH_2)_n-W^2-Z$ --.

COLUMNS 39-40

TABLE 1-continued, "$-W^1-(CH_2)_n-W^2-Z$" should read -- ..... $W^1-(CH_2)_n-W^2-Z$ --.

COLUMNS 41-42

TABLE 1-continued, "$-W^1-(CH_2)_n-W^2-Z$" should read -- ..... $W^1-(CH_2)_n-W^2-Z$ --.

COLUMNS 43-44

TABLE 1-continued, "$-W^1-(CH_2)_n-W^2-Z$" should read -- ..... $W^1-(CH_2)_n-W^2-Z$ --.

COLUMNS 45-46

TABLE 1-continued, "$-W^1-(CH_2)_n-W^2-Z$" should read -- ..... $W^1-(CH_2)_n-W^2-Z$ --.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMNS 47-48

TABLE 1-continued, "$-W^1-(CH_2)_n-W^2-Z$" should read -- ..... $W^1-(CH_2)_n-W^2-Z$ --.

COLUMNS 49-50

TABLE 1-continued, "$-W^1-(CH_2)_n-W^2-Z$" should read -- ..... $W^1-(CH_2)_n-W^2-Z$ --.

COLUMNS 51-52

TABLE 1-continued, "$-W^1-(CH_2)_n-W^2-Z$" should read -- ..... $W^1-(CH_2)_n-W^2-Z$ --.

COLUMNS 53-54

TABLE 1-continued, "$-W^1-(CH_2)_n-W^2-Z$" should read -- ..... $W^1-(CH_2)_n-W^2-Z$ --.

COLUMNS 55-56

TABLE 1-continued, "$-W^1-(CH_2)_n-W^2-Z$" should read -- ..... $W^1-(CH_2)_n-W^2-Z$ --.

COLUMNS 57-58

TABLE 1-continued, "$-W^1-(CH_2)_n-W^2-Z$" should read -- ..... $W^1-(CH_2)_n-W^2-Z$ --.

UNITED STATES PATENT AND TRADEMARK OFFICE
CERTIFICATE OF CORRECTION

PATENT NO. : 4,999,363

DATED : March 12, 1991

INVENTOR(S) : ETSUO OSHIMA, ET AL.

It is certified that error appears in the above-identified patent and that said Letters Patent is hereby corrected as shown below:

COLUMNS 59-60

TABLE 1-continued, "$-W^1-(CH_2)_n-W^2-Z$" should read -- ..... $W^1-(CH_2)_n-W^2-Z$-- and "$H_3C$" should read --$H_3CO$--.

COLUMNS 61-62

TABLE 1-continued, "$-W^1-(CH_2)_n-W^2-Z$" should read -- ..... $W^1-(CH_2)_n-W^2-Z$--.

COLUMNS 63-64

TABLE 1-continued, "$-W^1-(CH_2)_n-W^2-Z$" should read -- ..... $W^1-(CH_2)_n-W^2-Z$--.

COLUMNS 65-66

TABLE 1-continued, "$-W^1-(CH_2)_n-W^2-Z$" should read -- ..... $W^1-(CH_2)_n-W^2-Z$--.

COLUMNS 67-68

TABLE 1-continued, "$-W^1-(CH_2)_n-W^2-Z$" should read -- ..... $W^1-(CH_2)_n-W^2-Z$--.

COLUMNS 69-70

TABLE 1-continued, "$-W^1-(CH_2)_n-W^2-Z$" should read -- ..... $W^1-(CH_2)_n-W^2-Z$--.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMNS 71-72

TABLE 1-continued, "$-W^1-(CH_2)_n-W^2-Z$" should read
-- ..... $W^1-(CH_2)_n-W^2-Z$--.

COLUMN 136

TABLE 6, " 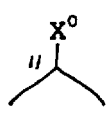 should read -- 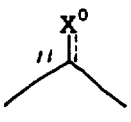 -- and "--$X^0$" should read --.....$X^0$--.

COLUMN 137

TABLE 6-continued,

" 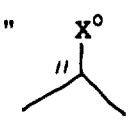 should read -- 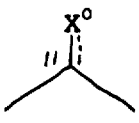 -- and "--$X^0$" should read --.....$X^0$--.

COLUMN 148

Line 14, "of;" should read --of:--.
Line 28, "$-CR^{1b}-R^{1c}-(CH_2)_m$" should read
-- $-CR^{1b}-R^{1c}-(CH_2)_m-$ --.
Line 41, "$W_2$" should read --$W^2$--.

UNITED STATES PATENT AND TRADEMARK OFFICE
CERTIFICATE OF CORRECTION

PATENT NO. : 4,999,363
DATED : March 12, 1991
INVENTOR(S) : ETSUO OSHIMA, ET AL.

It is certified that error appears in the above-identified patent and that said Letters Patent is hereby corrected as shown below:

COLUMN 148

Line 53, "$COR^2$, wherein $R_2$" should read
--$COR^2$ (wherein $R^2$--.
Line 55, "phenyl" should read --phenyl),--.

Signed and Sealed this

Seventh Day of December, 1993

Attest:

BRUCE LEHMAN

Attesting Officer     Commissioner of Patents and Trademarks